(12) United States Patent
Matsushima et al.

(10) Patent No.: US 8,946,386 B2
(45) Date of Patent: Feb. 3, 2015

(54) PROTEINS EXPRESSED IN NK CELLS

(75) Inventors: Kouji Matsushima, Chiba (JP); Shinichi Hashimoto, Tokyo (JP); Masayuki Tsuchiya, Tokyo (JP); Yuichi Hirata, Shizuoka (JP); Kenji Yoshida, Shizuoka (JP); Kazuyuki Ojima, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 2117 days.

(21) Appl. No.: 10/574,045

(22) PCT Filed: Sep. 29, 2004

(86) PCT No.: PCT/JP2004/014207
§ 371 (c)(1),
(2), (4) Date: Feb. 21, 2007

(87) PCT Pub. No.: WO2005/030955
PCT Pub. Date: Apr. 7, 2005

(65) Prior Publication Data
US 2007/0202501 A1    Aug. 30, 2007

(30) Foreign Application Priority Data
Sep. 29, 2003   (JP) ................................ 2003-338331

(51) Int. Cl.
| | | |
|---|---|---|
| A61K 38/17 | (2006.01) | |
| C07K 14/705 | (2006.01) | |
| A61K 31/00 | (2006.01) | |
| G01N 33/564 | (2006.01) | |
| G01N 33/566 | (2006.01) | |

(52) U.S. Cl.
CPC ............... *C07K 14/705* (2013.01); *A61K 31/00* (2013.01); *G01N 33/564* (2013.01); *G01N 33/566* (2013.01); *G01N 2500/00* (2013.01)
USPC ......................................................... 530/352

(58) Field of Classification Search
None
See application file for complete search history.

(56) References Cited

U.S. PATENT DOCUMENTS

| 7,109,319 | B2 | 9/2006 | Fraser |
| 7,317,087 | B2 | 1/2008 | Davis et al. |
| 2003/0175890 | A1 | 9/2003 | Fraser |
| 2006/0246065 | A1 | 11/2006 | Fraser |
| 2008/0089887 | A1 | 4/2008 | Davis et al. |
| 2008/0166340 | A1 | 7/2008 | Tureci et al. |

FOREIGN PATENT DOCUMENTS

| AU | 2003245239 A1 | 11/2003 |
| AU | 2004275500 A1 | 4/2005 |
| EP | 1201681 A1 * | 5/2002 |
| JP | 2004-208583 A | 7/2004 |
| JP | 2005-521429 A | 7/2005 |
| JP | 2007-506417 A | 3/2007 |
| WO | WO 01/49728 | 7/2001 |
| WO | 03/054152 A2 | 7/2003 |
| WO | WO 03/089624 | 10/2003 |
| WO | WO 2005/030250 | 4/2005 |

OTHER PUBLICATIONS

English language translation of the Interanational Preliminary Examination Report for PCT/JP2004/014207, mailed.*
Japanese language Machine translation of Takao et al. JP 2004-208583, translated Jun. 18, 2010, pp. 1-32.*
Long et al., Semin Immunol. Apr. 2000;12(2):101-8.*
Schreeder et al., J. Immunol. 2010;185;23-27.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Bork et al., 1996, Trends in Genetics 12:425-427.*
Brenner, 1999, Trends in Genetics 15:132-133.*
Skolnick et al., 2000, Trends in Biotech. 18(1):34-39.*
Smith et al., 1997, Nature Biotechnology 15:1222-1223.*
Doerks et al., 1998, Trends in Genetics 14:248-250.*
Billadeau et al., J. Clin. Invest. 109:161-168 (2002).*
Hashimoto et al., "Gene expression profile in human leukocytes," Blood, 101:3509-13 (2003).
Obata-Onai et al., "Comprehensive gene expression analysis of human NK cells and CD8+ T lymphocytes," Int. Immunol., 14:1085-98 (2002).
Database UniProt [Online] "Cell Surface Glycoprotein gp42 Precursor" XP002433183, Retrieved from EBI Accession No. P23505; (1991).
Farag et al., "Natural Killer Cell Receptors: New Biology and Insights into the Graft-Versus-Leukemia Effect," *Blood*, vol. 100, No. 6, pp. 1935-1947 (2002).
Seaman et al., "Molecular Cloning of gp42, A Cell-Surface Molecule That is Selectively Induced on Rat Natural Killer Cells by Interleukin 2: Glycolipid Membrane Anchoring and Capacity for Transmembrane Signaling," *The Journal of Experimental Medicine*, vol. 173, pp. 251-260 (1991).
Akbari et al., "Essential role of NKT cells producing IL-4 and IL-13 in the development of allergen induced airway hyperreactivity," Nat. Med. 9: 582-588 (2003).
Harada et al., "Regulation of Innate and Acquired Immune Systems by Vα14 NKT Cells," Tanpakushitsu Kakusan Koso, 47: 2109-16 (2002) (with English translation).
Kim et al., "In vivo natural killer cell activities revealed by natural killer cell-deficient mice," Proc. Natl. Acad. Sci. USA, 97:2731-36 (2000).
Trinchieri, "Biology of Natural Killer Cells," Adv. Immunol., 47:187-376 (1989).

* cited by examiner

*Primary Examiner* — Zachary Skelding
(74) *Attorney, Agent, or Firm* — Fish & Richardson P.C.

(57) ABSTRACT

Purified immunocytes were analyzed for expression frequencies, and the NKIR gene expressed specifically in natural killer (NK) cells was successfully identified. The NKIR gene encodes a receptor. Agonists and antagonists for the receptor can be identified by using the receptor.

19 Claims, 13 Drawing Sheets

```
Score = 263 (92.6 bits), Expect = 1.9e-28, Sum P(3) = 1.9e-28
Identities = 62/369 (50%), Positives = 78/369 (63%), Frame = -3

Query:   197 APVSRPVLTLHHGPADPAVGDMVQLLCEAQRGSPPILYSFYLDEKIVGNHSAPCGGTTSL 256
             APVS PVLTL H   + AVGD V+ LCEA +GS PI YSFY++  +I+G   AP G   SL
Sbjct: 891239 APVSHPVLTLQHEATNLAVGDKVEFLCEAHQGSLPIFYSFYINGEILGKPLAPSGRAASL
       891060

Query:   257 LFPVKSEQDAGNYSCEAENSVSRERSEPKKLSLKGSQVL--FTPA 299
             L   VK+E    NYSCEA+N++SRE  SE KK L G   +   +TP
Sbjct: 891059 LASVKAEWSTKNYSCEAKNNISREISELKKFPLVGMFCIISYTPV 980924

EXTRACELLULAR
                                            CANDIDATE REGION

EXON AT POSITION N

Score = 82 (28.9 bits), Expect = 1.9e-28, Sum P(3) = 1.9e-28
Identities = 18/75 (72%), Positives = 20/75 (80%), Frame = -2

Query:   300 SNWLVPWLPASLLGLMVIAAALLVY 324
             SN L  WLPASLLG MVIAA  +L+Y
Sbjct: 890637 SNMLPIWLPASLLGGMVIAAVVLMY 890563

TRANSMEMBRANE REGION

EXON AT POSITION N+1
```

FIG. 7

```
mMKIR   ------------------------------------------------------------
hMKIR   MLPSLVPCVCKTVWLYLQAWPNPVPGDALTLRCQQWMNTPLSQVKFYRDGKFLHFSKEN mMKIR   ----------------MLL-WMVLLLCDS-MVEAQELFPNPELTEFTNSETMD-
hMKIR   QTLSMQAATVGSRQYSCSGQVMIPQTFQTSETAMVQVQELFPPVLSAIPSPEPREG
                        *::   ***.* ****:* **.  .* mMKIR   --VILKCTIKVDPKNPTLQLFYTFYKDNHVIQDRSPH-SVFSAEAKEENSGLYQCMVDTE
hMKIR   SLVTLRCQTKLHPLRSALRLLSPHKDGHTLQDRGPHPELCIPGAKEGDSGLYWCEVAPE
          *:   * :   .:* * : :.::*..: :*.  : .*: *:*.***:*:*  * mMKIR   DGLIQKSQYLDIQFWTPVSHPVLTLQHEATNLAVQDKVEFLCEAHQGSLPIFYSFYING
hMKIR   GGQVQKGSPQLEVRVQAPVSRPVLTLRHGPADPAVGDMVQLLCEAQRGSPPILYSFYLDE
         * ::**    :: .* **:******::. *: **.** :****::**:**:****::

mMKIR   EILGKPLAPSGRAASLLASVKAEWSTKNYSCEAKNNISREISELKKFPLVVSGTAWIES-
hMKIR   KIVGNHSAPCGGTTSLLFPVKSEQDAGNYSCEAEMSVSRERSEPKKLSLKCSQVLFTPAS
         *:*:  **.* ::*** .**:*   .:*****:::::**:**:**:.*: : *: :

mMKIR   NMLTIWLPASLLGQMVIAAVVLMYFFPCKKHARLEMPTLKEPDS---PLYVSVDMRRYK
hMKIR   NMLVPWLPASLLGLMVIAAALLVYYRSNRKAGPLPSQIPTAPGGEQCPLYANVHHQKGK
        :  ***  :**.::: :   .: . *.  :   .     ***..*.::: * mMKIR   ------------------------------------------------------------
hMKIR   DEGVVYSVVHRTSKRSEARSAEPTVGRKDSSIICAEVRCLQPSEVVSSTEVMRSRTLQEP mMKIR   ------------
hMKIR   LSDCEEVLC
```

FIG. 8

PROTEINS EXPRESSED IN NK CELLS

CROSS-REFERENCE TO RELATED APPLICATIONS

This application is the National Stage of International Application No. PCT/JP2004/014207, filed on Sep. 29, 2004, which claims the benefit of Japanese Patent Application Serial No. 2003-338331, filed on Sep. 29, 2003. The contents of both of the foregoing applications are hereby incorporated by reference in their entireties.

TECHNICAL FIELD

The present invention relates to novel proteins expressed in NK cells, DNAs encoding the proteins, methods for producing the molecules, and uses thereof.

BACKGROUND ART

Cytotoxic T cells recognize complexes between major histocompatibility complex (MHC) class I molecules and specific antigen peptides (foreign substances), and are thereby activated to exert cytotoxic activity against target cells. In contrast, natural killer (NK) cells typically damage target cells expressing no MHC class I molecules. The expression of such MHC class I molecules on normal cell surface is suppressed by viral infection or canceration. NK cells exert cytotoxic activity against such abnormal cells with decreased MHC class I molecule expression levels. It is therefore thought that NK cells play a central role in the innate immunity mechanism by eliminating cancered cells or cells infected with viruses. NK cells were in fact identified as cells having the activity of spontaneously damaging certain cancer cells (see Non-Patent Document 1). Furthermore, such in vivo roles of NK cells are supported by the disease called Chediak-Higashi syndrome, which is caused by a deficiency in NK cell activity (Chediak-Higashi syndrome is due to a chromosome abnormality and enters the advanced stage when the patient is over 10 years old, making it impossible to control viral infection, and resulting in malignant lymphoma-like pathological changes and death by pancytopenia after 2 to 3 months).

Recently, transgenic mice lacking NK1.1+CD3-cells (NK cells) were generated. Analyses of their characteristics revealed that: NK cells
(i) play an important role in suppressing metastasis and growth of cancer cells; and
(ii) are major producers of interferon (IFN) γ in response to bacterial endotoxins (see Non-Patent Document 2).

Meanwhile, it has recently been found that a fourth lymphocyte, NKT cell, that has a NK cell receptor as well as an identical T cell receptor and characteristics of both innate and acquired immunities, are distributed in a wide variety of organs, including liver and bone marrow. In addition, these cells have been found to be involved in immunotolerance, and in many diseases such as autoimmune diseases, hepatitis, and infections. Based on studies using mice that develop multiple sclerosis early in life, it has been found that there is a certain relationship between NKT cells, which are immune cells included in lymphocytes, and the onset of multiple sclerosis (see Non-Patent Document 3). In addition, it has been suggested that asthma may be preventable by inactivating NKT cells, because no allergic airway hyperreactivity, which is a major asthma symptom, is detected in NKT-deficient mice (see Non-Patent Document 4). The revealed activation mechanism for NKT cells shows that unlike NK cells, NKT cells are activated through stimulation of the T cell receptor or through α-galactosylceramide (α-GalCer), which is a glucolipid presented to the CD1d receptor on dendritic cells (see Non-Patent Document 3). Meanwhile, like NK cells, NKT cells exert cytotoxic activity against cells with decreased MHC class I molecule expression levels, and is therefore thought to regulate cytotoxic activity by almost the same mechanism as the killer cell inhibitory receptor (hereinafter abbreviated as "KIR"), which has been identified as an inhibitory regulator molecule involved in the cytotoxic activity of lymphocyte populations. However, NKT subsets that do not express known KIRs are also known to exist. In addition, much was unclear about signal cascades and inhibitory receptors that act negatively in the activation, necessitating further studies.

While ligand substances that are effective for NKT cell activation have been found, low-molecular-weight ligands that specifically activate NK cells are yet to be identified.

Non-Patent Document 1: Trinchieri G., Adv Immunol. (1989), 47, 187-376

Non-Patent Document 2: Sungjin Kim, Koho Iizuka, Hector L. Aguila, Irving L. Weissman, and Wayne M. Yokoyama, Proc. Natl. Acad. Sci. (2000), 97, 2731-2736

Non-Patent Document 3: Michishige Harada, Masaru Taniguchi, Protein, Nucleic acid, and Enzyme (Tanpakushitsu Kakusan Kouso) (2002), 47, 2109-2116

Non-Patent Document 4: Akbari O, Stock P, Meyer E, Kronenberg M, Sidobre S, Nakayama T, Taniguchi M, Grusby M J, DeKruyff R H, Umetsu D T, Nat. Med. (2003), 9, 582-588

DISCLOSURE OF THE INVENTION

Problems to be Solved by the Invention

The present invention was achieved in view of the above circumstances. An objective of the present invention is to isolate receptor molecules that specifically activate or inactivate NK cells. More specifically, an objective is to provide novel receptor proteins expressed in NK cells, DNAs encoding the proteins, and uses of the molecules.

Means to Solve the Problems

The NK cell activation mechanism has been suggested to take place as a result of the regulation between the positive signal cascade, which follows phosphorylation by protein tyrosine kinase, and the negative signal cascade, which results from the dephosphorylation of the phosphorylated signaling molecule. In mouse, the inhibitory receptors on NK cells which recognize molecules driving the negative cascade are the group of Ly49 molecules (a type-C lectin family having the extracellular type-C lectin domain). In humans, they are the KIR molecule family having the extracellular immunoglobulin (Ig) domain. Details of KIR molecules and of MHC allotypes recognized by them are gradually being revealed. As apparent from the fact that NK cells exert cytotoxic activity against cells with decreased MHC class I molecule expression, most KIR molecules recognize the polymorphic classic MHC class I molecules expressed in almost all types of cells, to transmit negative signals into cells. Meanwhile, some KIR molecular species have non-classic MHC class I molecules as ligands. Accordingly, it is thought that the whole KIR molecule group plays a central role in the surveillance mechanism against autologous but abnormal cells in the natural immune system.

Like Ly49, KIR molecules also have in the cytoplasmic domain a functional sequence comprising the V/I X Y XX L/V (V, valine; I, isoleucine; Y, tyrosine; L, leucine; and X, arbitrary amino acid) motif called "ITIM". When the tyrosine residue in the ITIM motif is phosphorylated, the protein tyrosine dephosphorylation enzyme SHP-1, which comprises a SH2 domain, binds to this site. The activation of NK cells is suppressed by the SHP-1-meidated dephosphorylation of tyrosine-phosphorylated protein (SLP-76 molecule is believed to be a promising candidate) that is essential for the activation of the positive signal cascade in NK cells.

The present inventors conducted deducated studies to solve the above-described objectives. Referring to the analysis data of Serial Analysis of Gene Expression (SAGE) (Hashimoto S, Blood (2003), 101, 3509-3513) for purified immune cells (monocytes/macrophages, T cells, dendritic cells, natural killer cells, neutrophils, etc.) disclosed at http://www.prevent.m.u-tokyo.ac.jp, many tags presumed to derive from unknown genes, some with characteristic expression profiles, were identified in addition to sequence tags for known gene sequences.

Of these, the present inventors succeeded in identifying the NKIR gene expressed specifically in natural killer (NK) cells. Some characteristics of its deduced amino acid sequence suggested that the gene was a homologue of killer cell inhibitory receptor (hereinafter abbreviated as "KIR") that had been identified as a molecule that expresses in NK cells and a subset of T cells, and functions as an inhibitory regulator molecule for the cytotoxic activity of lymphocyte populations. The NKIR gene was mapped on chromosome 1, while most members belonging to the KIR molecule group are clustered on chromosome 19. The present inventors also analyzed characteristics of the gene to explore the possibility of applying the gene to drug discovery. Some sequences considered to be of splicing variants of the gene of the present invention (WO 01/49728) have been reported. The NCBI Annotation Project has also assigned a splicing variant (LOC343413) through predictions based on genomic sequences. However, the functions of these splicing variants still remain unknown. In addition, to date there is no known sequence perfectly identical to the gene of the present invention.

As described above, NK cells have anti-tumor and antiviral activities. Therefore, the anti-tumor and antiviral effects based on suppression of KIR function using an antagonistic antibody for KIR are two potential clinical applications of the present invention. Alternatively, when NKT cells are targeted, the present invention is expected to have potential uses against viral diseases such as hepatitis C or cancers by using antagonistic antibodies, or against allergic diseases, asthma, and autoimmune diseases by using agonistic antibodies.

The present invention relates to novel proteins expressed in NK cells, DNAs encoding the proteins, methods for producing the molecules, and uses thereof. Specifically, the preset invention relates to:

[1] a DNA of any one of:
(a) a DNA encoding a protein comprising the amino acid sequence of any one of SEQ ID NOs: 2, 4, and 6;
(b) a DNA comprising a coding region of the nucleotide sequence of any one of SEQ ID NOs: 1, 3, and 5;
(c) a DNA encoding a protein which comprises an amino acid sequence with a substitution, deletion, insertion, and/or addition of one or more amino acids in the amino acid sequence of any one of SEQ ID NOs: 2, 4, and 6, and which is functionally equivalent to a protein comprising the amino acid sequence of any one of SEQ ID NOs: 2, 4, and 6; and
(d) a DNA which hybridizes under stringent conditions to a DNA comprising the nucleotide sequence of any one of SEQ ID NOs: 1, 3, and 5;

[2] a DNA encoding a fragment of a protein comprising the amino acid sequence of any one of SEQ ID NOs: 2, 4, and 6;

[3] a protein encoded by the DNA of [1] or [2];

[4] a vector comprising the DNA of [1] or [2];

[5] a host cell comprising the DNA of [1] or [2], or the vector of [4];

[6] a method for producing the protein of [3], wherein the method comprises the steps of:
culturing the host cell of [5], and
collecting the protein from the host cell or a culture supernatant thereof;

[7] an antibody which binds to the protein of [3];

[8] a method for identifying a ligand for the protein of [3], wherein the method comprises the steps of:
(a) contacting a candidate compound with the protein of [3] or a cell expressing the protein of [3]; and
(b) determining whether the candidate compound binds to the protein of [3] or the cell expressing the protein of [3];

[9] a method for identifying an agonist for the protein of [3], wherein the method comprises the steps of:
(a) contacting a candidate compound with a cell expressing the protein of [3]; and
(b) determining whether the candidate compound generates a signal that is an indicator of activation of the protein of [3];

[10] a method for identifying an antagonist for the protein of [3], wherein the method comprises the steps of:
(a) contacting a candidate compound with a cell expressing the protein of [3]; and
(b) determining whether a signal as an indicator of activation of the protein of [3] is reduced as compared with a detection result obtained in absence of the candidate compound;

[11] a ligand for the protein of [3], which can be identified by the method of [8];

[12] an agonist for the protein of [3], which can be identified by the method of [9];

[13] an antagonist for the protein of [3], which can be identified by the method of [10];

[14] a kit to be used in the method of any one of [8] to [10], wherein the kit comprises at least one of:
(a) the protein of [3]; and
(b) the host cell of [5];

[15] an immunosuppressant, which comprises as an active ingredient an agonist for the protein of [3] (or the agonist of [12]);

[16] a therapeutic agent for an allergic disease or autoimmune disease, wherein the method comprises as an active ingredient an agonist for the protein of [3] (or the agonist of [12]);

[17] an immunopotentiator, which comprises as an active ingredient an antagonist for the protein of [3] (or the antagonist of [13]);

[18] an anti-tumor or antiviral agent, which comprises as an active ingredient an antagonist for the protein of [3] (or the antagonist of [13]);

[19] a DNA, which comprises at least 15 nucleotides and which is complementary to the DNA of [1] or [2], or to a complementary strand thereof; and

[20] a diagnostic reagent for a disease associated with an abnormality in the expression or activity of a gene encoding the protein of [3], wherein the diagnostic reagent comprises the DNA of [19] or the antibody of [7].

In an alternative embodiment, the present invention provides:
(a) use of the proteins of the present invention in screening for an agonist or antagonist for the proteins;
(b) use of an agonist for the proteins of the present invention in the production of immunosuppressants;
(c) use of an agonist for the proteins of the present invention in the production of therapeutic agents for allergic diseases or autoimmune diseases;
(d) use of an antagonist for the proteins of the present invention in the production of immunopotentiators; and
(e) use of an antagonist for the proteins of the present invention in the production of anti-tumor or antiviral agents.

The present invention also relates to the following methods:
(a) a method for suppressing immunological function, which comprises the step of administering an agonist for the proteins of the present invention to subjects (patients or the like);
(b) a method for treating (or preventing) allergic or autoimmune diseases, which comprises the step of administering an agonist for the proteins of the present invention to subjects (patients or the like);
(c) a method for enhancing immunological function, which comprises the step of administering an antagonist for the proteins of the present invention to subjects (patients or the like); and
(d) a method for treating (or preventing) cancers (tumors) or viral diseases, which comprises the step of administering an antagonist for the protein of the present invention to subjects (patients or the like).

BRIEF DESCRIPTION OF THE DRAWINGS

FIG. 3A shows MTC panels I and II;
and FIG. 3B shows Immune System and Blood Fraction. Each lane is as follows:
FIG. 3A:
Lane 1, heart; lane 2, brain; lane 3, placenta; lane 4, lung; lane 5, liver; lane 6, skeletal muscle; lane 7, kidney; lane 8, pancreas; lane 9, spleen; lane 10, thymus; lane 11, prostate; lane 12, testis; lane 13, ovary; lane 14, small intestine; lane 15, large intestine; and lane 16, peripheral blood leukocyte.
FIG. 3B:
Lane 1, spleen; lane 2, lymph nodes; lane 3, thymus; lane 4, peripheral blood leukocytes; lane 5, tonsilla; lane 6, fetal liver; lane 7, bone marrow; lane 8, mononuclear cells; lane 9, resting CD8+ cells; lane 10, resting CD4+ cells; lane 11, resting CD14+ cells; lane 12, resting CD19+ cells; lane 13, activated CD19+ cells; lane 14, activated mononuclear cells; lane 15, activated CD4+ cells; and lane 16, activated CD8+ cells.

FIG. 7 shows a result of a BLAST search using human NKIR as a query, which is aligned with a matching mouse chromosomal sequence.

FIG. 8 shows the alignment of human and mouse NKIR sequences.

FIG. 11-1 is a diagram showing CD8 chimeric structures of three clones selected in Example 16.

FIG. 11-2 is a graph showing a FACS analysis result for clones as described below using anti-CD8 antibody, LT8 (Serotec), and FITC-conjugated goat anti-mouse IgG antibody (Coulter) used in Example 17. FIG. 11-2A, F11 clone in the absence of LT8 (primary antibody); FIG. 11-2B, F11 clone in the presence of LT8 (primary antibody); FIG. 11-2C, CD8 chimeric clone in the absence of LT8 (primary antibody); and FIG. 11-2D, CD8 chimeric clone in the presence of LT8 (primary antibody).

DETAILED DESCRIPTION

Figure 1:
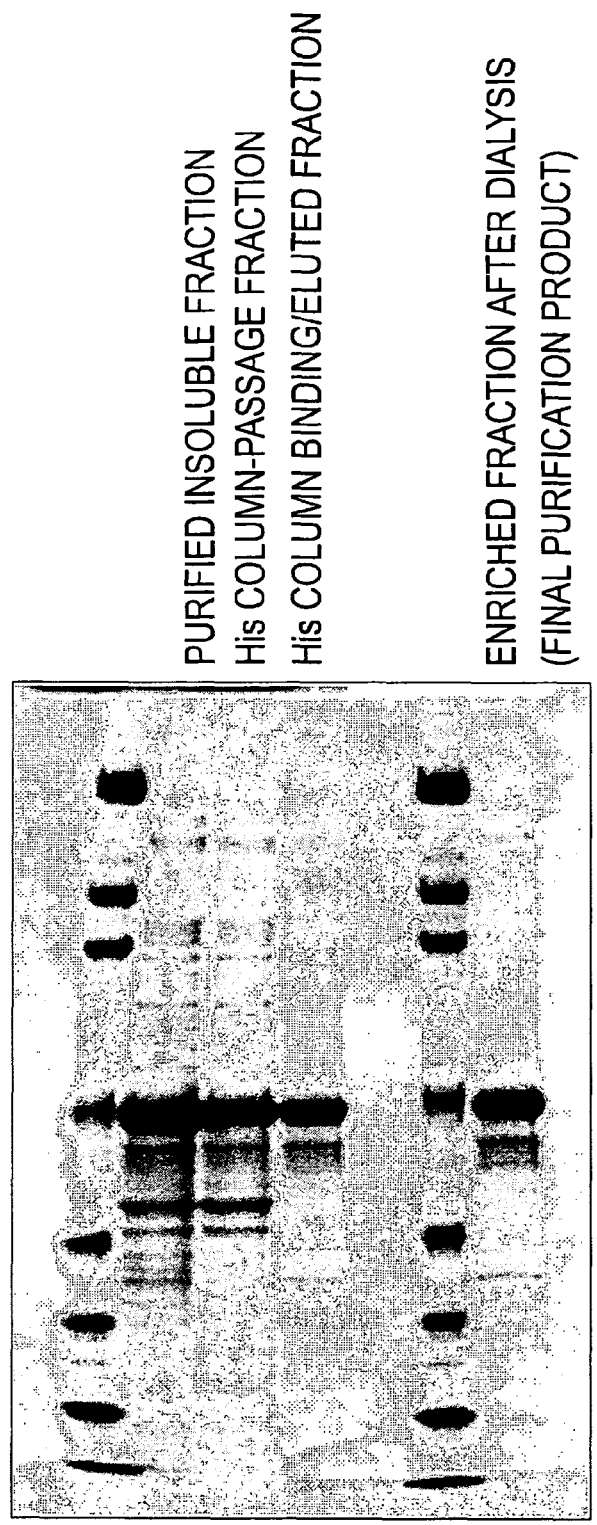
FIG. 1 is a photograph showing an SDS-PAGE electrophoresis analysis result for NKIR fusion protein purified using a His trap column.

The present inventors cloned genes specifically expressed in NK cells from a human spleen cDNA library using PCR. The yielded clones included multiple clones that were thought to be splicing variants. Hence, the inventors carried out 5' RACE to obtain the native sequence, and identified NKIR gene that was thought to belong to the KIR family. The nucleotide sequence of the gene is shown in SEQ ID NO: 1, and the amino acid sequence of the protein encoded by the gene is shown in SEQ ID NO: 2. Furthermore, the present inventors recloned the full-length NKIR gene by 5'- and 3'-RACE methods using total RNAs prepared from NK-92 cell line, and obtained a clone comprising a sequence that had a 36-nucleotide signal-like sequence at the 5' end and approximately 500-nucleotide sequence extension at the 3' end. The nucleotide sequence of the clone is shown in SEQ ID NO: 3, and the amino acid sequence of the protein encoded by the nucleotide sequence is shown in SEQ ID NO: 4. Furthermore, the present inventors carried out cloning of mouse NKIR sequence. The nucleotide sequence thus obtained is shown in SEQ ID NO: 5, and the amino acid sequence of the protein encoded by the nucleotide sequence is shown in SEQ ID NO: 6.

The present invention provides novel proteins expressed in NK cells, and DNAs encoding the proteins. In a preferred embodiment, DNAs of the present invention are as follows:
(a) a DNA encoding a protein comprising the amino acid sequence of any one of SEQ ID NOs: 2, 4, and 6;
(b) a DNA comprising a coding region of the nucleotide sequence of any one of SEQ ID NOs: 1, 3, and 5;
(c) a DNA encoding a protein which comprises an amino acid sequence with a substitution, deletion, insertion, and/or addition of one or more amino acids in the amino acid of any one of SEQ ID NOs: 2, 4, and 6, and which is functionally equivalent to a protein comprising the amino acid sequence of any one of SEQ ID NOs: 2, 4, and 6; and
(d) a DNA which hybridizes under stringent conditions to a DNA comprising the nucleotide sequence of any one of SEQ ID NOs: 1, 3, and 5
(more preferably, a DNA which hybridizes under stringent conditions to a DNA comprising the nucleotide sequence of any one of SEQ ID NOs: 1, 3, and 5, and which encodes a protein functionally equivalent to a protein comprising the amino acid sequence of any one of SEQ ID NOs: 2, 4, and 6).

The present invention includes proteins that are functionally equivalent to the proteins expressed in NK cells (proteins comprising the amino acid sequence of SEQ ID NO: 2, 4, or 6; hereinafter sometimes referred to as "NKIR protein"), which were identified by the present inventors. Such proteins include, for example, mutants of the present proteins and homologues thereof derived from species other than human and mouse. Herein, the phrase "functionally equivalent" means that a protein of interest has a biological or biochemical activity identical to that of NKIR protein. Such activities include, for example: activities that KIR has; the activity of suppressing the cytotoxic activity of NK cells; and the activity of a KIR molecule to suppress activated signaling in immunocytes that have similar intracellular signaling for activation, such as T cell and mast cell hosts, into which the KIR molecule is introduced. Therefore, whether a protein of interest has a biological or biochemical activity equivalent to that of a protein identified by present inventors can be evaluated by, for example, a method that detects the inhibitory activity against the activation signaling of immunocytes to which the molecule (protein of interest) has been introduced by transduction and such, by measuring the cytoplasmic calcium concentration (Bruhns P., Marchetti P., Fridman W H., Vivier E., Daeron M., J. Immunol. (1999), 162, 3168-3175), or by assaying the expression level of a reporter gene comprising an NF-AT cis sequence under the regulation of the calcineurin cascade (Fry A M., Lanier L L., Weiss A., J Exp Med. (1996), 184, 295-300). In addition, when mast cells are used as host cells, a method that assays $^3$H-labeled serotonin to detect release of serotonin downstream of Ca cascade (Blery M., Delon J., Trautmann A., Cambiaggi A., Olcese L., Biassoni R., Moretta L., Chavrier P., Moretta A., Daeron M., Vivier E., J Biol. Chem. (1997), 272, 8989-8996) can be used.

To prepare a protein functionally equivalent to another protein, for example, methods for introducing mutations into amino acids in proteins are well known to those skilled in the art. Specifically, those skilled in the art can prepare a protein functionally equivalent to proteins comprising the amino acid sequence of SEQ ID NO: 2, 4, or 6 by introducing an appropriate mutation into an amino acid(s) of the sequences using site-directed mutagenesis (Hashimoto-Gotoh T. et al. Gene 152: 271-275(1995); Zoller M. J. and Smith M. Methods Enzymol. 100: 468-500(1983); Kramer W. et al. Nucleic Acids Res. 12: 9441-9456 (1984); Kramer W. and Fritz H. J. Methods Enzymol. 154: 350-367(1987); Kunkel T. A. Proc. Natl. Acad. Sci. USA 82: 488-492 (1985); Kunkel T. A. Methods Enzymol. 85: 2763-2766 (1988)). Amino acid mutations may also occur in nature. Thus, both artificially synthesized and naturally occurring proteins comprising an amino acid sequence in which one or more amino acids in the sequence of the NKIR protein identified by the present inventors are mutated, and which is functionally equivalent to the MC-PIR1 or MC-PIR2 protein, are also included in the present invention. In such a mutant protein, the number of mutated amino acids is usually 50 or less, preferably 30 or less, and more preferably 10 or less (for example, five amino acids or less).

Sites to be mutagenized are not particularly limited, but preferably are those other than motifs and domains as described below.

In mutating an amino acid, it is preferable to change it into another amino acid that allows the properties of the amino acid side chain to be conserved. For example, amino acid side chain characteristics are: side chains having hydrophobic amino acid residues (A, I, L, M, F, P, W, Y, V), hydrophilic residues (R, D, N, C, E, Q, G, H, K, S, T), residues with an aliphatic side chain (G, A, V, L, I, P), residues with a side chain containing a hydroxyl group (S, T, Y), residues with a side chain containing sulfur (C, M), residues with a side chain containing a carboxylic acid and amide group (D, N, E, Q), basic residues (R, K, H), and aromatic residues (H, F, Y, W) (amino acids are shown using the one letter code in the parentheses).

It is already known that a protein having a modified amino acid sequence, in which one or more amino acids are deleted, added, and/or substituted with another amino acid, can maintain the original biological activity (Mark D. F. et al. Proc. Natl. Acad. Sci. USA 81: 5662-5666 (1984); Zoller M. J. and Smith M. Nucleic Acids Res. 10: 6487-6500 (1982); Wang A. et al. Science 224: 1431-1433; Dalbadie-McFarland G. et al. Proc. Natl. Acad. Sci. USA 79: 6409-6413 (1982)).

A protein comprising an amino acid sequence in which multiple amino acid residues are added to the sequence of NKIR protein includes fusion proteins comprising the protein. Fusion proteins such as those between the proteins of this invention and other peptides or proteins are included in the present invention. To produce a fusion protein, a DNA encoding the NKIR protein (comprising the amino acid sequence according to SEQ ID NO: 2, 4, or 6) and a DNA encoding another peptide or protein are ligated so that their frames match, and introduced into an expression vector to express in a host. Any method commonly known to those skilled in the art can be used. Any peptide or protein may be used for making fusion proteins with proteins of this invention.

Known peptides that can be used as peptides that are fused to the proteins of the present invention include, for example, FLAG (Hopp, T. P. et al., Biotechnology (1988) 6, 1204-1210), 6×His containing six histidine (HIS) residues, 10×His, HA (Influenza agglutinin), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to proteins of the present invention include GST (glutathione-5-transferase), HA (Influenza agglutinin), immunoglobulin constant region, β-galactosidase, MBP (maltose-binding protein), and such. Fusion proteins can be prepared by fusing commercially available DNA encoding the fusion peptides or proteins discussed above, with the DNA encoding the proteins of the present invention, and expressing the prepared fused DNA.

An alternative method known in the art to isolate functionally equivalent proteins is, for example, the method using hybridization (Sambrook, J. et al., Molecular Cloning 2nd ed. 9.47-9.58, Cold Spring Harbor Lab. Press, 1989). One skilled in the art can readily isolate a DNA having high homology with an entire or partial DNA sequence (SEQ ID NO: 1, 3, or 5) that encodes the NKIR protein from homogenous or heterogenous organism-derived DNA samples, and isolate proteins functionally equivalent to the NKIR protein using the isolated DNA.

The present invention includes proteins encoded by DNA that hybridize with DNA encoding the NKIR protein, and which are functionally equivalent to the NKIR protein. Such proteins include, for example, homologues in humans, mice, or other mammals (for example, a protein encoded by a rat, rabbit, bovine, or simian homologous gene).

The conditions for hybridization used for isolating a DNA encoding a protein functionally equivalent to the NKIR protein can be appropriately selected by those skilled in the art.

For example, low stringent conditions may be used for hybridization. Low stringent conditions are post-hybridization washing in 0.1×SSC, 0.1% SDS at 42° C., for example, and preferably in 0.1×SSC, 0.1% SDS at 50° C. Highly stringent conditions are more preferable, which are washing in 5×SSC, 0.1% SDS at 65° C., for example. Under these conditions, a DNA having a higher homology can be efficiently obtained by increasing the temperature. Multiple factors including the temperature, salt concentration, and such are considered to affect the stringency of hybridization; one skilled in the art can achieve similar stringencies by appropriately selecting these factors.

Furthermore, by using a gene amplification technique (PCR)(Current protocols in Molecular Biology edit. Ausubel et al. (1987) Publish. John Wiley & Sons Section 6.1-6.4) in place of hybridization, DNA fragments that are highly homologous to a DNA sequence (SEQ ID NO: 1, 3, or 5) encoding a protein identified by the present inventors can be isolated using primers designed based on portions of the DNA sequence encoding the protein identified by the present inventors, to obtain a protein that is functionally equivalent to the protein identified by the present inventors based on the DNA fragment.

Proteins of the present invention may be "mature" proteins or portions of larger proteins, such as fusion proteins. The proteins of the present invention may comprise a leader sequence, a pro-sequence, a sequence useful for purification, such as multiple histidine residues, or a sequence attached to ensure stability during recombinant production.

Normally, such a protein encoded by the DNA isolated using the above hybridization techniques or gene amplification, and which is functionally equivalent to the NKIR protein, has a high homology with the protein (comprising the amino acid sequence of SEQ ID NO: 2, 4, or 6) at the amino acid level. The proteins of this invention include proteins functionally equivalent to the NKIR protein, and having a high homology with the protein at the amino acid level. High homology normally means an identity of at least 50% or more at the amino acid level, preferably 75% or more, more preferably 85% or more, and most preferably 95% or more. Homology between proteins can be determined according to the algorithm described in literature (Wilbur W. J. and Lipman D. J. Proc. Natl. Acad. Sci. USA 80: 726-730 (1983)).

The identity of amino acid sequences can be determined, for example, using the BLAST algorithm of Karlin and Altschul (Proc. Natl. Acad. Sci. USA 87:2264-2268, 1990; and Proc. Natl. Acad. Sci. USA 90:5873-5877, 1993). Based on this algorithm, a program called BLASTX has been developed (Altschul et al. J. Mol. Biol. 215: 403-410, 1990). When amino acid sequences are analyzed using BLASTX, parameters are set, for example, as follows: score=50 and wordlength=3. When BLAST and Gapped BLAST programs are used, default parameters of each program may be used. The specific procedures of these analytic methods are known (http://www.ncbi.nlm.nih.gov.).

The proteins of the present invention may have variations in the amino acid sequence, molecular weight, isoelectric point, or presence or composition of sugar chains, depending on the cell or host used for producing it, or the method of purification, as described later on. Nevertheless, such proteins are included in the present invention as long as they are functionally equivalent to the proteins of the pressent invention.

The proteins of the present invention can be prepared as recombinant proteins or natural proteins, by methods well known to those skilled in the art. A recombinant protein can be prepared, for example, by: inserting a DNA that encodes a protein of the present invention (for example, the DNA comprising the nucleotide sequence of SEQ ID NO: 1, 3, or 5), into an appropriate expression vector; introducing the vector into an appropriate host cell; collecting the thus obtained recombinants; obtaining an extract thereof; and purifying the protein by subjecting the extract to a chromatography. Examples of chromatographies are ion exchange chromatography, reverse phase chromatography, gel filtration, or affinity chromatography utilizing a column to which antibodies against proteins of the present invention are immobilized, or combinations of more than one of the aforementioned columns.

When the proteins of the present invention are expressed within host cells (for example, animal cells or E. coli) as fusion proteins with the glutathione-S-transferase protein, or as a recombinant protein supplemented with multiple histidines, the expressed recombinant protein can be purified using a glutathione column or nickel column. After purifying the fusion protein, it is also possible to exclude regions other than the objective protein by cutting with thrombin or factor-Xa as required.

A natural protein may be isolated by a method known to those skilled in the art, for example, through purification by applying tissues or cell extracts expressing proteins of this invention onto an affinity column in which an antibody (described below) capable of binding to the proteins has been immobilized. Both monoclonal and polyclonal antibodies can be used.

The present invention also provides fragments (partial peptides) of the proteins of the present invention. Such fragments are proteins that comprise an amino acid sequence identical to a partial but not full-length amino acid sequence of the above-described proteins of the present invention. The fragments of the proteins of the present invention are typically protein fragments consisting of a sequence of 8 or more amino acid residues, preferably 12 or more amino acid residues (for example, 15 or more amino acid residues). The preferred fragment includes, for example, truncated polypeptides that comprise an amino acid sequence with deletion of either or both of stretches of amino or carboxy terminal residues. Fragments having structural or functional features are also preferred, such as those comprising an $\alpha$ helix and an $\alpha$ helix-forming region, a $\beta$ sheet and a $\beta$ sheet-forming region, a turn and a turn-forming region, a coil and a coil-forming region, a hydrophilic region, a hydrophobic region, an $\alpha$ amphipathic region, a $\beta$ amphipathic region, a variable region, a surface-forming region, a substrate-binding region, or a highly antigenic region. Biologically active fragments are also preferred. Such biologically active fragments are those having the activity of the proteins of the present invention, which include fragments having similar activity, fragments with enhanced activity, and fragments in which unfavorable activities have been decreased. Such fragments include, for example, those having the activity of initiating intracellular signaling in response to ligand binding. The fragments also include those exhibiting antigenicity or immunogenicity in animals, in particular humans. Preferably, such a protein fragment has a biological and biochemical activity, including antigenic activity, of a protein of the present invention. Mutants of the identified sequences and fragments are also included in the present invention. The preferred mutants are those that are different from the original sequence due to substitution between amino acids belonging to the same type, i.e., those in which a certain residue has been substituted by an alternative residue having similar properties. Such substitutions are typically those between Ala, Val, Leu, and Ile; Ser and Thr; the acidic residues Asp and Glu; Asn and Gln; the basic residues Lys and Arg; and the aromatic residues Phe and Tyr.

The above-described protein fragments of the present invention are not limited to any particular fragments. However, the fragments preferably comprise at least a motif or domain as described below.

The above-described fragments may be useful, for example, for preparing antibodies against the proteins of this invention, in screenings for compounds that can be ligands that bind to the proteins, and in screenings for agonists or antagonists of the proteins.

The protein fragments (partial peptides) of this invention can be produced using genetic engineering, by commonly known peptide synthesis methods, or digesting proteins of this invention with appropriate peptidases. Synthesis of protein fragments (partial peptides) may be performed, for example, by either solid phase synthesis or liquid phase synthesis.

Herein, the term "ligands" refers to molecules that bind to the proteins of the present invention. The ligands include natural and synthetic ligands. The term "agonists" refers to molecules that bind to and activate the proteins of the present invention; and "antagonists" refers to molecules that inhibit the activation of the proteins of the present invention.

A DNA encoding a protein of the present invention would be useful not only for producing the protein in vivo or in vitro as described above, but also for applications in gene therapy of a disease caused by an abnormal function of the gene encoding the protein or a disease that can be treated with the protein, DNA diagnostics, etc. DNAs of this invention can take any form as long as they encode proteins of this invention. cDNAs synthesized from mRNAs, genomic DNAs, and chemically-synthesized DNAs can be used. In addition, DNAs comprising any nucleotide sequence based on the degeneracy of genetic code are included as long as they encode proteins of this invention.

DNAs of this invention can be prepared by methods commonly known to those skilled in the art. For example, they may be prepared by making a cDNA library from cells expressing proteins of this invention, and performing hybridization using a partial nucleotide sequence of the DNA (for example, SEQ ID NO: 1, 3, or 5) as a probe. The cDNA library may be prepared, for example, according to the method described in literature (Sambrook J. et al. Molecular Cloning, Cold Spring Harbor Laboratory Press (1989)), or obtained from a commercial source. Alternatively, the DNAs of this invention may be prepared as follows: RNA is prepared from cells expressing proteins of this invention, from which cDNA is synthesized using reverse transcriptase. Then, oligo DNA is synthesized based on the sequence of the DNA (for example, SEQ ID NO: 1, 3, or 5), and used as a primer in a PCR reaction to amplify a cDNA encoding a protein of this invention.

Furthermore, the coding region of the cDNA can be determined by determining the nucleotide sequence of the obtained cDNA, and the amino acid sequences of proteins of this invention can be thus obtained. In addition, the obtained cDNA may be used as a probe for screening a genomic DNA library to isolate a genomic DNA.

Specific procedures are as follows: First, mRNA is isolated from a cell, tissue, or organ expressing a protein of this invention (for example, NK cells or tissues in which expression was detected in the Example below). mRNA may be isolated by preparing total RNA using a commonly known method such as guanidine ultracentrifugation (Chirgwin J. M. et al. Biochemistry 18: 5294-5299 (1979)), or AGPC method (Chomczynski P. and Sacchi N. Anal. Biochem. 162: 156-159 (1987)), and then purifying mRNA from total RNA using an mRNA Purification Kit (Pharmacia), etc. Alternatively, mRNA may be directly prepared using the QuickPrep mRNA Purification Kit (Pharmacia).

The obtained mRNA is used to synthesize cDNA using reverse transcriptase. cDNA may be synthesized by using a commercially available kit such as the AMV Reverse Transcriptase First-strand cDNA Synthesis Kit (Seikagaku Kogyo). Alternatively, using a primer described herein, or such, cDNA may be synthesized and amplified following the 5'-RACE method (Frohman M. A. et al. Proc. Natl. Acad. Sci. U.S.A. 85:8998-9002 (1988); Belyavsky A. et al. Nucleic Acids Res. 17:2919-2932 (1989)) using the 5'-Ampli FINDER RACE Kit (Clontech) and the polymerase chain reaction (PCR). A desired DNA fragment is prepared from PCR products and ligated with a vector DNA to produce a recombinant vector construct. This construct is used to transform E. coli or such, and desired recombinant vectors are prepared from a selected colony/colonies. The nucleotide sequence of the desired DNA can be verified by conventional methods such as dideoxynucleotide chain termination.

The nucleotide sequences of DNAs of the present invention may be designed to be expressed more efficiently by taking into account the frequency of codon usage in the host used for the expression (Grantham R. et al. Nucleic Acids Res. 9: r43-74 (1981)). The DNAs of the present invention may be altered by a commercially available kit or a conventional method. For instance, the DNAs may be altered by digestion with restriction enzymes, insertion of a synthetic oligonucleotide or an appropriate DNA fragment, addition of a linker, or insertion of an initiation codon (ATG) and/or a stop codon (TAA, TGA, or TAG).

In addition, the DNAs of this invention include a DNA that hybridizes with a DNA comprising the nucleotide sequence shown as SEQ ID NO: 1, 3, or 5 and encodes a protein functionally equivalent to an above-described protein of this invention. Hybridization conditions may be appropriately chosen by one skilled in the art. Specifically, the above-described specific conditions may be used. Under these conditions, the higher the temperature, the higher the homology of the obtained DNA would be. The above hybridizing DNA is preferably a naturally occurring DNA, for example, a cDNA or genomic DNA.

The present invention also provides vectors into which a DNA of the present invention has been inserted. Vectors of the present invention are useful to maintain DNAs of the present invention in a host cell, or to express proteins of the present invention.

When the host cell is E. coli and a vector of the present invention is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol, or the like). For example, M13-series vectors, pUC-series vectors, pBR322, pBluescript, pCR-Script, etc. can be used. In addition to the vectors described above, pGEM-T, pDIRECT, and pT7 can also be used for subcloning and extracting cDNA. When a vector is used to produce a protein of the present invention, an expression vector is especially useful. For example, an expression vector to be expressed in E. coli should have the above characteristics to be amplified in E. coli. When E. coli such as JM109, DH5α, HB101, or XL1 Blue are used as a host cell, the vector should have a promoter, for example, the lacZ promoter (Ward et al., Nature (1989) 341, 544-546; FASEB J (1992) 6, 2422-2427), araB promoter (Better et al., Science (1988) 240, 1041-1043), or T7 promoter or the like, that can efficiently express the desired gene in *E. coli*. In this respect, pGEX-5X-1 (Pharmacia), "QIAexpress system" (Qiagen), pEGFP and pET (in this case, the host is preferably BL21 which expresses T7 RNA polymerase), for example, can be used in addition to the above vectors.

Additionally, the vector may also contain a signal sequence for polypeptide secretion. An example of a signal sequence that directs the protein to be secreted to the periplasm of the *E. coli* is the pelB signal sequence (Lei, S. P. et al., J. Bacteriol. (1987) 169, 4379). Means for introducing the vectors into target host cells include, for example, the calcium chloride method and the electroporation method.

In addition to *E. coli*, for example, expression vectors derived from mammals (for example, pcDNA3 (Invitrogen) and pEGF-BOS (Nucleic Acids. Res. 1990, 18 (17), p5322), pEF, pCDM8), expression vectors derived from insect cells (for example, "Bac-to-BAC baculovirus expression system" (GIBCO BRL), pBacPAK8), from plants (for example pMH1, pMH2), from animal viruses (for example, pHSV, pMV, pAdexLcw), from retroviruses (for example, pZIPneo), from yeast (for example, "*Pichia* Expression Kit" (Invitrogen), pNV11, SP-Q01), and from *Bacillus subtilis* (for example, pPL608, pKTH50) can be used as vectors for producing proteins of the present invention.

For the purpose of expression in animal cells such as CHO, COS, or NIH3T3 cells, the vector should have a promoter necessary for expression in such cells, for example, the SV40 promoter (Mulligan et al., Nature (1979) 277, 108), the MMLV-LTR promoter, the EF1α promoter (Mizushima et al., Nucleic Acids Res. (1990) 18, 5322), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, when the aim is to stably express a gene and at the same time increase the copy number of the gene in cells, one can use the method for introducing, into CHO cells in which the nucleic acid synthesizing pathway is deleted, a vector comprising the complementary DHFR gene (for example pCHO I) and then amplifying this by methotrexate (MTX). Furthermore, when the aim is to transiently express a gene, one can use the method for transfecting a vector comprising a replication origin of SV40 (pcD, etc.) into COS cells comprising the SV40 T antigen expressing gene on the chromosome. The replication origin may also be derived from the polyoma virus, adenovirus, bovine papilloma virus (BPV), and the like. Furthermore, the expression vector may carry, as a selection marker, the aminoglycoside transferase (APH) gene, thymidine kinase (TK) gene, *E. coli* xanthine-guanine-phosphoribosyl transferase (Ecogpt) gene, dihydrofolate reductase (dhfr) gene, and such, for increasing the copy number in the host cell system.

DNAs of the present invention can further be expressed in vivo in animals, for example, by inserting the DNAs into an appropriate vector and introducing it into living bodies by methods such as the retrovirus method, the liposome method, the cationic liposome method, and the adenovirus method. Gene therapy against diseases attributed to mutation of genes encoding proteins of the present invention can be thus accomplished. An adenovirus vector (for example pAdexlcw) or retrovirus vector (for example, pZIPneo) can be given as an example of a vector, but the vector is not restricted thereto. General gene manipulations, such as insertion of DNAs of the present invention to a vector, can be performed according to conventional methods (Molecular Cloning, 5.61-5.63). Administration into a living body can be either an ex vivo method, or in vivo method.

The present invention further provides host cells into which vectors of the present invention have been transfected. The host cells into which vectors of the present invention are transfected are not particularly limited. For example, *E. coli*, various animal cells and such can be used. The host cells of the present invention can be used, for example, as a production system for producing or expressing proteins of the present invention. The present invention provides methods for producing proteins of the present invention both in vitro and in vivo. For in vitro production, eukaryotic cells or prokaryotic cells can be used as host cells.

Useful eukaryotic cells may be animal, plant, or fungi cells. Animal cells include, for example, mammalian cells such as CHO (J. Exp. Med. 108:945 (1995)), COS, 3T3, myeloma, baby hamster kidney (BHK), HeLa, or Vero cells; amphibian cells such as *Xenopus* oocytes (Valle et al. Nature 291:340-358 (1981)); or insect cells such as Sf9, Sf21, or Tn5 cells. CHO cells lacking the DHFR gene (dhfr-CHO) (Proc. Natl. Acad. Sci. U.S.A. 77:4216-4220 (1980)) or CHO K-1 (Proc. Natl. Acad. Sci. U.S.A. 60:1275 (1968)) may also be used. Of animal cells, CHO cells are particularly preferable for large scale expression. A vector can be transfected into host cells by, for example, the calcium phosphate method, the DEAE-dextran method, the cationic liposome DOTAP (Boehringer Mannheim), the electroporation method, the lipofection method, and such.

As plant cells, plant cells derived from *Nicotiana tabacum* are known as protein-production systems, and may be used as callus cultures. As fungi cells, yeast cells such as *Saccharomyces*, including *Saccharomyces cerevisiae*, or filamentous fungi such as *Aspergillus*, including *Aspergillus niger*, are known and may be used herein.

Useful prokaryotic cells include bacterial cells such as *E. coli*, for example, JM109, DH5α, and HB101. Other bacterial systems include *Bacillus subtilis*.

These cells are transformed by a desired DNA, and the resulting transformants are cultured in vitro to obtain the protein. Transformants can be cultured using known methods. Culture medium for animal cells include, for example, DMEM, MEM, RPMI 1640, and IMDM. These may be used with or without a serum supplement such as the fetal calf serum (FCS). The pH of the culture medium is preferably between about 6 and 8. Such cells are typically cultured at about 30 to 40° C. for about 15 to 200 hr, and the culture medium may be replaced, aerated, or stirred if necessary.

Animal or plant hosts may be used for the in vivo production. For example, a desired DNA can be transfected into an animal or plant host. Encoded proteins are produced in vivo, and then recovered. These animal and plant hosts are included in the host cells of the present invention.

Animals used for the production system described above include, but are not limited to, mammals and insects. Mammals such as goats, pigs, sheep, mice, and cows may be used (Vicki Glaser, SPECTRUM Biotechnology Applications (1993)). Alternatively, the mammals may be transgenic animals.

For instance, a desired DNA may be prepared as a fusion gene, by fusing it with a gene such as the goat β casein gene which encodes a protein specifically produced into milk. DNA fragments comprising the fusion gene are injected into goat embryos, which are then implanted in female goats. Proteins are recovered from milk produced by the transgenic goats (i.e., those born from the goats that had received the embryos) or from their offspring. To increase the amount of milk containing the proteins produced by the transgenic goats, appropriate hormones may be administered to them (Ebert K. M. et al. Bio/Technology 12:699-702 (1994)).

Alternatively, insects, such as the silkworm, may be used. A DNA encoding a desired protein inserted into baculovirus can be used to transfect silkworms, and the desired protein may be recovered from their body fluid (Susumu M. et al. Nature 315: 592-594 (1985)).

As plants, for example, tobacco can be used. When using tobacco, a DNA encoding a desired protein may be inserted into a plant expression vector such as pMON530, which is introduced into bacteria such as *Agrobacterium tumefaciens*. Then, the bacteria are used to transfect a tobacco plant such as *Nicotiana tabacum*, and a desired polypeptide is recovered from the leaves (Julian K.-C. Ma et al., Eur. J. Immunol. 24: 131-138 (1994)).

Proteins of the present invention obtained as above may be isolated from the inside or outside (such as culture medium) of host cells, and purified as a substantially pure homogeneous protein.

The present invention provides methods for producing proteins of the present invention, which comprise the steps of: culturing host cells of the present invention; and collecting thus produced proteins from the host cells or culture supernatant thereof.

The method for protein isolation and purification is not limited to any specific method, and any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Examples of chromatographies include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by a liquid chromatography such as HPLC and FPLC. Thus, the present invention provides highly purified proteins prepared by the above methods.

Proteins of the present invention may be optionally modified or partially deleted by treating them with an appropriate protein modification enzyme before or after purification. Useful protein modification enzymes include, but are not limited to, trypsin, chymotrypsin, lysylendopeptidase, protein kinase, glucosidase and such.

The present invention provides antibodies that bind to the proteins of the present invention. The antibodies can take any form such as monoclonal or polyclonal antibodies, and includes antiserum obtained by immunizing animals such as a rabbit with proteins of the present invention, all classes of polyclonal and monoclonal antibodies, human antibodies, and humanized antibodies produced by genetic recombination.

Proteins of the present invention used as antigens to obtain an antibody may be derived from any animal species, but are preferably derived from a mammal such as a human, mouse, or rat, more preferably a human. A human-derived protein may be obtained from the nucleotide or amino acid sequences disclosed herein.

According to the present invention, the proteins to be used as immunizing antigens may be a complete protein or a partial peptide of the proteins. A partial peptide may comprise, for example, the amino (N)-terminal or carboxy (C)-terminal fragment of proteins of the present invention. Herein, an antibody is defined as a protein that reacts with either the whole proteins of the present invention, or a fragment of the proteins.

Genes encoding proteins of the present invention or their fragment may be inserted into a known expression vector, which is then used to transform a host cell as described herein. The desired protein or its fragment may be recovered from the outside or inside of host cells by any standard method, and may subsequently be used as an antigen. Alternatively, cells expressing the protein or their lysates, or a chemically synthesized protein may be used as antigen. In the case of a short peptide, it is preferably bound to an appropriate carrier protein such as keyhole limpet hemocyanin, bovine serum albumin, and ovalbumin before using as antigen.

Any mammalian animal may be immunized with the antigen, but preferably, the compatibility with parental cells used for cell fusion is taken into account. In general, animals of Rodentia, Lagomorpha, or Primates are used.

Animals of Rodentia include, for example, mice, rats, and hamsters. Animals of Lagomorpha include, for example, rabbits. Animals of Primates include, for example, monkeys of Catarrhini (old world monkeys) such as *Macaca fascicularis*, rhesus monkeys, sacred baboons, and chimpanzees.

Methods for immunizing animals with antigens are known in the art. Intraperitoneal injection or subcutaneous injection of antigens is a standard method of immunization for mammals. More specifically, antigens may be diluted and suspended in an appropriate amount of phosphate buffered saline (PBS), saline, etc. If desired, the antigen suspension may be mixed with an appropriate amount of a standard adjuvant such as Freund's complete adjuvant, made into an emulsion, and then administered to mammalian animals. Preferably, this is followed by several administrations of antigen mixed with an appropriately amount of Freund's incomplete adjuvant every 4 to 21 days. An appropriate carrier may also be used for immunization. After immunizing as above, serum is examined by a standard method for an increase in the amount of desired antibodies.

Polyclonal antibodies against the proteins of the present invention may be prepared by collecting blood from the immunized mammal after verifying an increase of desired antibodies in the serum, and by separating serum from the blood by any conventional method. Polyclonal antibodies include serum containing polyclonal antibodies, as well as fractions containing the polyclonal antibodies isolated from the serum. Immunoglobulin G or M can be prepared from a fraction which recognizes only the proteins of the present invention using, for example, an affinity column coupled with proteins of the present invention, and further purifying this fraction using a protein A or protein G column.

To prepare monoclonal antibodies, immunocytes are collected from the mammal immunized with the antigen and checked for an increase in the level of desired antibodies in the serum as described above, and are subjected to cell fusion. The immune cells used for cell fusion are preferably obtained from the spleen. Other preferred parental cells to be fused with the above immunocytes include, for example, mammalian myeloma cells, and more preferably myeloma cells having an acquired property for the selection of fused cells by drugs.

The above immunocytes and myeloma cells can be fused according to known methods, for example, the method of Milstein et al. (Galfre, G. and Milstein, C., Methods Enzymol. (1981) 73, 3-46).

Resulting hybridomas obtained by the cell fusion may be selected by cultivating them in a standard selection medium such as the HAT medium (hypoxanthine, aminopterin, and thymidine containing medium). The cell culture is typically continued in the HAT medium for several days to several weeks, which is sufficient to allow all the other cells, with the exception of the desired hybridoma (non-fused cells), to die. Then, standard limiting dilution is performed to screen and clone a hybridoma producing the desired antibody.

In addition to the above method in which a non-human animal is immunized with an antigen for preparing a hybridoma, a hybridoma producing a desired human antibody that is able to bind to a protein can be obtained by the following method. First, human lymphocytes such as those infected by the EB virus may be immunized with a protein, protein expressing cells, or their lysates in vitro. Then, the immunized lymphocytes are fused with human-derived myeloma cells that are capable of indefinite division, such as U266, to yield the desired hybridoma (Unexamined Published Japanese Patent Application No. (JP-A) Sho 63-17688).

The obtained hybridomas are subsequently transplanted into the abdominal cavity of a mouse and the ascites are harvested. The obtained monoclonal antibodies can be purified by, for example, ammonium sulfate precipitation, a protein A or protein G column, DEAE ion exchange chromatography, or an affinity column to which proteins of the present invention are coupled. The antibodies of the present invention can be used not only for purification and detection of the proteins of the present invention, but also as candidates for agonists and antagonists of the proteins. In addition, these antibodies can be applied to the antibody treatment for diseases related to the proteins of the present invention. When an obtained antibody is to be administered to the human body (antibody treatment), a human antibody or a humanized antibody is preferable to reduce immunogenicity.

For example, transgenic animals having a repertoire of human antibody genes may be immunized with an antigen selected from a protein, cells expressing the protein or their lysates. Antibody producing cells are then collected from the animals and fused with myeloma cells to obtain hybridomas, from which human antibodies against the protein can be prepared (see WO92-03918, WO93-2227, WO94-02602, WO94-25585, WO96-33735, and WO96-34096).

Alternatively, an immunocyte that produces antibodies, such as an immunized lymphocyte, may be immortalized by an oncogene and used for preparing monoclonal antibodies.

Monoclonal antibodies thus obtained can also be recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). A DNA encoding an antibody may be cloned from an immunocyte, such as a hybridoma or an immunized lymphocyte producing the antibody, inserted into an appropriate vector, and introduced into host cells to prepare a recombinant antibody. The present invention also provides recombinant antibodies prepared as described above.

Furthermore, antibodies of the present invention may be fragments of antibodies or modified antibodies, so long as they bind to one or more of the proteins of the invention. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The term "antibodies" of the present invention also comprises such modified antibodies. The modified antibody can be obtained by chemically modifying an antibody. These modification methods are conventional in the field.

Alternatively, antibodies of the present invention may be obtained as chimeric antibodies between a variable region derived from a nonhuman antibody and a constant region derived from a human antibody. It can also be obtained as a humanized antibody comprising a complementarity-determining region (CDR) derived from a nonhuman antibody, a frame work region (FR) and a constant region derived from a human antibody. Such antibodies can be prepared using a known technology.

Antibodies obtained as above may be purified to homogeneity. For example, the separation and purification of the antibody can be performed according to separation and purification methods used for general proteins. For example, the antibody may be separated and isolated by appropriately selecting and combining column chromatographies such as affinity chromatography, filteration, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but the chromatographies are not limited thereto. The concentration of the thus obtained antibodies can be determined by measuring the absorbance, by an enzyme-linked immunosorbent assay (ELISA), and such.

A protein A column or protein G column can be used as the affinity column. Examples of protein A columns include, for example, Hyper D, POROS, and Sepharose F. F. (Pharmacia).

Examples of chromatographies other than affinity chromatography includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographies can be carried out by a liquid-phase chromatography, such as HPLC, FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of antibodies of the invention. In ELISA, antibodies of the present invention are immobilized on a plate, proteins of the present invention are applied to the plate, and then samples containing a desired antibody, such as culture supernatants of antibody producing cells or purified antibodies, are applied. Then, a secondary antibody that recognizes the primary antibody and is labeled with an enzyme such as alkaline phosphatase is applied, and the plate is incubated. Next, after washing, an enzyme substrate such as p-nitrophenyl phosphate is added to the plate, and the absorbance is measured to evaluate the antigen binding activity of the sample. A fragment of the protein, such as a C-terminal fragment may be used as the protein. BIAcore (Pharmacia) may be used to evaluate the activity of antibodies according to the present invention.

These methods allow the detection or measurement of proteins of the present invention by exposing antibodies of the present invention to samples assumed to contain the proteins of the present invention, and detecting or measuring the immune complexes formed by the antibodies and the proteins. Because the methods for detecting or measuring the proteins according to the present invention can specifically detect or measure proteins, the methods may be useful in a variety of experiments in which the proteins of the present invention are used.

Furthermore, the present invention provides DNAs comprising at least 15 nucleotides, which is complementary to DNAs (comprising, for example, the nucleotide sequence according to SEQ ID NO: 1, 3, or 5) of the present invention or a complementary strand thereof.

Herein, "complementary strand" means a strand that is opposite relative to the other strand in a double-stranded nucleic acid composed of A:T (U in the case of RNA) and G:C base pairs. In addition, being "complementary" is not limited to having complete complementarity in a continuous region of at least 15 nucleotides, but it can also mean having a homology of at least 70%, preferably at least 80%, more preferably 90%, and most preferably 95% or higher at the nucleotide level. Homology can be determined using the algorithm described herein.

Such nucleic acids include: probes or primers used for detecting or amplifying DNAs encoding proteins of this invention; probes or primers used for detecting DNA expression; or nucleotides or nucleotide derivatives (for example, antisense oligonucleotides or ribozymes, or DNA encoding them) used for regulating the expression of proteins of this invention. Such nucleic acids may also be useful for preparing DNA chips.

When using as a primer, the 3'-region can be made complementary and a recognition site for a restriction enzyme, or a tag can be attached to the 5'-region.

The present invention also provides diagnostic reagents for diseases associated with abnormalities in the expression of the genes encoding the proteins of the present invention or abnormalities in the activity (function) of the proteins of the present invention.

In one embodiment, the diagnostic reagents comprise a DNA that comprises at least 15 nucleotides and hybridizes to a DNA encoding a protein of the present invention as described above or to a DNA comprising the expression regulatory region. The DNA can be used as: a probe for detecting a gene encoding a protein of the present invention or a DNA comprising its expression regulatory region; or a primer for amplifying a gene encoding a protein of the present invention or its expression regulatory region in the diagnostic methods of the present invention described above. DNAs of the present invention can be prepared, for example, using commercially available DNA synthesizers. The probe can also be prepared as a double-stranded DNA fragment obtained by restriction enzyme treatment or such. When the DNAs of the present invention are used as probes, they are preferably used after being appropriately labeled. The labeling methods include, for example, those that comprise phosphorylating the 5' end of DNAs with $^{32}$P using T4 polynucleotide kinase and methods (random priming method and such) that comprise the step of incorporating substrate nucleotides labeled with isotopes such as $^{32}$P, fluorescent dye, biotin, or such using DNA polymerase such as Klenow enzyme, and as a primer random hexamer oligonucleotide or such.

In an alternative embodiment, the diagnostic reagents of the present invention comprise the antibodies described below that bind to the proteins of the present invention. The antibodies are used to detect the proteins of the present invention in the above-described diagnostic methods of the present invention. There is no limitation on the type of the antibodies, as long as they can detect the proteins of the present invention. The diagnostic antibodies include polyclonal and monoclonal antibodies. The antibodies may be labeled if required.

The diagnostic reagents described above may comprise, in addition to a DNA or an antibody which is an active ingredient, for example, sterilized water, saline, vegetable oil, detergent, lipid, solubilizing agent, buffering agent, protein stabilizing agent (such as BSA and gelatin), and preservative, if required.

The receptor proteins of the present invention are also useful in identifying their ligands, agonists, and antagonists. The present invention provides (screening) methods for identifying ligands, agonists, and antagonists for the proteins of the present invention using the proteins.

In a preferred embodiment of a method of the present invention for identifying ligands, first, candidate compounds (test samples) are contacted with a protein of the present invention or cells expressing the protein; and second, whether the candidate compounds bind to the protein of the present invention or cells expressing the protein is determined (the binding activity is evaluated). Then, compounds having binding activity are selected as ligands.

Proteins of the present invention used for the identification (screening) methods of the present invention may be recombinant proteins or naturally occurring proteins. They may also be partial peptides. They can be expressed on the cell surface, or contained in the membrane fraction. A candidate compound is not limited to any particular sample; it can be, for example, a cell extract, a cell culture supernatant, a product of a fermentation microorganism, a marine organism extract, a plant extract, a purified or crude protein, a peptide, a non-peptide compound, a synthetic low molecular weight compound, or a natural compound. The proteins of this invention can be contacted with the candidate compound (test sample) as a purified protein, soluble protein, in a form bound to a carrier, as a fusion protein with another protein, in a form expressed on the cell surface, or as a form contained in the membrane fraction.

As methods of screening for proteins that, for example, bind to proteins of the present invention using proteins of the present invention, many methods well known to those skilled in the art can be used. Such a screening can be conducted by, for example, the immunoprecipitation method, specifically, in the following manner. Genes encoding proteins of the present invention are expressed in animal cells or such, by inserting the gene into a foreign gene expression vector, such as pSV2neo, pcDNA I, and pCD8. The promoters to be used for the expression are not limited as long as they are promoters generally used and include, for example, the SV40 early promoter (Rigby in Williamson (ed.), Genetic Engineering, vol. 3. Academic Press, London, p. 83-141 (1982)), the EF-1α promoter (Kim et al., Gene 91, p217-223 (1990)), the CAG promoter (Niwa et al. Gene 108, p. 193-200 (1991)), the RSV LTR promoter (Cullen Methods in Enzymology 152, p. 684-704 (1987)) the SRα promoter (Takebe et al., Mol. Cell. Biol. 8, p. 466 (1988), the CMV immediate early promoter (Seed and Aruffo Proc. Natl. Acad. Sci. USA 84, p. 3365-3369 (1987)), the SV40 late promoter (Gheysen and Fiers J. Mol. Appl. Genet. 1, p. 385-394 (1982)), the Adenovirus late promoter (Kaufman et al., Mol. Cell. Biol. 9, p. 946 (1989)), the HSV TK promoter, and such.

The introduction of the gene into animal cells to express a foreign gene can be performed according to any method, for example, the electroporation method (Chu G. et al. Nucl.

Acids Res. 15, 1311-1326 (1987)), the calcium phosphate method (Chen, C and Okayama, H. Mol. Cell. Biol. 7, 2745-2752 (1987)), the DEAE dextran method (Lopata, M. A. et al. Nucl. Acids Res. 12, 5707-5717 (1984)), Sussman, D. J. and Milman, G Mol. Cell. Biol. 4, 1642-1643 (1985)), the Lipofectin method (Derijard, B. Cell 7, 1025-1037 (1994); Lamb, B. T. et al. Nature Genetics 5, 22-30 (1993): Rabindran, S. K. et al. Science 259, 230-234 (1993)), and such.

Proteins of the present invention can be expressed as fusion proteins comprising a recognition site (epitope) of a monoclonal antibody by introducing, to the N- or C-terminus of the protein, an epitope of a monoclonal antibody whose specificity has been revealed. A commercially available epitope-antibody system can be used (Experimental Medicine 13, 85-90 (1995)). Vectors that can express a fusion protein with, for example, β-galactosidase, maltose-binding protein, glutathione S-transferase, green florescence protein (GFP) and such through multiple cloning sites are commercially available.

Method for preparing a fusion protein by introducing only a small epitope portion consisting of several to a dozen amino acids so as to not change, as much as possible, the property of the proteins of the present invention by the fusion, have also been reported. Epitopes, such as polyhistidine (His-tag), influenza aggregate HA, human c-myc, FLAG, Vesicular stomatitis virus glycoprotein (VSV-GP), T7 gene 10 protein (T7-tag), human herpes simplex virus glycoprotein (HSV-tag), E-tag (an epitope on monoclonal phage), and such, and monoclonal antibodies recognizing them can be used as epitope-antibody systems for screening proteins binding to the proteins of the present invention (Experimental Medicine 13, 85-90 (1995)).

In immunoprecipitation, an immune complex is formed by adding these antibodies to a cell lysate prepared by using an appropriate detergent. The immune complex consists of a protein of the present invention, a protein that can bind to the protein, and an antibody. Immunoprecipitation can also be conducted by using antibodies against proteins of the present invention, besides using antibodies against the above epitopes. Antibodies against proteins of the present invention can be prepared, for example, by introducing a gene encoding the proteins into an appropriate $E.\ coli$ expression vector, expressing the gene in $E.\ coli$, purifying the expressed protein, and immunizing rabbits, mice, rats, goats, chicken and such with the protein. The antibodies can also be prepared by immunizing animals of above with synthesized partial peptides of the proteins of the present invention.

An immune complex can be precipitated, for example by Protein A Sepharose or Protein G sepharose when the antibody is a mouse IgG antibody. If the proteins of the present invention are prepared as fusion proteins with an epitope such as GST, an immune complex can be formed in the same manner as when using the antibody against a protein of the present invention, by using a substance that specifically binds to the epitope, such as glutathione-Sepharose 4B.

Immunoprecipitation can be performed by following or according to, for example, methods in literature (Harlow, E. and Lane, D.: Antibodies pp. 511-552, Cold Spring Harbor Laboratory publications, New York (1988)).

SDS-PAGE is commonly used for analyzing immunoprecipitated proteins. The bound protein can be analyzed by the molecular weight of the protein using a gel with an appropriate concentration. Since the protein bound to proteins of the present invention is difficult to detect by a common staining method such as Coomassie staining or silver staining, the detection sensitivity of the protein can be improved by culturing cells in a culture medium containing the radioactive isotope $^{35}$S-methionine or $^{35}$S-cystein, labeling proteins within the cells, and detecting the proteins. Once the molecular weight of the protein has been revealed, the target protein can be purified directly from the SDS-polyacrylamide gel and its sequence can be determined.

In addition, as a method for isolating a protein capable of binding to the protein using a protein of this invention, western blotting may be used (Skolnik E. Y. et al. Cell 65: 83-90 (1991)). Specifically, a cDNA library using a phage vector (λgt11, ZAP, and the like) can be prepared using a cell, tissue, or organ expected to express a protein capable of binding to a protein of this invention (for example, NK cells). The cDNA library can be expressed on LB-agarose, and then the expressed protein can be immobilized onto a filter. Then, a purified and labeled protein of this invention can be incubated with the above filter. Finally, a plaque expressing a protein capable of binding to the protein of this invention can be detected by the label. For labeling a protein of this invention, methods that make use of: the binding between biotin and avidin; an antibody specifically binding the protein of this invention, or a peptide or polypeptide fused to the protein (for example, GST); radioisotopes; or fluorescence, or the like, can be used.

In another embodiment of the above-described identification (screening) methods of this invention, the two-hybrid system using cells may be used (Fields S. and Sternglanz R. Trends Genet. 10: 286-292 (1994); Dalton S. and Treisman R. Characterization of SAP-1, a protein recruited by serum response factor to the c-fos serum response element. Cell 68: 597-612 (1992); "MATCHMAKER Two-Hybrid System"; "Mammalian MATCHMAKER Two-Hybrid Assay Kit"; "MATCHMAKER One-Hybrid System" (all from Clontech); and "HybriZAP Two-Hybrid Vector System" (Stratagene)). In the two-hybrid system, proteins of this invention or a partial peptide may be expressed in yeast cells as a fusion protein with the SRF DNA binding domain, or GAL4 DNA binding domain. A cDNA library in which the protein is expressed as a fusion between the VP16 or GAL4 transcription activation domain is prepared from cells in which a protein capable of binding to proteins of this invention is expected to be present. The library is transfected into yeast cells, and cDNA derived from the library is isolated from a positive clone detected (when a protein capable of binding to the proteins of this invention is expressed in yeast cells, binding of the two proteins activates a reporter gene, which is used to detect a positive clone). Isolated cDNA may be introduced and expressed in $E.\ coli$ to obtain a protein encoded by the cDNA. The reporter gene used in the two-hybrid system may be, for example, a gene such as HIS3, Ade2, LacZ, CAT, luciferase, and PAI-1 (plasminogen activator inhibitor type I), but is not limited thereto. Such a screening using the two-hybrid system may be performed using a mammalian cell other than yeast.

Candidate compounds binding to proteins of the present invention can be screened using affinity chromatography. For example, the proteins of the present invention may be immobilized on a carrier of an affinity column, and a candidate compound presumed to express a protein capable of binding to the proteins of the invention, is applied to the column. Herein, candidate compounds may be, for example, cell extracts, cell lysates, etc. After loading the candidate compound, the column is washed, and proteins bound to the proteins of the present invention can be prepared.

The amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a means for detecting or quantifying the bound candidate compound in the present invention. When such a biosensor is used, the interaction between the proteins of the present invention and a candidate compound can be observed real-time as a surface plasmon resonance signal, using only a minute amount of protein and without labeling (for example, BIAcore, Pharmacia). Therefore, it is possible to evaluate the binding between the proteins of the present invention and a candidate compound using a biosensor such as BIAcore.

Ligands that can be identified by the above-described methods of the present invention are also included in the present invention.

In a preferred embodiment, a method for identifying agonists for a protein of the present invention comprises the steps of: first, contacting candidate compounds with cells expressing the protein of the present invention; and determining whether the candidate compounds generate a signal that is an indicator of activation of the protein of the present invention. Specifically, the method comprise the steps of incubating candidate compounds with a receptor protein of the present invention; and determining whether the candidate compounds are agonists using as an indicator the presence or absence of a signal generated by the protein of the present invention in response to agonist stimulation.

The present inventors found that immunosuppression was induced by the signal generated by the receptor proteins of the present invention. Thus, the presence or absence of the signal in the present invention can be detected, for example, by determining whether the immunosuppression is induced. An example study is, inducing experimental autoimmune encephalomyelitis (EAE) using a humanized model mouse where the human immune system had been reconstituted (note: mouse and human immune systems are not usually compatible) by transplanting human hematopoietic stem cells into immunodeficient mice (Hiramatsu H, Nishikomori R, Heike T, Ito M, Kobayashi K, Katamura K, and Nakahata T, Blood (2003), 102, 873-880), and then administering candidate agonist substances to such mice to evaluate them for EAE (quantitation of hind leg paralysis, urinary incontinence, and weight loss). When the above-described signal is detected by a method described above, the candidate compound is evaluated to be an agonist. Such agonists that can be identified by the above-described methods are also included in the present invention.

The present invention also provides immunosuppressants comprising an agonist of a protein of the present invention, as an active ingredient. The immunosuppressants of the present invention are expected to be effective in the treatment of, for example, allergic diseases (for example, allergic asthma) and autoimmune diseases. Thus, the present invention provides therapeutic agents for allergic or autoimmune diseases, which comprise an agonist for the proteins of the present invention, as an active ingredient.

In a preferred embodiment, the methods for identifying antagonists for the proteins of the present invention comprise the steps of: first contacting candidate compound(s) with cells expressing a protein of the present invention; and second determining whether the signal which is an indicator of activation of the protein of the present invention is reduced compared to when the candidate compound(s) is absent.

It is thought that, for example, an immunopotentiation effect (such as antiviral or anti-tumor activity) is induced as a result of a reduction (suppression) of the signal generated by a receptor protein of the present invention. Thus, whether the above-described signal of the present invention is reduced can be determined, for example, by detecting the enhanced immunopotentiation effect. Examples include: an in-vitro study where the cytotoxicity against cells (for example, NK sensitive cell lines such as K-562 cell line) targeted by NK cells is determined and compared in the presence or absence of antagonist candidate substances; and an in-vivo study where human cells infected with viruses or human cancer tissues are transplanted into the above-described humanized model mice comprising the reconstructed human immune system, antagonist candidate substances are administered to the mice, and then cytotoxicity against the human cells infected with viruses or cancer tissues transplanted into the mice is evaluated.

When the above-described signal is found to be decreased in the methods as described above, the candidate compound is determined to be an antagonist. Such antagonists that can be identified by the above-described methods are also included in the present invention.

The present invention also provides immunopotentiators comprising an agonist for a protein of the present invention, as an active ingredient. The immunopotentiators of the present invention are expected to be, for example, effective anti-tumor or antiviral agents. Thus, the present invention provides anti-tumor agents and antiviral agents that comprise an agonist for a protein of the present invention, as an active ingredient.

The methods of screening for molecules that bind when an immobilized protein of the present invention is exposed to synthetic chemical compounds, or natural substance banks, or a random phage peptide display library, or the methods of screening using high-throughput based on combinatorial chemistry techniques (Wrighton Nc, Farrel F X, Chang R, Kashyap A K, Barbone F P, Mulcahy L S, Johnson D L, Barret R W, Jolliffe L K, Dower W J; Small peptides as potent mimetics of the protein hormone erythropoietin, Science (UNITED STATES) Jul. 26, 1996, 273 p458-64, Verdine G L., The combinatorial chemistry of nature. Nature (ENGLAND) Nov. 7, 1996, 384, p11-13, Hogan J C Jr., Directed combinatorial chemistry. Nature (ENGLAND) Nov. 7, 1996, 384 p17-9) to isolate proteins such as agonists and antagonists that bind to proteins of the present invention are well known to those skilled in the art.

The present invention also provides kits to be used in the identification (screening) methods as described above. The kits comprise a protein of the present invention or cells expressing a protein of the present invention. The kits may comprise candidate compounds for a ligand, agonist, or antagonist for NKIR protein.

When administrating a protein of this invention, a compounds isolated by a identification (screening) method of the present invention, or a pharmaceutical agent as a pharmaceutical for humans and other mammals such as mice, rats, guinea-pigs, rabbits, chicken, cats, dogs, sheep, pigs, cattle, monkeys, baboons and chimpanzees, the protein or the isolated compound can be directly administered or formulated into a dosage form using a known pharmaceutical preparation method. For example, according to the need, the pharmaceutical can be taken orally, as a sugar-coated tablet, capsule, elixir or microcapsule, or non-orally, in the form of an injection of a sterile solution or suspension with water or any other pharmaceutically acceptable liquid. For example, the compounds can be mixed with pharmacologically acceptable carriers or medium, specifically, sterilized water, saline, plant oils, emulsifiers, suspending agents, surfactants, stabilizers, flavoring agents, excipients, vehicles, preservatives, binders and such, in a unit dose form required for generally accepted drug implementation. The amount of active ingredient in these preparations facilitates the acquisition of a suitable dosage within the indicated range.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier such as oil can also be included in the above ingredients. Sterile composites for injections can be formulated following normal drug implementations using vehicles such as distilled water used for injections.

Saline, glucose, and other isotonic liquids including adjuvants such as D-sorbitol, D-mannnose, D-mannitol, and sodium chloride, can be used as aqueous solutions for injections. These can be used in conjunction with suitable solubilizers such as alcohol, specifically ethanol, polyalcohols such as propylene glycol and polyethylene glycol, and non-ionic surfactants such as Polysorbate 80 (TM) and HCO-50.

Sesame oil or Soy-bean oil can be used as a oleaginous liquid and may be used in conjunction with benzyl benzoate or benzyl alcohol as a solubilizer and may be formulated with a buffer such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to those skilled in the art may be used to administer the inventive pharmaceutical to patients, for example as intraarterial, intravenous, percutaneous injections and also as intranasal, transbronchial, intramuscular, percutaneous, or oral administrations. The dosage and method of administration vary according to the body weight and age of the patient and the administration method; however, these can be routinely selected by one skilled in the art. If said compound is encodable by a DNA, the DNA can be inserted into a vector for gene therapy and the vector administered to perform the therapy. The dosage and method of administration vary according to the body weight, age, and symptoms of the patient, but one skilled in the art can select them suitably.

The dose per time of a protein of this invention may vary depending on the type of recipient, target organ, disease condition, and administration method. For example, when injecting into a normal adult (body weight: 60 kg), it may be administered at about 100 µg to 20 mg per day.

The dose of a compound that binds to a protein of this invention, or that of a compound that regulates the activity of a protein of this invention varies depending on the type of disease. For example, the compound may be administered orally into a normal adult (body weight: 60 kg) at about 0.1 to 100 mg per day, preferably at about 1.0 to 50 mg per day, and more preferably at about 1.0 to 20 mg per day.

When administered parenterally, the dose per time may vary depending on the recipient, target organ, disease condition, and administration method. For example, an appropriate dose can be, as an intravenous injection into a normal adult (body weight: 60 kg), usually about 0.01 to 30 mg per day, preferably about 0.1 to 20 mg per day, and more preferably about 0.1 to 10 mg per day. For other animals, an amount converted to dose per 60 kg body weight, or dose per body surface area may be applied.

All prior-art documents cited herein are incorporated herein by reference.

EXAMPLES

Hereinbelow, the present invention is specifically described using Examples, but it is not to be construed as being limited thereto.

Example 1

Cloning of Full-Length Sequence

The present inventors found sequence tags for unidentified genes specific to NK cells (Table 1) among serial analysis of gene-expression (SAGE) data for immune cells disclosed at http://www.prevent.m.u-tokyo.ac.jp, and also discovered that the tags were present in the sequence AX191619 in the International publication (WO 0149728). Table 1 shows selective expression of the sequence tag (TGCCGCATAA) in an NK cell-derived library.

TABLE 1

|  | TGCCGCATAA | Total numbers of analyzed tags |
|---|---|---|
| Premature dendritic cells | 0 | 50795 |
| GM-CSF-induced macrophages | 0 | 50041 |
| LPS-stimulated monocytes | 0 | 30885 |
| Mature dendritic cells | 0 | 27602 |
| M-CSF-induced macrophages | 0 | 46833 |
| Monocytes | 0 | 51228 |
| Langerhans-like cells | 0 | 44873 |
| CD4 T cells (naive) | 0 | 41789 |
| CD4 T cells (memory, CCR4 negative) | 0 | 27733 |
| CD4 T cells (memory, CCR4 positive) | 0 | 25415 |
| Granulocytes | 0 | 23608 |
| Activated T cells (TH1) | 0 | 26498 |
| Activated T cells (TH2) | 0 | 25371 |
| NK cells | 6 | 29878 |

Primers SA1 (5'-TTGAATTCACACACCCACAGGAC-CTGCAGCTGAA-3'/SEQ ID NO: 7), and SA2 (5'-TTG-GATCCACTGAAGGACCCACAGAAAGAGTTGA-3'/ SEQ ID NO: 8) were designed based on the data described above to amplify the entire coding region, and the gene was cloned by PCR from a cDNA library derived from human spleen. The nucleotide sequence of the yielded clone is shown in SEQ ID NO: 1, and the amino acid sequence of the protein encoded by the nucleotide sequence is shown in SEQ ID NO: 2. The procedures are specifically described below.

(1) Construction of pGEMTE_NK1

PCR was carried out under the following reaction conditions.

Template: marathon-ready cDNA human spleen (CLONTECH)
Primers: SA1<=>SA2
Reaction Condition:
96° C. for 1 minute;
5 cycles of 96° C. for 30 seconds and 72° C. for 4 minutes;
5 cycles of 96° C. for 30 seconds and 70° C. for 4 minutes; and
25 cycles of 96° C. for 20 seconds and 68° C. for 4 minutes.

PCR was carried out using TaKaRa Ex Taq (buffer and dNTP mixture were supplied with the kit). A band of about 1.5 kb band was excised after agarose gel electrophoresis. After purification with QIAquick Gel Extraction Kit, the PCR product was inserted into pGEM T-Easy Vector to construct pGEMTE_NK1. The nucleotide sequence was confirmed using the primers SA1 to 7, T7, and SP6.

```
SA3:    5'-ACCCTGAGATGTCAGACAAAG-3'/SEQ ID NO: 9

SA4:    5'-GCCACCTCACACCAGTAAAG-3'/SEQ ID NO: 10

SA5:    5'-CCTCCGATCCTGTATTCCTTC-3'/SEQ ID NO: 11

SA6:    5'-TGGAGCTGTGGGTGGTATCTG-3'/SEQ ID NO: 12

SA7:    5'-AGAACCTCAAAGAGGAGTGAA-3'/SEQ ID NO: 13

T7      5'-ATTATGCTGAGTGATATCCC-3'/SEQ ID NO: 14
promoter
primer:

SP6     5'-ATTAGGTGACACTATAGAA-3'/SEQ ID NO: 15
promoter
primer:
```

(2) Construction of pCOS_NK1 pGEMTE-NK1 was digested with EcoRI and BamHI and subjected to agarose gel electrophoresis. The resulting band of about 1.5 kb was then excised. After purification with QIAquick Gel Extraction Kit, the DNA fragment was inserted between EcoRI and BamHI sites of pCOS1 to yield pCOS-NK1.

(3) Construction of pCHO2-NK1-FLAG

PCR was carried out under the following reaction conditions.

Template: pGEMTE-NK1

```
Primers:
SAS1 (5'-GGGAATTCATGTTGCCATCTTTAGTTCC-3'/
SEQ ID NO: 16)<=>SAS2 (5'-AAGGATCCACTC-
CTCTCTCTGGAG
AC-3'/SEQ ID NO: 17)
```

Reaction Conditions:

94° C. for 2 minutes; and 25 cycles of 94° C. for 15 seconds, 55° C. for 30 seconds, and 68° C. for 1 minute.

PCR was carried out using KOD plus (TOYOBO; buffer, dNTPs, and MgSO$_4$ were attached thereto). After purification with QIAquick PCR Purification Kit (QIAGEN), the PCR product was digested with EcoRI and BamHI and subjected to agarose gel electrophoresis, and then a band of about 1 kb was excised from the gel. After purification with QIAquick Gel Extraction Kit, the DNA fragment was inserted between EcoRI and BamHI sites of pCHO2-FLAG to yield pCHO2-NK1-FLAG. The nucleotide sequence was confirmed using the primers SAS1, SAS2, S3, S4, S5, EF1α, and polyA.

```
EF1α:  5'-GCCTCAGACAGTGGTTCAAA-3'/SEQ ID NO: 18

IgG1 polyA: 5'-AGAACCATCACAGTCTCGCA-3'/
SEQ ID NO: 19
```

(4) Construction of pCHO2-SGNK1-FLAG

PCR was carried out under the following reaction conditions.

A:

Template: pCOS2-SGhMPL-FLAG

```
Primers:
Hmp1-sig1 (5'-AAGAATTCCACCATGGCTGGACCTGCCAC-3'/
SEQ ID NO: 20)<=>NK1-sig2 (5'-ACAGGGTTTGGCCAGGCTTG
GGCTTCCTGCACTGTCCAGAG-3'/SEQ ID NO: 21)
```

B:

Template: pGEMTE-NK1

```
Primers:
NK1-sig1 (5'-GCAGGAAGCCCAAGCCTGGCCAAACCCTGT-3'/
SEQ ID NO: 22)<=>SAS2
```

C:

Template: Mixture of products of reaction series A and B

Primers: Hmp1-sig1<=>SAS2

Reaction Condition:

94° C. for 2 minutes; and 25 cycles of 94° C. for 15 seconds, 55° C. for 30 seconds, and 68° C. for 1 minute.

PCR was carried out using KOD plus (TOYOBO; buffer, dNTPs, and MgSO$_4$ were attached thereto). After the PCR product of reaction series C was purified with QIAquick PCR Purification Kit (QIAGEN), it was digested with EcoRI and BamHI, and subjected to agarose gel electrophoresis. A band of about 0.9 kb was excised from the gel. After purification with QIAquick Gel Extraction Kit, the DNA fragment was inserted between EcoRI and BamHI sites of pCHO2-FLAG to yield pCHO2-SGNK1-FLAG. The nucleotide sequence was confirmed using the primers, NK1-sig1, NK1-sig2, SAS2, S3, S4, S5, EF1α, and polyA.

The nucleotide sequences of the clones obtained through steps (1) to (4) as described above were presumed to encode a putative transmembrane protein consisting of 429 amino acids. This sequence was compared with the sequence (WO 01/49728) determined by the Sagami Chemical Research Center. The result showed that the central portion of the sequence is identical to the Sagami sequence, but the N-terminal sequences are different. Sequences variations are also found between the proteins encoded. All clones obtained above share the C-terminal sequence, but some clones were deduced to be splicing variants based on the 5'-end sequence. Thus, to determine the original sequence, 5' RACE was carried out by the following procedure.

RNA (0.4 μg/μl, 20 μl in DEPC-DDW) was extracted from NK cells using RNA-Bee_RNA ISOLATION REAGENT (Tel-Test). cDNA (5'-RACE-Ready cDNA, 100 μl in Tricine-EDTA Buffer) was synthesized from 1 μg of the RNA using SMART RACE cDNA Amplification Kit (CLONTECH). 5'-RACE PCR was carried out under the following reaction conditions:

1st Round:

Template: 2.5 μl of 5'-RACE-Ready cDNA

Primers: 10× Universal Primer A Mix (attached; used at 1×)<=>SAS2

10× Universal Primer A Mix:

(long, 0.4 μM:

```
(long, 0.4 μM: 5'-CTAATACGACTCACTATAGGGCAAGCAGTGGT
ATCAACGCAGAGT-3'/SEQ ID NO: 23)

(short, 2 μM: 5'-CTAATACGACTCACTATAGGGC-3'/
SEQ ID NO: 24)
```

2nd Round:

Template: 5 μl of 1st round PCR product

Primers: Nested Universal Primer A (NUP) (5'-AAG-CAGTGGTATCAACGCAGAGT-3'/SEQ ID NO: 25)<=>SA4

Reaction Conditions:
94° C. for 30 seconds;
5 cycles of 94° C. for 5 seconds and 72° C. for 3 minutes;
5 cycles of 94° C. for 5 seconds, 70° C. for 10 seconds, and 72° C. for 3 minutes;
30 cycles of 94° C. for 5 seconds, 68° C. for 10 seconds, and 72° C. for 3 minutes; and
72° C. for 7 minutes.

The 2nd round PCR product was electrophoresed in an agarose gel, and a band of about 650 bp was excised. After purification with QIAquick Gel Extraction Kit, the resulting fragment was inserted into pGEM T-Easy Vector. The nucleotide sequence was determined using the primers SA3, 4, T7, SP6, and NUP.

The result showed that all coding sequences of the 5 clones whose sequences were verified were identical to the nucleotide sequence described above (of these, one clone was found to be shorter at the 5' end). Thus, it is safe to conclude that the yielded clone described above is identical to the nucleotide sequence truly expressed.

Motif searches using Prosite, Pfam, Psort, and the like, revealed the following sequence features:
N-glycosylation sites: (N[^P][ST][^P]) 60, NQTL; 245, NHSA; and 268, NYSC ITIM motifs (Yxx[VL]): 351, YANV; and 366, YSVV
Ig-like domains: 27-80; 120-177; and 216-273
Transmembrane domain: 309-325

Based on the above-described sequence information, the isolated gene as described above was inferred to be a member of suppressive receptors (KIR) that recognize, as a ligand, classic MHC class I belonging to the FcR superfamily. Since this gene is expressed specifically in NK cells, hereinafter it is called the NKIR gene.

Example 2

Detection of NKIR Protein Using Rabbit Polyclonal Antibody

An *E. coli* expression system was constructed, and a fusion protein comprising the NKIR extracellular domain was expressed and purified (FIG. 1). The procedure is described below in detail.

(1) Construction of *E. coli* Expression Plasmid pET32a-NK-sol for NKIR Fusion Protein PCR was carried out under the following reaction conditions.
Template: pGEMTE-NK1

```
Primers:
NKfusion (5'-CTCGGATCCTTGCCATCTTTAGTTCCCTGTGTT-3'/
SEQ ID NO: 26)<=>NKr2 (5'-GCTGTCGACTTAGTTGCTGGCGGG
AGTGAACAAGAC-3'/SEQ ID NO: 27)
```

Reaction Conditions:
94° C. for 2 minutes; and
25 cycles of 94° C. for 20 seconds, 60° C. for 30 seconds, and 68° C. for 2 minutes.

PCR was carried out using KOD plus (TOYOBO; buffer, dNTPs, and MgSO₄ were also supplied with the kit). After purification with MicroSpin S-300 HR column (Amersham Biosciences), the PCR product was digested with BamHI and SalI, and subjected to agarose gel electrophoresis. A band of about 0.9 kb was excised from the gel. After purification with a MicroSpin S-300 HR column, the fragment was inserted between BamHI and SalI sites of pET-32(a) (Novagen) to yield pET32a-NK-sol.

(2) Construction of Animal Cell Expression Plasmid pCOS2-NK-FLAG for NKIR Protein PCR was carried out under the following reaction conditions.
Template: pGEMTE-NK1
Primers: NKflag

```
Primers:
NKflag (5'-GCGAATTCCACCATGGACTACAAAGACGATGACGACAAG
TTGCCATCTTTAGTTCCCTGTGTT-3'/SEQ ID NO: 28)<=>NKr1
(5'-CGTGTCGACTCACTAGCAGAGAACCTCCTCACAGTC-3'/
SEQ ID NO: 29)
```

Reaction Conditions:
94° C. for 2 minutes; and
25 cycles of 94° C. for 20 seconds, 60° C. for 30 seconds, and 68° C. for 2 minutes.

PCR was carried out using KOD plus (TOYOBO; buffer, dNTPs, and MgSO₄ were attached thereto). After purification with MicroSpin S-300 HR column (Amersham Biosciences), the PCR product was digested with EcoRI and SalI and subjected to agarose gel electrophoresis. A band of about 1.3 kb was excised from the gel. After purification with a MicroSpin S-300 HR column, the fragment was inserted between EcoRI and SalI sites of pCOS2 to yield pCOS2-NK-FLAG.

(3) Construction of NKIR Fusion Protein and Rabbit Polyclonal NKIR Antibody

*E. coli* BL21(DE3) was transformed with the expression plasmid pET32a-NK-sol for thioredoxin fusion protein. The *E. coli* was cultured overnight in LB medium containing 50 μg/ml ampicillin, and the suspension was diluted to the final concentration of 1% with LB medium containing 50 μg/ml ampicillin for large scale culture. Cells were cultured until the absorbance at 600 nm reached 0.4. Then, IPTG was added at the final concentration of 1 mM to induce the expression of the protein. After 4.5 hours of culture, bacterial cells were precipitated and collected by centrifugation. The cells were suspended in PBS. The bacterial cells were sonicated in a sonicator, and then centrifuged. The resulting supernatant was discarded, and the precipitated fraction was collected. The cells were lysed with phosphate buffer (PBS) containing 7 M urea, and the lysate was filtered with a 0.45-μm filter. The NKIR fusion protein was isolated from the filtrate using His-Trap kit (Amersham Biosciences). The eluate was dialyzed against 50 mM Tris (pH8.3), and thus a sample of solubilized fusion protein was obtained. SDS-PAGE, followed by Coomassie staining, confirmed that the fusion protein obtained had the expected molecular weight.

Figure 2:
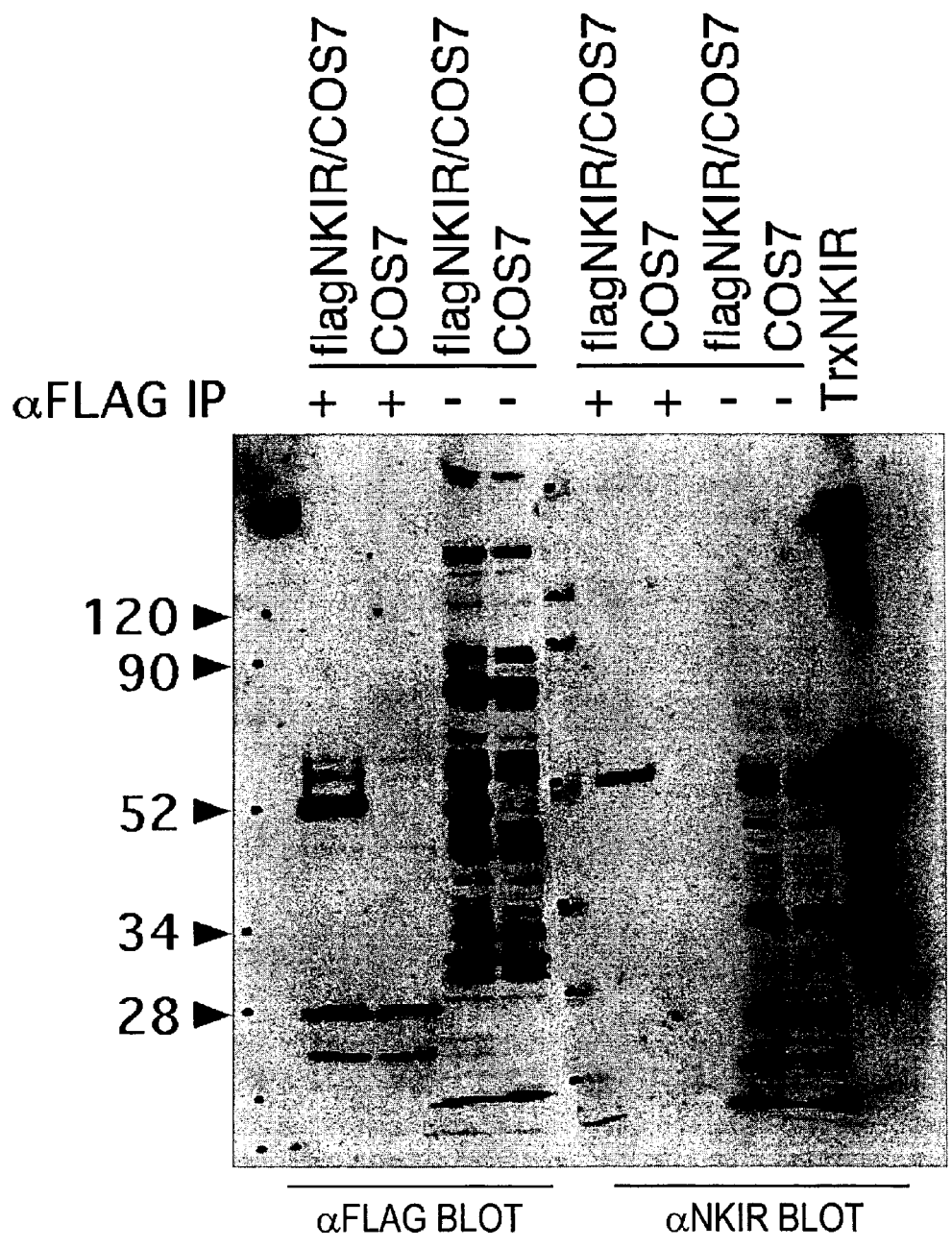
FIG. 2 is a photograph showing the detection of NKIR protein using an anti-NKIR polyclonal antibody.

Rabbits were immunized using the NKIR fusion protein as an immunogen to prepare polyclonal antibodies. The antigen protein solution was adjusted to 0.2 mg/0.5 ml, and 0.5 ml of Freund's complete adjuvant (Becton Dickinson) was added thereto. 1 ml of the mixture was inoculated subcutaneously (day 1, 4, and 11). On day 19, 26, and 33, 0.05 mg of the antigen protein was intravenously injected. After blood sampling, increase in antibody titers was confirmed. Then, the blood was collected and the antiserum was loaded onto protein A affinity column to purify the antibody protein. Western blotting as described below was used to confirm that the obtained polyclonal antibody binds to NKIR expressed transiently in the animal cell COS-7.

pCOS2-NK-FLAG was introduced into COS-7 cells using FuGENE6 (Roche Diagnostics) according to the manufacturer's instructions. After two days of culture, a lysis solution (10% glycerol, 50 mM Tris (pH7.6), 150 mM NaCl, 5 mM NP-40, and protease inhibitors (complete)) was added to the cells. Then, the resulting suspension was centrifuged to obtain a supernatant comprising soluble membrane protein components. Anti-FLAG M2 antibody resins were added to the soluble fraction to immunoprecipitate FLAG-NKIR. The obtained sample was fractionated by SDS-PAGE, and then transferred onto a PVDF membrane. Detection was carried out using anti-NKIR polyclonal antibody. As the primary antibody, the rabbit-derived polyclonal antibody (4.1 mg/ml IgG) was diluted 1000 times. As the secondary antibody, HRP-conjugated anti-rabbit IgG antibody (Amersham Biosciences) was diluted 3000 times. The ECL Western Blotting Detection System (Amersham Biosciences) was used in the detection. In a control experiment, the presence of FLAG-NKIR protein was confirmed using 1000-times diluted anti-FLAG M2 antibody (Sigma) and 3000-times diluted HRP-conjugated anti-mouse IgG antibody (Amersham Biosciences) as the secondary antibody (FIG. 2).

Example 3

Tissue Expression Analysis and Expression Analysis of NK Cell Lines

Tissue expression profiles were analyzed by PCR using the commercially available cDNA panel (Multiple Tissue cDNA (MTC) panel; Clontech Laboratories, Inc.) as a template.

PCR was carried out under the following reaction conditions.

Template: MTC panel I, II, Human Immune System and Human Blood Fraction (Clontech Laboratories, Inc.)

```
Primers:
NKIR07 (5'-AGGTCAGAGTGCAGGCTCCTGTATC-3'/
SEQ ID NO: 30)<=>NKIR08 (5'-TAGAACTGTCCTTTCTC-
CCCAC
GGT-3'/SEQ ID NO: 31)
```

Reaction Conditions:
94° C. for 30 seconds; and
35 cycles of 94° C. for 30 seconds and 65° C. for 2 minutes.

PCR was carried out using TaKaRa Ex Taq (buffer and dNTP mixture were provided). The reaction volume was 50 µl. 5 µl of the reaction solution was electrophoresed in a 1% agarose gel. A 0.6 kb band was observed. G3PDH primers attached to the MTC panel were used in a control reaction.

Figure 3:
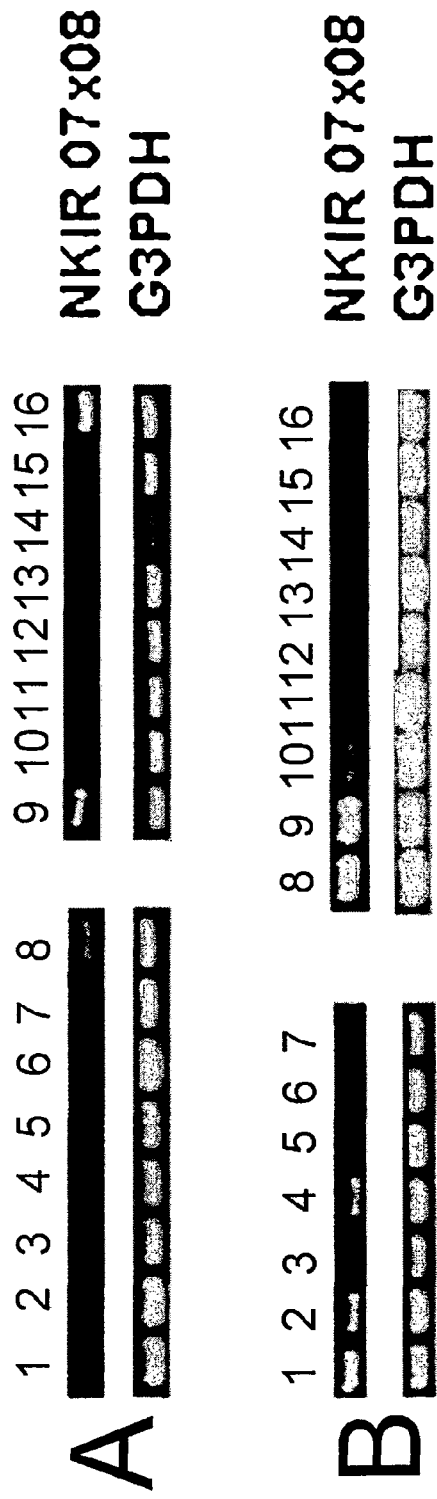
FIG. 3 is a photograph showing an RT-PCR analysis result for tissue expression.

The result showed that the gene was specifically expressed in the immune system such as in the spleen and leukocytes (FIG. 3). When the number of subjects in the analysis was increased using subsets of "Blood Fraction" and "Immune System" of the above-described MTC panel, the gene was found to be specifically expressed in monocytes and in resting CD8+ for the "Blood Fraction" and in lymph nodes in addition to spleen and leukocytes for the "Immune System" (FIG. 3).

Western blotting analysis was carried out using a cell lysate prepared from NK-92 cell line, an established natural killer (NK) cell line, purchased from ATCC (catalog No: CRL-2407).

NK-92 cell line was cultured in NK-92 passaging medium (α-MEM medium (Invitrogen) comprising 12.5% fetal calf serum (Invitrogen), 12.5% horse serum (Invitrogen), 2 mM glutamine (Invitrogen), 0.1 mg/l penicillin (Invitrogen), 0.1 mg/l streptomycin (Invitrogen), 1 mM sodium pyruvate (Invitrogen), 100 µM 2-mercptoethanol (Invitrogen), 2 mM folic acid (SIGMA-ALDRICH), and 20 mM myo-inositol (SIGMA-ALDRICH)) in the presence of 10 ng/ml interleukin-2 (SIGMA-ALDRICH). The resulting $1 \times 10^7$ cells were suspended in 500 µl of NP40 lysis buffer (1% NP40/150 mM NaCl/50 mM Tris-HCl (pH8.0)), and allowed to stand on ice for 30 minutes. The suspension was then fractionated through micro centrifugation at 15,000 rpm to obtain a supernatant. The supernatant was used as a cell lysate in Western blotting analysis.

The protein concentration in the cell lysate was determined by using the Dc Protein Assay Kit (BIO-RAD Laboratories) and, as a control, bovine serum albumin (Fraction V) from PIERCE.

PAG-Mini (gel with a gradient of 4% to 20%; Daiichi Pure Chemicals Co. Ltd.) and 10 µg or 20 µg of lysate of NK-92 cell line were used in SDS-PAGE for the Western blotting analysis. The same immunogen as that used to immunize rabbits in the polyclonal antibody preparation was diluted 200 times with NP40 lysis buffer, and then 1 µul of the resulting sample was simultaneously used as a positive control. The electrophoresis was carried out at 20 mA. After electrophoresis, the proteins were transferred onto PVDF membrane (Hybond-P, Amersham Biosciences) from the gel using SEMI-DRY TRANSFER CELL (BIO-RAD Laboratories) under the condition of 20 volts for 45 minutes. Western blotting was carried out using ECL plus Western Blotting Detection System (Amersham Biosciences) according to the method described in the manual. However, ECL-Advance blocking agent (Amersham Biosciences) was used as a blocking reagent at the concentration of 2%. 1,000-time diluted polyclonal antibody (4.1 mg/ml IgG) derived from rabbit described above was used as the primary antibody, while 3,000-time diluted anti-rabbit IgG derived from donkey (horseradish peroxide linked whole antibody; Amersham Biosciences) was used as the secondary antibody. It was confirmed that there are molecular species that cross-reacted with the anti-NKIR polyclonal antibody.

Figure 4:
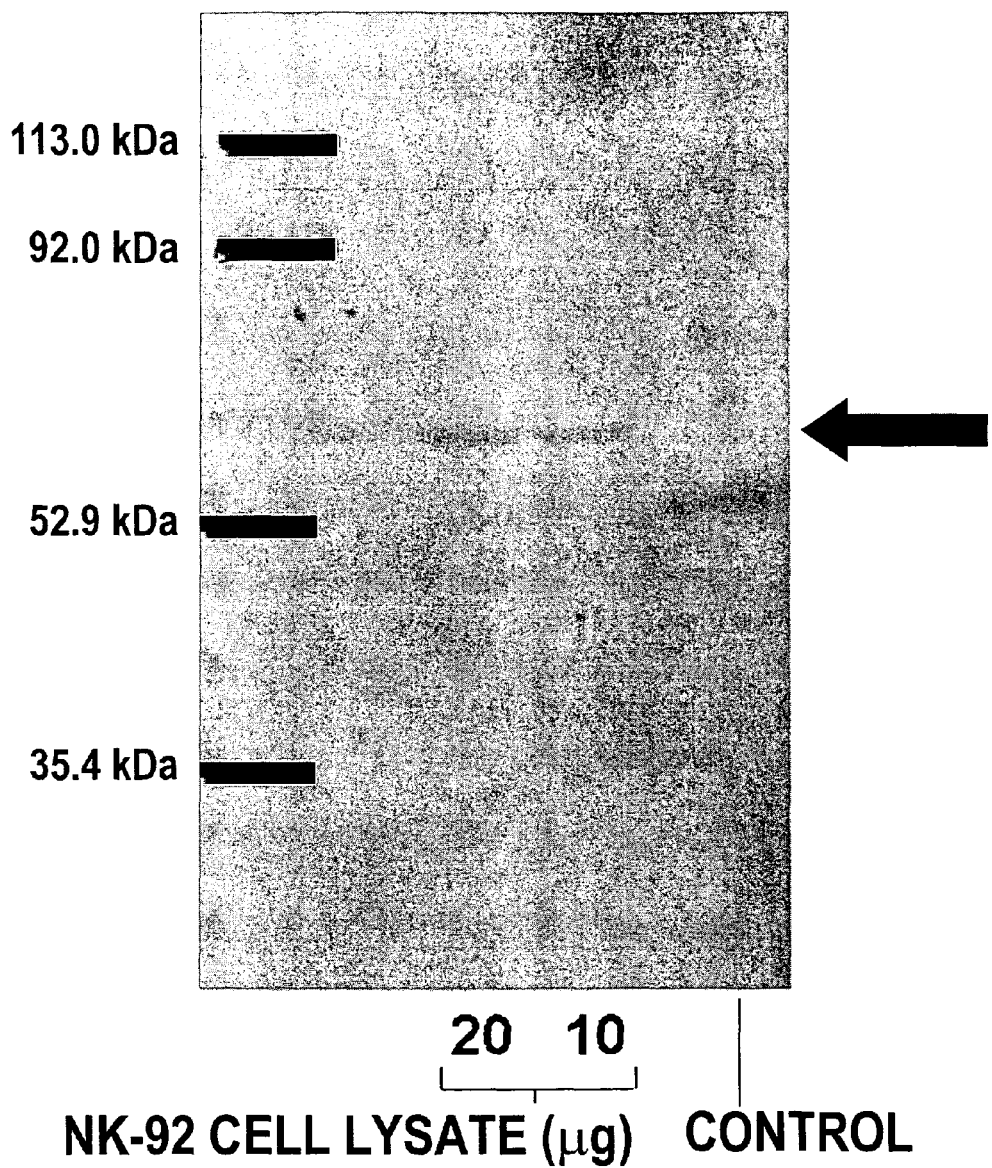
FIG. 4 is a photograph showing the detection of natural NKIR protein expressed in NK-92 cell line using an anti-NKIR polyclonal antibody.

The result showed that NK-92 cell line expresses an about 60-kDa protein cross-reactive to the polyclonal antibody obtained from the rabbit immunized with NKIR protein expressed in E. coli (FIG. 4).

Furthermore, to confirm that the NKIR molecule is expressed on the surface of NK cells, flow cytometric analysis of NK-92 cell line was carried out using the anti-NKIR polyclonal antibody.

Figure 5:
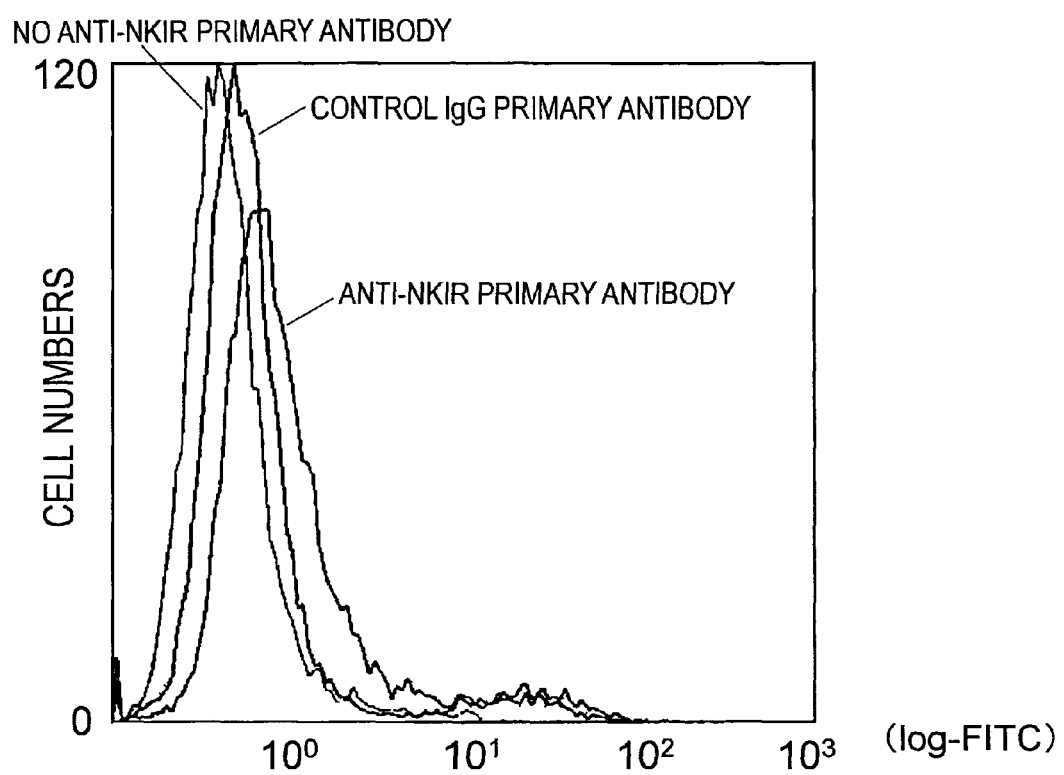
FIG. 5 is a graph showing flow cytometric analysis of NK-92 cell line using an anti-NKIR polyclonal antibody.

After $5 \times 10^5$ cells were suspended in 100 µl of FACS buffer (phosphate buffered saline comprising 2.5% fetal calf serum and 0.02% $NaN_3$), the anti-NKIR polyclonal antibody was added thereto at the final concentration of 82 µg/ml. As a negative control, cells to which a purified rabbit IgG had been added at the same concentration were prepared. The cell samples were allowed to stand on ice for one hour, and then subjected to centrifugation at a low speed (at 300×g for 5 minutes) to collect cells. The cells were washed with FACS buffer, and centrifuged again at low speed to collect the cells. Then, the collected cells were suspended in FACS buffer comprising an FITC-conjugated goat anti-rabbit IgG antibody (Beckman Coulter) at the final concentration of 14 µg/ml, and allowed to stand on ice for 30 minutes. The cells were collected by centrifugation at low speed, and washed with FACS buffer. The cells were suspended in 500 µl of FACS buffer, and analyzed by flow cytometry (Beckman Coulter; EPICS). The result showed that the NKIR molecule was expressed on the surface of the cells (FIG. 5).

Example 4

Cloning of the Full-Length NKIR Gene by RACE Using NK-92 Cell Line-Derived cDNA The full-length NKIR gene was cloned again by 5'- and 3'-RACE using total RNAs prepared from NK-92 cell line.

Using RNeasy (QIAGEN) kit, 377.7 µg of total RNAs was prepared from $5.4 \times 10^7$ cells of NK-92 cell line cultured by the method in Example 3. 5'- and 3'-RACE were carried out using SMART RACE cDNA Amplification Kit (Clontech) and as a template 1 µg of RNA prepared as described above. Gene-specific primers used in 5'- and 3'-RACE were NKIR08 and NKIR07, respectively. In each reaction, a major amplification product of about 1.3 kb was obtained in the 1st round PCR. The amplified fragment was excised from the agarose gel, purified with QIAquick (QIAGEN) kit, and then cloned into pCR2.1-TOPO (Invitrogen). The yielded eight transformants derived from TOP10F' were cultured in 2 ml of LB medium comprising 0.1 mg/ml ampicillin. Plasmids were prepared using QIAprep kit (QIAGEN) from the cultured *E. coli*, and then sequenced. As a result, 5'-RACE yielded a cDNA sequence comprising an insert that is 36 nucleotides longer than the previously identified sequence at the 5' end. The cDNA was used as pTOPONKIR626 in subsequent analyses. 3'-RACE yielded the cDNA clone pTOPONKIR620 comprising a downstream extension of about 500 nucleotides. The nucleotide sequence is shown in SEQ ID NO: 3 and the amino acid sequence of the protein encoded by the nucleotide sequence is shown in SEQ ID NO: 4 in the Sequence Listing. This sequence was confirmed to be located in the NKIR region of chromosome 1 in the human genome.

Then, focusing on the insertion sequence of 36 nucleotides at the 5' end, expression vectors respectively comprising the sequence identified in Example 1 and newly isolated sequence were constructed using pCOS1 as the vector backbone to use in the transient expression in COS-7 cells.

PCR was carried out using pGEM-TE NK1 as a template and the following primers (0.2 µM each): NKIR09 (5'-GAAT-TCACACACCCACAGGACCTGCA-3'/SEQ ID NO: 32) and NKIR10 (5'-GGATCCACTGAAGGACCCACA-GAAAG-3'/SEQ ID NO: 33). The HF Polymerase kit (Clontech) was used as PCR kit. The reaction conditions were: denaturation at 94° C. for 30 seconds; 25 cycles of 94° C. for 15 seconds, 55° C. for 30 seconds, and 72° C. for 1 minute; followed by extension at 72° C. for 5 minutes. The reaction solution was subjected to agarose gel electrophoresis, and the yielded 1.5 kb fragment was purified using QIAquick Gel Extraction kit (QIAGEN). The fragment was then cloned into pCR2.1-TOPO (Invitrogen) and introduced into *E. coli* strain TOP10F'. Plasmid was prepared from the resulting ampicillin-resistant strain using QIAprep Miniprep kit (QIAGEN), and then sequenced. The PCR error-free clone pTO-PONKIR219 was selected for subsequent analyses.

Then, 5 µg of pTOPONKIR219 and 1.15 µg of pBluescript II SK+ (Stratagene) were digested with 20 units each of EcoRI and BamHI at 37° C. for one hour. After agarose gel electrophoresis, the resulting 1.5 kb and 3.0 kb fragments were purified using QIAquick Gel Extraction kit (QIAGEN). Then, ligation was carried out using a 1 µl aliquot of each eluate (40 µl) and LigaFAST Ligation kit (Promega), and introduced into the *E. coli* TOP10F' strain. Plasmids were prepared from the resulting ampicillin-resistant strains using QIAprep Miniprep kit (QIAGEN). The clones were tested by digestion with the restriction enzyme PstI. The clone pBSNKIR224 gave a 1.3 kb fragment by the digestion, and therefore used in the subsequent analyses. The 4 kb and 0.4 kb fragments obtained respectively from pBSNKIR224 and pTOPONKIR626 by double digestion with BstP1 and BglII were then isolated by agarose gel electrophoresis and purified with QIAquick Gel Extraction kit (QIAGEN). The fragments were ligated using LigaFAST Ligation kit (Promega), and introduced into *E. coli* DH5α. Plasmids were prepared from the resulting ampicillin-resistant strains using QIAprep Miniprep kit (QIAGEN), and then sequenced. The clone pBSNKIRfull605 comprising a 36-bp insert at the 5' end was used in the subsequent analyses.

Finally, 1.4-kb EcoRI-NotI fragments derived from pBSNKIR224 and pBSNKIRfull605 were inserted between EcoRI and NotI sites of pCOS1 to construct the expression vectors pCOSNKIR610 and pCOSNKIRfull610, respectively. The two plasmids were transfected into COS-7 cells as donor DNAs by lipofection method using MIRUS TransIT-LT1 (PanVera) according to the manufacturer's instructions, and the cells were cultured for 2 days. Then, the cells were trypsinized using a trypsin/EDTA solution (Invitrogen), and washed twice with DMEM (Invitrogen) comprising 10% fetal calf serum (Invitrogen). Flow cytometric analyses were then carried out by the same method as described in Example 3.

Figure 6:
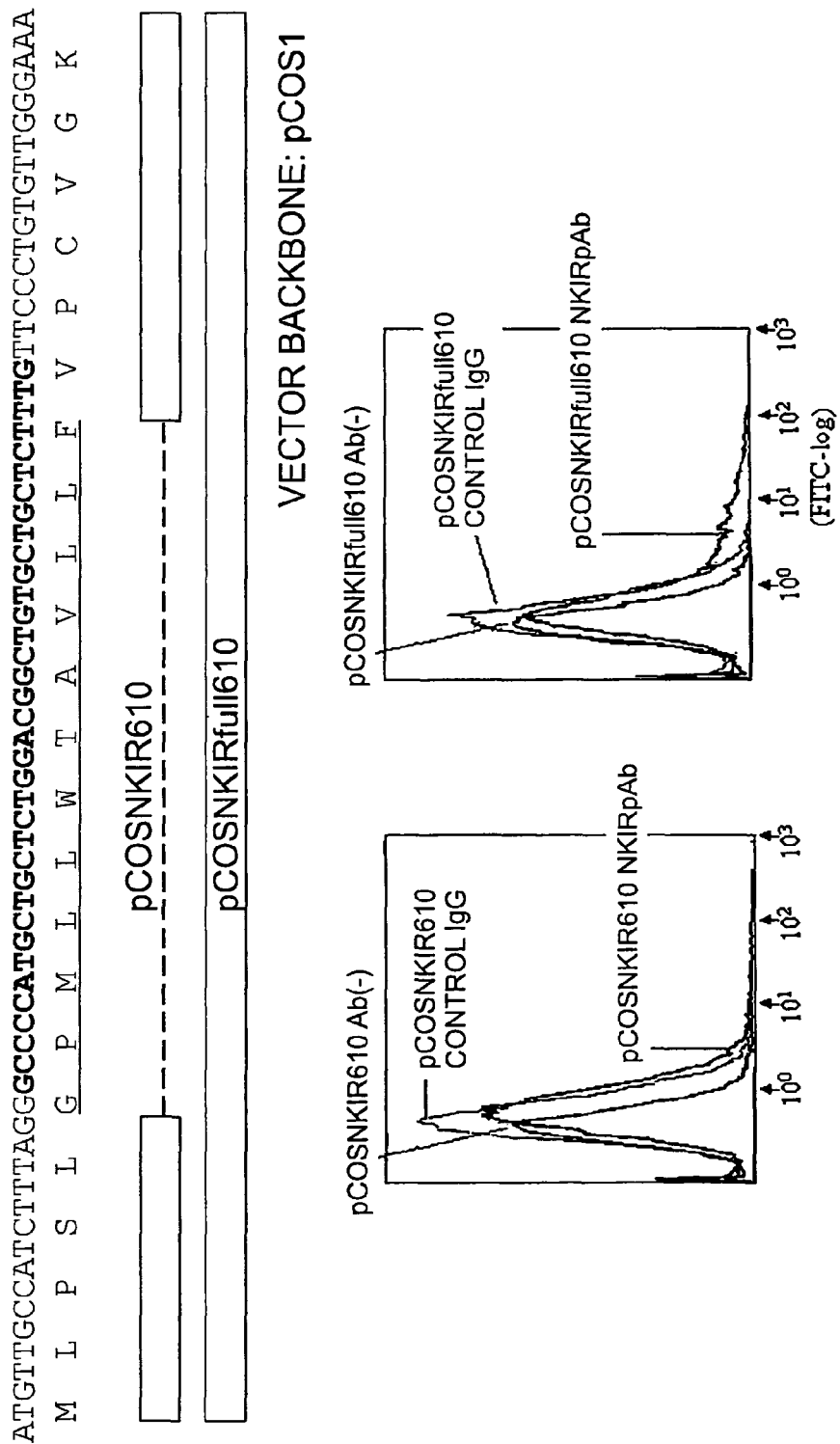
FIG. 6 shows a flow cytometric analysis for the transient expression of the NKIR gene in the COS-7 cell line.

A cell fraction was found to be shifted in the FITC detection only when COS-7 cells were transfected with the expression plasmid for NKIR isolated from NK-92, which comprises the insertion sequence of 36 nucleotides at the 5' end. Accordingly, the result showed that the clone comprising the 36-nucleotide insertion functions as a secretory form (FIG. 6).

Example 5

Cloning of Mouse NKIR Sequence

The mouse genomic sequence was searched by BLAST (tblastn) using the amino acid sequence of human NKIR as a query. A region on chromosome 1 that gave a hit over the entire sequence was identified (FIG. 7). With respective to the chromosomal structure, this mouse chromosomal region matches the human chromosomal region on which human NKIR has been mapped.

Primers (mNKIRf1 (5'-CTCAGTAAAGGCAGAGTG-GAGTACC-3'/SEQ ID NO: 34)<=>mNKIRr1 (5'-ATA-CATTAGAACCACAGCCGCAATG-3'/SEQ ID NO: 35)) were designed based on the putative translated region. The gene was cloned from a mouse spleen cDNA library by PCR amplification and sequenced. The presence of spliced transcripts was verified.

5'- and 3'-RACE PCR were carried out using mouse spleen Marathon-Ready cDNA (Clontech) as a template under the following reaction conditions:

1st Round PCR:
Template: 2.5 µl of Marathon Ready cDNA

```
Primers:
AP1 (5'-CCATCCTAATACGACTCACTATAGGGC-3'/
SEQ ID NO: 36)<=>mNKIRf1 for 3' RACE AP1<=>mNKIRr1
for 5' RACE
```

2nd Round PCR:
Template: 2.5 µl of 30-time diluted 1st round PCR product

```
Primers:
AP2 (5'-ACTCACTATAGGGCTCGAGCGGC-3'/
SEQ ID NO: 37)<=>mNKIRf3 (5'-CTCAAGAAGTTCCCCTTGGTT
GTCTC-3'/SEQ ID NO: 38) for 3' RACE AP2<=>mNKIRr3
(5'-GCCAGATAGTTAGCATGTTGCTCTTG-3'/SEQ ID NO: 39)
for 5' RACE
```

1st Round PCR:
Reaction Conditions:
94° C. for 1 minute; and
35 cycles of 94° C. for 10 seconds and 68° C. for 3 minutes.
2nd Round PCR:
Reaction Conditions:
94° C. for 1 minute; and
20 cycles of 94° C. for 10 seconds and 68° C. for 3 minutes.

A reaction solution was prepared and PCR was carried out using TaKaRa LA Taq (TAKARA; buffer, dNTPs, and MgCl$_2$ were attached thereto) according to the manufacturer's instructions. The products of 2nd round PCR were electrophoresed in an agarose gel, and the band resulting from the PCR amplification was excised. After purification with QIAquick Gel Extraction Kit, the product was inserted into pGEM T-Easy Vector. DH5α was transformed, and plasmids were prepared from the resulting clones and sequenced.

As a result, the clone was deduced to be a membrane protein comprising 268 amino acids. The nucleotide sequence of the obtained clone is shown in SEQ ID NO: 5 and the amino acid sequence of the protein encoded by the nucleotide sequence is shown in SEQ ID NO: 6 in the Sequence Listing. When the human and mouse sequences are compared (FIG. 8), the mouse sequence has a structure that is shorter than that of the human sequence at both N and C termini. The mouse sequence comprises a single N-glycosylation site, a single ITIM motif, a single transmembrane domain, and two Ig-like domains in the equivalent region.

Motif searches by Prosite, Pfam, Psort, and the like revealed the following sequence features:
N-glycosylation sites: (N[^P][ST][^P]) 180, NYSC; 188, NISR
ITIM motif: (Yxx[VL]) 259, YANV
Ig-like domains: 33-89 and 128-185
Transmembrane domain: 221-237

Example 6

Cloning of 2KIR3DL

An assay system used for detecting ITIM activity comprises a modified method using T cells as recipient cells which comprises the step of determining luciferase activity under the control of the NFAT cascade (Fry A M, Lanier L L, Weiss A., J Exp Med. (1996), 184, 295-300).

2KIR3DL, a known KIR gene, was cloned using a human spleen cDNA library.
PCR was Carried out Under the Following Reaction Conditions:
Template: Human Spleen Marathon-Ready cDNA (Clontech)

```
Primers:
p58KIR01 (5'-GAATTCATGTCGCTCATGGTCGTCAG-3'/
SEQ ID NO: 40)<=>p58KIR02 (5'-GGATCCTCAGGGCTCAGCAT
TTGGAA-3'/SEQ ID NO: 41)
```

Reaction Conditions:
94° C. for 30 seconds;
30 cycles of 94° C. for 15 seconds, 52° C. for 30 seconds, and 72° C. for 1 minute; and
72° C. for 5 minutes.

PCR was carried out using HF polymerase (Clontech). A 1-kb fragment was separated by agarose gel electrophoresis, and then purified with QIAquick (QIAGEN). The purified product was cloned into pCR2.1-TOPO, and introduced into E. coli TOP10F'. The plasmid was prepared from the transformant using QIAprep (QIAGEN) kit, and a clone comprising a PCR error-free sequence (pTOPO58KIR303) was selected to use in the subsequent analyses.

Example 7

Construction of an In-Frame Fusion

An in-frame fusion between the cytoplasmic ITIM motif of NKIR and the extracellular domain of 2KIRDL3 obtained in Example 6 was constructed by the following procedure.

First, fusion PCR was carried out under the following reaction conditions.
1st Round PCR A
Template: pTOPO58KIR303

```
Primers:
p58KIR01<=>p58NKIR04 (5'-AGGGGCCCAGCTTTTCTCCAGCGAT
GAAGGAGAAAGAAGA-3'/SEQ ID NO: 42)
```

1st Round PCR B
Template: pBSNKIR224

```
Primers:
p58KIR03 (5'-TCTTCTTTCTCCTTCATCGCTGGAGAAAAGCTGGGCC
CCT-3'/SEQ ID NO: 43)<=>T3+ (5'-GCAATTAACCCTCACTAA
AGGGAAC-3'/SEQ ID NO: 44)
```

The condition used for both reactions is as follows:
94° C. for 30 seconds,
30 cycles of 94° C. for 15 seconds, 55° C. for 30 seconds, and 72° C. for 45 seconds; and
72° C. for 2 minutes.

PCR was carried out using HF polymerase (Clontech). 0.8- and 0.4-kb fragments derived from PCR A and B, respectively, were separated by agarose gel electrophoresis, and then purified using QIAquick (QIAGEN). A 10-μl aliquot of each purified product (50 μl) was used as a primer in the second round of PCR described below.
Template: 10 μl of each reaction product described above
The reaction conditions were as follows:
94° C. for 30 seconds; and
15 cycles of 94° C. for 15 seconds, 55° C. for 30 seconds, and 72° C. for 90 seconds.

After the reaction, the template described below was added to 50 μl of the reaction mixture at the final concentration of 1 μM.
Primers: p58KIR01<=>T3+
Reaction Conditions:
94° C. for 30 seconds;
35 cycles of 94° C. for 15 seconds, 55° C. for 30 seconds, and 72° C. for 2 minutes; and
72° C. for 4 minutes.

A 1.2-kb fragment was separated by agarose gel electrophoresis, and then purified using QIAquick (QIAGEN). The fragment was cloned into pCR2.1-TOPO, and introduced into E. coli TOP10F'. Plasmid was prepared from the transformant using QIAprep (QIAGEN) kit, and a clone comprising a PCR error-free sequence (pBSKIR58NKIR314) was selected and used in the subsequent analyses.

Next, 1 μg each of pCXND3 and pBSKIR58NKIR314 were digested with 20 units of EcoRI and NotI at 37° C. for one hour, and then electrophoresed in an agarose gel. The resulting 7.8- and 1.2-kb fragments were purified using QIAquick Gel Extraction kit (QIAGEN). Then, ligation was carried out using a 1-μl aliquot of each eluate (40 μl) and LigaFAST Ligation kit (Promega), and the resulting plasmid was introduced into *E. coli* strain DH5α. Ampicillin-resistant strains were saved and colony PCR was carried out using p58KIR01 and p58NKIR10 primers (0.5 μM each). This treatment was carried out using Premix ExTaq (TaKaRa) as PCR polymerase, under conditions of: denaturation at 94° C. for 5 minutes; followed by 35 cycles of 94° C. for 30 seconds, 55° C. for 30 seconds, and 72° C. for 90 seconds. One fifth of the resulting reaction product was subjected to agarose gel electrophoresis, and the clone pCXND3KIR58NKIR313 that gave a 1.3-kb PCR fragment was used in the subsequent analyses.

Example 8

Preparation of Stable Transformants

ChimeraA10, a candidate strain for a stable transformant, was prepared from a T cell line Jurkat using as a donor DNA pCXND3KIR58NKIR313 obtained in Example 7 described above. The procedure used to obtain the strain is described below.

Transduction was achieved by electroporation using pCXND3KIR58NKIR313 as donor DNA and Jurkat strain as recipient cell. 20 μg of the donor DNA was pre-digested with 20 units of PvuII (TaKaRa) at 37° C. for one hour. After chloroform/phenol treatment followed by ethanol precipitation, the DNA was dissolved in 20 μl of sterilized water. As recipient cells, Jurkat cells were passaged in RPMI1640 medium comprising 10% FBS, washed with potassium-based phosphate buffered saline (K-PBS), and then suspended in K-PBS at the cell density of $10^7$ cells/ml to prepare 0.8 ml of a cell suspension. Electroporation was carried out using Gene Pulsar II (Bio-Rad) under the pulse condition of 0.3 kV and 950 μFD. After pulse application, the cells were suspended in 48 ml of passaging medium and cultured overnight under a condition without selective pressure. Then, the candidate ChimeraA10 cell line for the stable transformant was obtained under a selective pressure using geneticin (Invitrogen) at the final concentration of 400 μg/ml. Flow cytometric analysis was carried out by the same procedure as described in Example 3 except for using GL183 monoclonal antibody (Beckman Coulter) as the primary antibody and FITC-conjugated anti-rabbit IgG antibody (Beckman Coulter) as the secondary antibody.

Figure 9:
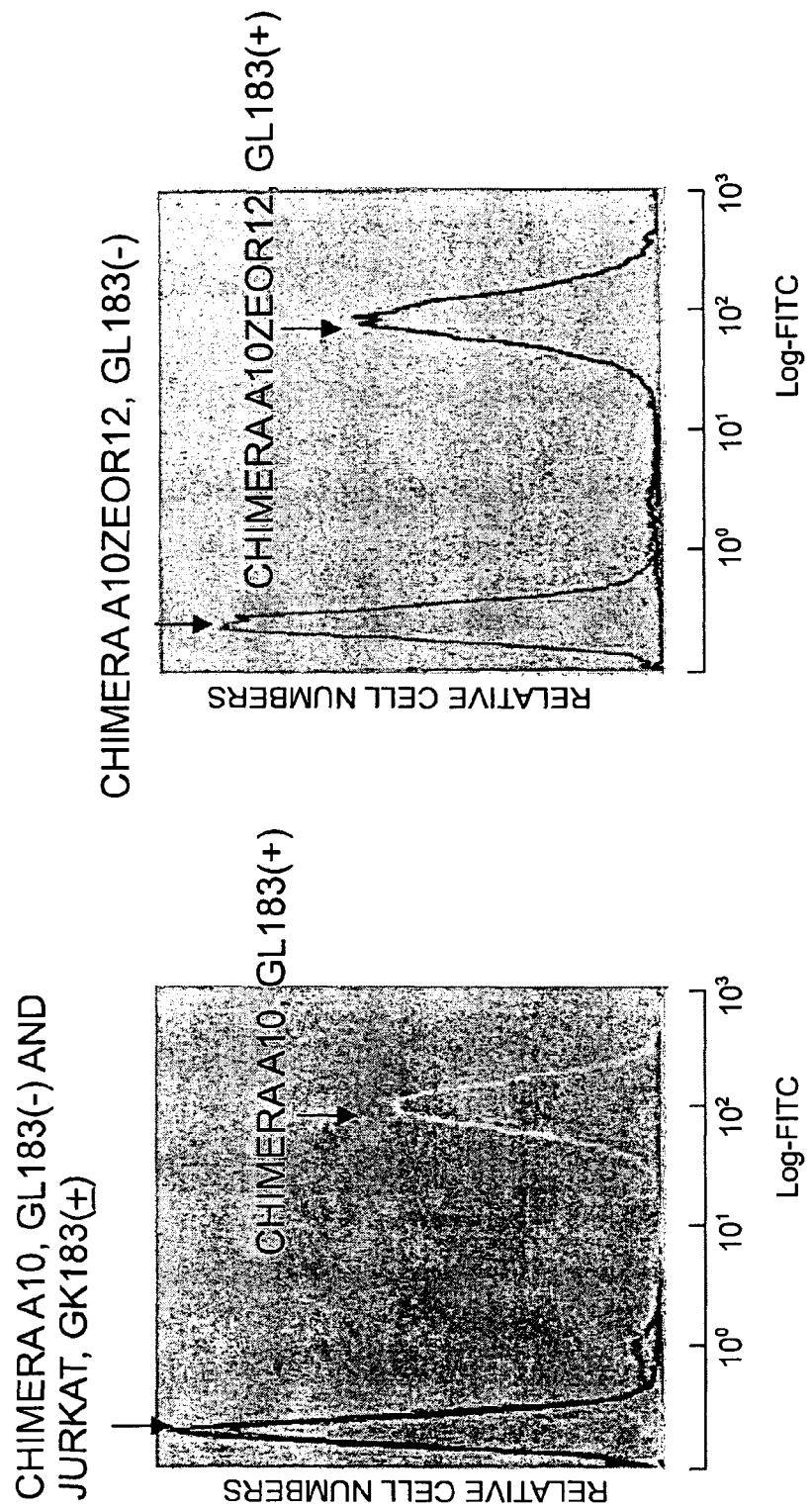
FIG. 9 is a graph showing a flow cytometric analysis of each transformant cell line.

As a result, an FITC-stained cell fraction was detected, indicating that the above-described fusion protein was expressed in ChimeraA10 cell line (FIG. 9).

Example 9

Preparation of Dual Transformant

The luciferase reporter plasmid pNFATlucZEOR324 was transformed into ChimeraA10 strain obtained in Example 8 as recipient cell to obtain a dual transformant. pNFATluc-ZEOR324 was constructed by the procedure as described below.

2.5 μg of the luciferase reporter gene pNFAT-TA-Luc (included in Mercury Pathway Profiling Luciferase system 2 (Clontech)) and 5 μg of pCOSIIZEO (prepared from SCS-110 strain (Stratagene), a dam-strain) were digested with 20 units each of AccI (TaKaRa) and ClaI (TaKaRa), respectively, at 37° C. for one hour, and then subjected to agarose gel electrophoresis. 5- and 2.2-kb fragments obtained respectively by the digestion were purified using Gel Extraction Kit (QIAGEN). The fragment derived from pNFAT-TA-Luc was treated with calf intestine alkaline phosphatase at 37° C. for 30 minutes, and then purified using QIAquick Nucleotide Removal kit (QIAGEN). The two fragments were ligated using LigaFAST Ligation kit (Promega), and introduced into *E. coli* strain DH5α. Plasmid was prepared from the resulting ampicillin-resistant strain using QIAprep Miniprep kit (QIAGEN). The plasmid was tested by double-digestion with the restriction enzymes EcoRI and SalI. A clone that gave 4.15- and 3.15-kb fragments by the digestion was named the pNFATlucZEOF324 clone comprising the insert in a forward-orientation; and a clone that gave 5.15- and 2.15-kb fragments by the digestion was pNFATlucZEOR324 clone comprising the insert in an reverse orientation. Both plasmids were used in the subsequent analyses.

Transduction was conducted by electroporation using pNFATlucZEOR324 as donor DNA and chimeraA10 cell line as recipient cell. 20 μg of the donor DNA was pre-digested with 20 units of PvuII (TaKaRa) at 37° C. for 1 hour. After chloroform/phenol treatment followed by ethanol precipitation, the DNA was dissolved in 20 μl of sterilized water. ChimeraA10 cells (recipient cells) were passaged in RPMI1640 medium comprising 10% FBS and 400 μg/ml geneticin, washed with potassium-based phosphate buffered saline (K-PBS), and suspended in K-PBS at the cell density of $10^7$ cells/ml to prepare 0.8 ml of a cell suspension. Electroporation was carried out using Gene Pulsar II (Bio-Rad) under the pulse condition of 0.3 kV and 950 μFD. After pulse application, the cells were suspended in 48 ml of passaging medium comprising 400 μg/ml geneticin and cultured overnight under a condition without selective pressure. Then, the candidate cell line for the stable transformant was obtained under a selective pressure using zeocin (Invitrogen) at the final concentration of 100 μg/ml. Genomic DNA was prepared from the resulting zeocin-resistant cell line using DNeasy Tissue Kit (QIAGEN). PCR was carried out using a 5-μl aliquot of the final eluate (0.4 ml). Premix ExTaq was used as the PCR polymerase. Luc01 (5'-TTCATACAGAAG-GCGTGGAG-3'/SEQ ID NO: 45) and Luc02 (5'-CGT-TCGCGGGCGCAACTGCA-3'/SEQ ID NO: 46) were used as primers. The reaction was carried out under conditions of: denaturation at 94° C. for 5 minutes; and 25 cycles of 94° C. for 15 seconds, 55° C. for 30 seconds, and 72° C. for 45 seconds; followed by extension at 72° C. for 5 minutes. Clones which gave a 0.5-kb PCR fragment in agarose gel electrophoresis were selected, and then the final screening was carried out by detecting luciferase activity.

The candidate cell line for the stable transformant with pNFATlucZEOR324, which was obtained from chimeraA10 cell line, was suspended at the concentration of $6.7 \times 10^4$ cells/ml in a passaging medium containing 400 μg/ml geneticin and 100 μg/ml zeocin. A 75-μl aliquot of the cell suspension was plated into each well of anti-human CD3-coated microtiter plates (Beckton Dickinson) and non-coated immunomicroplates to carry out luciferase assay. After 20 hours of cultivation at 37° C., an equal volume (75 μl) of Dual-Glo Luciferase Buffer (Promega) was added to each well. The samples were allowed to stand for 10 minutes, and then the chemiluminescence was measured using the luminometer MicroLumat LB96P (EG&G Berthold) for 5 seconds for each well.

The chimeraA10ZEOR12 cell line that exhibited intense chemiluminescence only when cultured in anti-human CD3-coated microtiterplates was selected as a stable transformant. The cell line was analyzed by flow cytometry by the same procedure as described above.

The result showed that the cell line also expresses the fusion protein that is expressed in ChimeraA10 cell line (FIG. 9).

Example 11

Assay for the Activity of ITIM Derived from NKIR

A functional evaluation of the NKIR-derived ITIM motif was done using chimeraA10ZEOR12 cell line. The method used is described below.

The chimeraA10ZEOR12 cell line was suspended at a concentration of $5 \times 10^5$ cells/ml in a passaging medium containing 400 µg/ml geneticin and 100 µg/ml zeocin. A 100-µl aliquot of the suspension was added to each well of anti-human CD3-coated microtiterplates (Beckton Dickinson). After the cells were cultured at 37° C. for 6 hours, GL183 antibody (Beckman Coulter) was added thereto at the final concentration of 1 µg/ml. The cells were cultured at 37° C. overnight. Then, the cells were washed twice with passaging medium containing 400 µg/ml geneticin and 100 µg/ml zeocin. After the washed cells were suspended in 100 µl of the medium containing rat anti-mouse IgG antibody at the concentration of 0, 2, or 10 µg/ml, luciferase activity was assayed according to the same procedure as described in Example 9.

Figure 10:
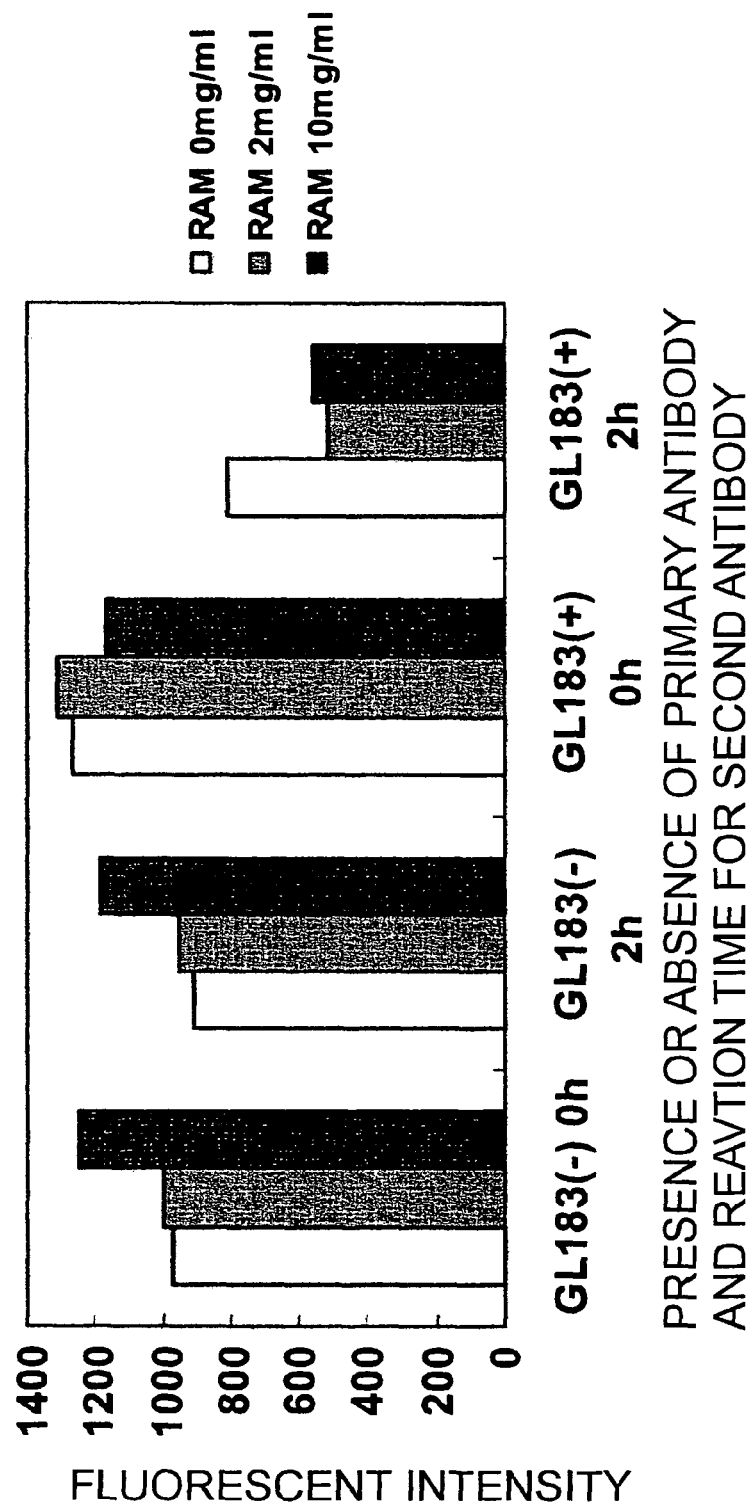
FIG. 10 is a histogram showing an assay result for ITIM activity determined using luciferase activity as an indicator.

The result showed that crosslinking with the rat anti-mouse IgG antibody inhibited the luciferase activity by 33.3% in average for three cases (FIG. 10), indicating that the ITIM motif within the cytoplasmic domain of NKIR molecule had ITIM activity.

Example 12

Cloning of CD8α Chain

The functional assay system for ITIM activity was the same as that described in Example 6, which comprises a modified method using T cells as recipient cells and features determination of luciferase activity under the control of NFAT cascade (Fry A M, Lanier L L, Weiss A., J Exp Med. (1996), 184, 295-300).

The known CD8α chain gene was cloned using resting CD8+ Marathon cDNA library (Clontech) as a template. PCR was carried out under the following reaction conditions.

```
Primers:
CD01 (5'-GAATTCATGGCCTTACCAGTGACCGC-3'/
SEQ ID NO: 47)<=>CD02 (5'-GGATCCTTAGACGTATCTCGCCGA
AA-3'/SEQ ID NO: 48)
```

Reaction Conditions:
94° C. for 30 seconds;
30 cycles of 94° C. for 15 seconds, 50° C. for 30 seconds, and 72° C. for 30 seconds; and
72° C. for 4 minutes.

PCR was carried out using GC polymerase (Takara Shuzo). A 0.7-kb fragment was separated by agarose gel electrophoresis, and then purified using QIAquick (QIAGEN). The purified product was cloned into pCR2.1-TOPO, and introduced into *E. coli* TOP10F'. Plasmid was prepared from the transformant using QIAprep (QIAGEN) kit, and a clone comprising a PCR error-free sequence (pCD8full0113) was selected and used in the subsequent analyses.

Example 13

Construction of Expression Vector for CD8-NKIR Fusion Protein

An expression vector for fusion protein of the cytoplasmic ITIM motif of NKIR and the extracellular domain of CD8α chain obtained in Example 12 was constructed by the following procedure.

First, fusion PCR was carried out under the following reaction conditions.
1st Round PCR A

```
Template:
pCD8full0113

Primers:
CD03 (5'-GGAATTCCACCATGGCCTTACCAGTGACCGC-3'/
SEQ ID NO: 49)<=>CDNKIR12 (5'-ACCAGCCAGTTGCTGGCGGG
GTCCAGCCCCCTCGTGTGCA-3'/SEQ ID NO: 50)
```

1st Round PCR B

```
Template: pBSNKIR224
Primers: CDNKIR11
(5'-TGCACACGAGGGGGCTGGACCCCGCCAGCAACTGGCTGGT-3')/

SEQ ID NO: 51) <=> T3 + (SEQ ID NO: 44)
```

The conditions used for both reactions are as follows:
94° C. for 30 seconds,
30 cycles of 94° C. for 15 seconds, 55° C. for 30 seconds, and 72° C. for 1 minute; and
72° C. for 4 minutes.

PCR was carried out using GC polymerase (Takara Shuzo). 0.5- and 0.6-kb fragments derived from PCR A and B, respectively, were separated by agarose gel electrophoresis, and then purified using QIAquick (QIAGEN). A 10-µl aliquot of each purified product (50 µl) was used as a template in the second round PCR described below. Template: 10 µl each of the products of PCR A and B described above The reaction conditions used are as follows:
94° C. for 30 seconds; and
15 cycles of 94° C. for 15 seconds, 55° C. for 30 seconds, and 72° C. for 90 seconds.

After reaction, the primers described below were added to 50 µl of the reaction mixture at the final concentration of 1 µM.
Primers: CD03<=>T3+
Reaction Conditions:
94° C. for 30 seconds;
35 cycles of 94° C. for 15 seconds, 55° C. for 30 seconds, and 72° C. for 30 seconds; and
72° C. for 4 minutes.

A 1.1-kb fragment was separated by agarose gel electrophoresis, and then purified using QIAquick (QIAGEN). The fragment was cloned into pCR2.1-TOPO, and introduced into *E. coli* TOP10F'. Plasmid was prepared from the transformant using QIAprep (QIAGEN) kit, and a clone comprising a PCR error-free sequence (pTOPOCD8NKIRfull) was selected and used in the subsequent analyses.

Next, 1 µg each of pCXND3 and pTOPOCD8NKIRfull were digested with 20 units each of EcoRI and NotI at 37° C. for one hour, and then electrophoresed in an agarose gel. The resulting 7.8- and 1.1-kb fragments were purified using QIAquick Gel Extraction kit (QIAGEN). Then, ligation was carried out using a 1-µl aliquot of each eluate (40 µl) and LigaFAST Ligation kit (Promega) and introduced into *E. coli* strain DH5α. Ampicillin-resistant strains were saved, and the clone pCXND3CD8NKIRfull of interest that was found to carry a 1.1-kb insert was used in the subsequent analyses.

Example 14

Construction of Expression Vector for CD8-KIR Fusion Protein

An expression vector for the fusion protein between the cytoplasmic ITIM motif of KIR and the extracellular domain of CD8α chain obtained in Example 12 was constructed by the following procedure. The construct is used as a positive control in the ITIM functional assay.

First, fusion PCR was carried out under the following reaction conditions.
1st Round PCR A
Template: pCD8full0113

```
Primers:
CD03 (SEQ ID NO: 49)<=>CDKIR12 (5'-ATCAGAACATGCAGG
TGTCTTCCAGCCCCCTCGTGTGCA-3')/SEQ ID NO: 52)
```

1st Round PCR B
Template: pBSKIR306

```
Primers:
CDKIR11 (5'-TGCACACGAGGGGGCTGGACAGACACCTGCATGTTCTG
AT-3')/SEQ ID NO: 53)<=>T3+ (SEQ ID NO: 44)
```

The conditions used for both reactions are as follows:
94° C. for 30 seconds;
30 cycles of 94° C. for 15 seconds, 55° C. for 30 seconds, and 72° C. for 1 minute; and
72° C. for 4 minutes.

PCR was carried out using GC polymerase (Takara Shuzo). 0.5- and 0.4-kb fragments derived from PCR A and B, respectively, were separated by agarose gel electrophoresis, and then purified using QIAquick (QIAGEN). A 10-μl aliquot of each purified product (50 μl) was used as a template in the second round PCR described below.
Template: 10 μl each of the products of PCR A and B described above
The reaction conditions used are as follows:
94° C. for 30 minutes; and
15 cycles of 94° C. for 15 seconds, 55° C. for 30 seconds, and 72° C. for 90 seconds.

After reaction, the primers described below were added to 50 μl of the reaction mixture at the final concentration of 1 μM.
Primers: CD03<=>T3+
Reaction Conditions:
94° C. for 30 seconds;
35 cycles of 94° C. for 15 seconds, 55° C. for 30 seconds, and 72° C. for 30 seconds; and
72° C. for 4 minutes.

A 0.9-kb fragment was separated by agarose gel electrophoresis, and purified using QIAquick (QIAGEN). The fragment was cloned into pCR2.1-TOPO, and introduced into *E. coli* TOP10F'. Plasmid was prepared from the transformant using QIAprep (QIAGEN) kit. The 0.9-kb EcoRI-NotI insertion fragment from a clone comprising a PCR error-free sequence was inserted between EcoRI and NotI sites of pCXND3, and the resulting pCXND3CD8KIRfull was used in the subsequent analyses.

Example 15

Establishment of a Cell Line Stably Expressing NFAT-luciferase Reporter

Transformation was carried out by electroporation using the luciferase reporter plasmid pNFATlucZEOF324 obtained in Example 9 as donor DNA and Jurkat cell line as recipient cells. 20 μg of the donor DNA was pre-digested with 20 units of PvuII (TaKaRa) at 37° C. for 1 hour. After chloroform/phenol treatment followed by ethanol precipitation, the DNA was dissolved in 20 μl of sterilized water. As recipient cells, Jurkat cells were passaged in RPMI1640 medium containing 10% FCS, washed with potassium-based phosphate buffered saline (K-PBS), and suspended in K-PBS at the cell density of $10^7$ cells/ml to prepare 0.8 ml of a cell suspension. Electroporation was carried out using Gene Pulsar II (Bio-Rad) under the condition of 0.3 kV and 950 μFD. After pulse application, the cells were suspended in 48 ml of passaging medium and cultured overnight under a condition without selective pressure. Then, a candidate cell line for the stable transformant was obtained under a selective pressure using zeocin (Invitrogen) at a final concentration of 100 μg/ml. Genomic DNA was prepared from the zeocin-resistant strain using DNeasy Tissue Kit (QIAGEN). PCR was carried out using a 5-μl aliquot of the final eluate (0.4 ml). Premix ExTaq was used as the PCR polymerase. Luc01 (5'-TTCATACAGAAG-GCGTGGAG-3'/SEQ ID NO: 45) and Luc02 (5'-CGT-TCGCGGGCGCAACTGCA-3'/SEQ ID NO: 46) were used as primers. The reaction was carried out under conditions of: denaturation at 94° C. for 5 minutes; 25 cycles of 94° C. for 15 seconds, 55° C. for 30 seconds, and 72° C. for 45 seconds; followed by extension at 72° C. for 5 minutes. Clones which gave a 0.5-kb PCR fragment in agarose gel electrophoresis were selected to use in the final screening by detecting luciferase activity.

A candidate cell line for the stable transformant with pNFATlucZEOF324, which was obtained from the Jurkat cell line, was suspended at the concentration of $6.7 \times 10^4$ cells/ml in a passaging medium containing 100 μg/ml zeocin. A 75-μl aliquot of the cells was plated into each well of anti-human CD3-coated microtiterplates (Beckton Dickinson) and non-coated immunomicroplates to carry out luciferase assay. After 20 hours of cultivation at 37° C., an equal volume (75 μl) of Dual-Glo Luciferase Reagent (Promega) was added to each well. The samples were allowed to stand for 10 minutes, and then the chemiluminescence was measured using the luminometer MicroLumat LB96P (EG&G Berthold) for 5 seconds for each well.

The F11 strain that exhibited intense chemiluminescence only when cultured in anti-human CD3-coated microtiterplates was selected as a stable transformant.

Example 16

Preparation of Dual Transformant

F11 strain obtained in Example 15 as a recipient cell was transformed with pCXND3CD8NKIRfull for CD8-NKIR fusion obtained in Example 13 and pCXND3CD8KIRfull for CD8-KIR fusion obtained in Example 14 to yield a dual transformant.

20 μg each of pCXND3CD8NKIRfull and pCXND3CD8KIRfull were digested with 20 units of PvuI (Takara Shuzo) at 37° C. from 2 hours. The digests were purified by treatment with an equal volume of phenol/chloroform (50% (v/v); Nacalai Tesque). The DNAs were precipitated using 1/10 volume of 3 M sodium acetate (Nacalai Tesque) and two volumes of ethanol (Nacalai Tesque), and then dried and dissolved in 20 μl of sterilized water. Electroporation and subsequent establishment were achieved under the same condition as that described in Example 9, except for using as a passaging medium RPMI 1640 medium containing 100 μg/ml zeocin, 10% (v/v) inactivated calf serum, and 1% (v/v) penicillin and streptomycin solutions and as a selection agent 700 μg/ml geneticin. The drug-resistant clones obtained from single colonies were analyzed by FACS using anti-CD8-FITC antibody (Becton Dickinson), and 6 to 8 expression clones were selected for each.

Figures 1, 11:
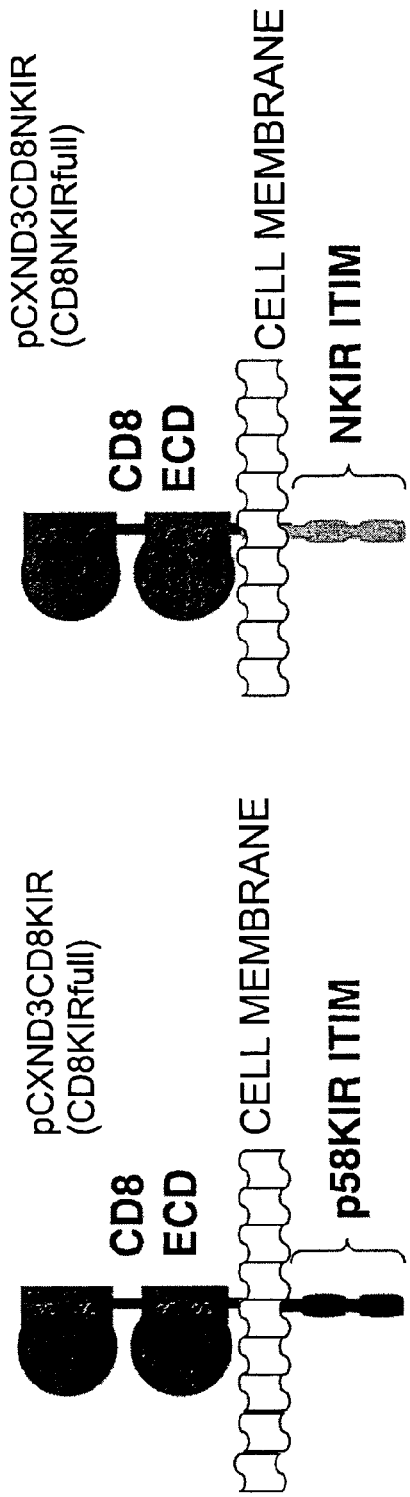
Figures 2, 11:
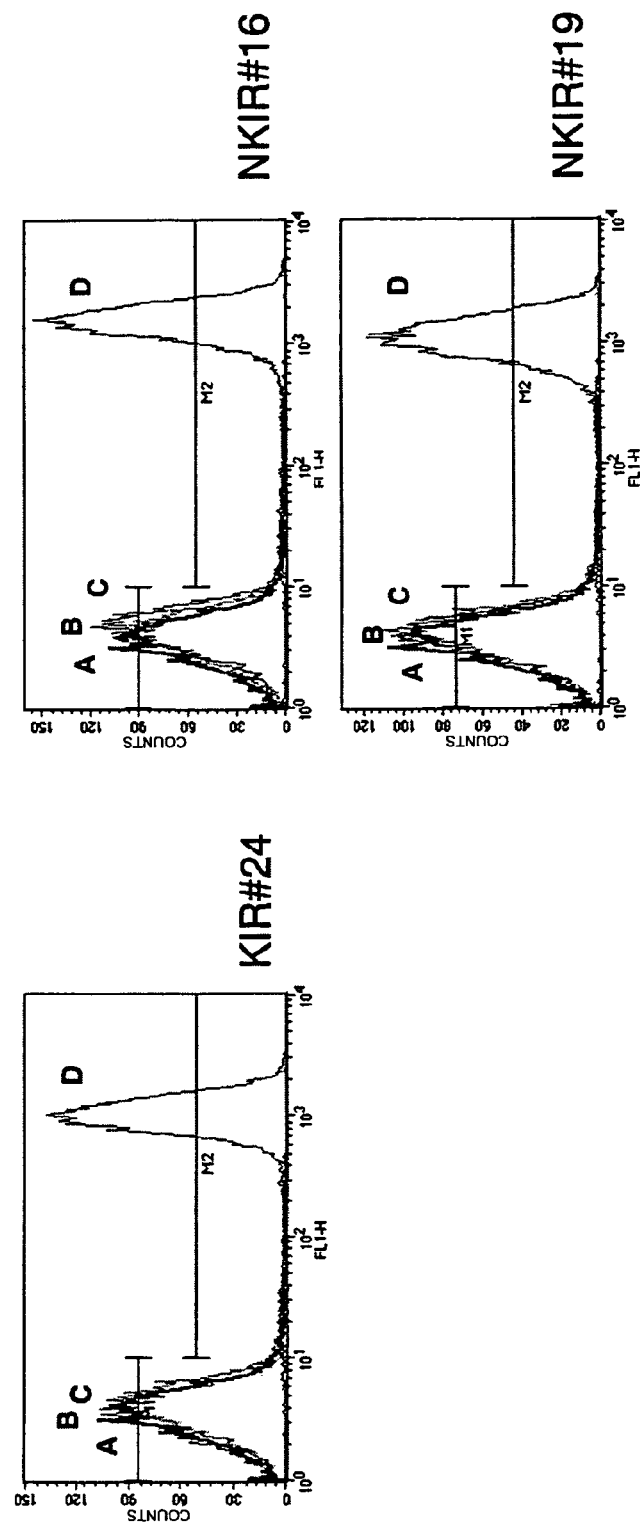

Three CD8 chimeric clones (NKIR#16 and NKIR#19 as transformants with pCXND3CD8NKIRfull; and KIR#24 as a transformant with pCXND3CD8KIRfull) exhibiting reporter activity were finally selected from the transformant cell lines by the reporter activity assay described in Example 15. The structures of the three CD8 chimeric clones are shown in FIG. 11-1. FIG. 11-2 shows a result of FACS analysis of these clones using anti-CD8 antibody, LT8 (Serotec), and FITC-conjugated goat anti-mouse IgG antibody (Coulter) to be used in Example 17. All three CD8 chimeric clones were found to be stained specifically with LT8.

Example 17

Assay of NKIR-derived ITIM Activity

A luciferase reporter assay for NKIR-derived ITIM activity was carried out using the dual transformants NKIR#16, NKIR#19, and KIR#24 obtained in Example 16 and the host F11 strain.

The host F11 strain was grown in a passaging medium (RPMI 1640 medium containing 100 μg/ml zeocin, 10% (v/v) inactivated calf serum, and 1% (v/v) penicillin and streptomycin solutions). The CD8 chimeric clones were grown in the above-described culture medium containing 700 μg/ml geneticin. The cells were suspended in each of the growth media at the cell density of $5.33 \times 10^5$ cells/ml. The suspensions were aliquoted into flat-bottomed 96-well plates (37.5 μl/well), and cultured at 37° C. for 16 hours. 12.5 μl aliquots (final concentration of 1.5 μg/ml) of anti-CD8 antibody (LT8, Serotec, MCA1226XZ) diluted to 6 μg/ml with each of the growth media were added as the primary antibody to the wells. Each growth medium containing no antibody was added to the control group. After 1 hour of culture at 37° C., 12.5 μl aliquots (final concentration of 1.2 μg/ml) of rabbit anti-mouse IgG1 antibody (H143.225.8, Southern Biotech, 1145-01) diluted to 6 μg/ml with each medium were added as a cross-linker to the wells. Each growth medium containing no antibody was added to the control group. After 1 hour of cultivation at 37° C., 12.5 μl aliquots (final concentration of 40 μg/ml) of ConA (SIGMA) diluted to 240 μg/ml with each growth medium were added thereto. After 8 or 10 hours of cultivation at 37° C., an equal volume (75 μl) of luciferase reagent (Promega) was added to each well, and the resulting mixtures were allowed to stand at room temperature for 10 minutes. Then, the luminescence was measured by the same procedure as described in Example 15.

Figure 12:
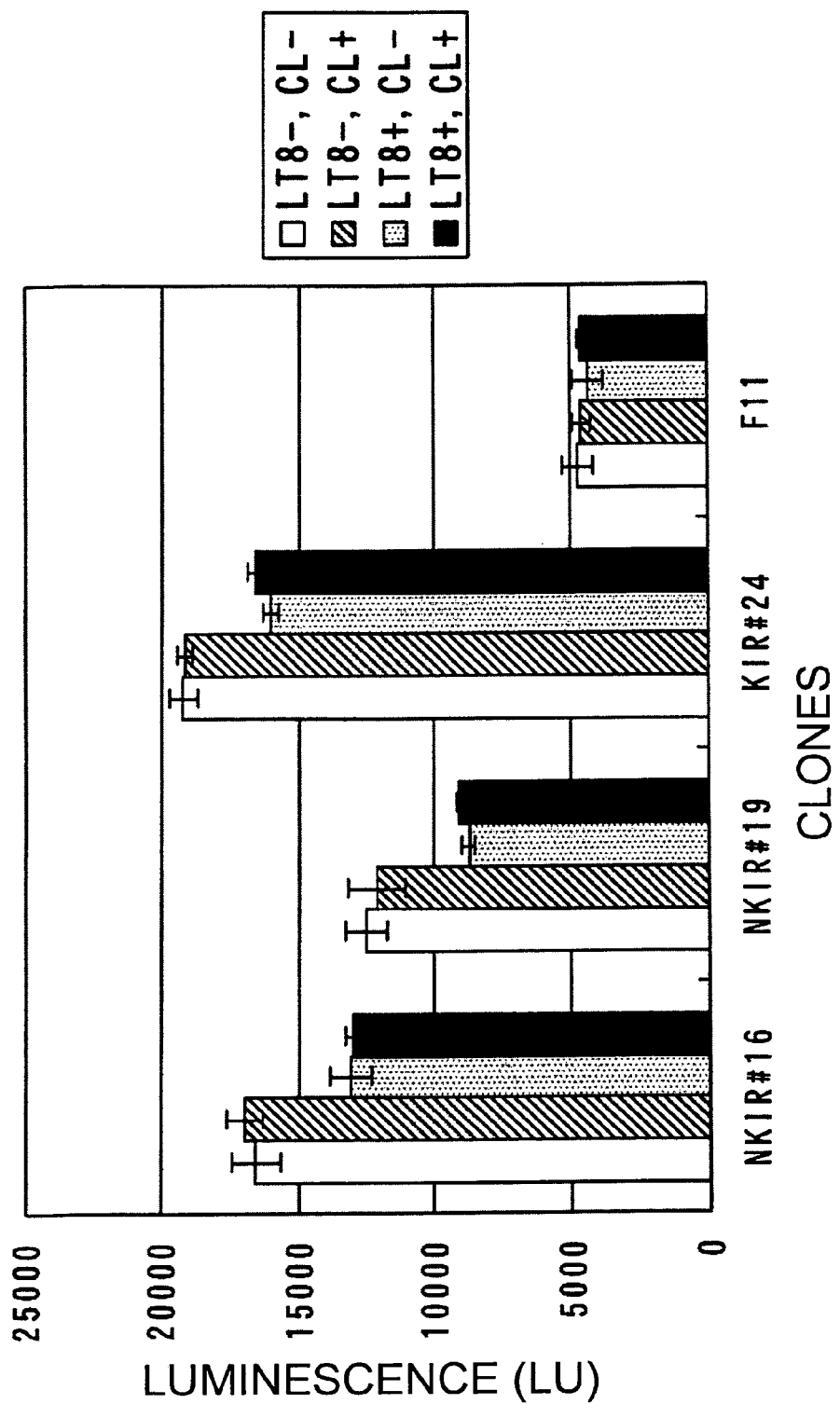
FIG. 12 is a histogram showing a result of a determination of ITIM function activity using the reporter assay described in Example 17. LT8, anti-CD8 antibody (LT8); and CL, crosslinker (rat anti-mouse IgG1 antibody).

The result of the reporter assay is shown in FIG. 12. All assays were carried out in triplicats and the averages are shown in histograms. The SD values are indicated by error bars. When the results of 8 and 10 hours of ConA stimulation were compared, the effect after 10 hours was found to be higher. Nonetheless, since the two results had roughly the same tendency, the 10-hour Con A stimulation is specifically described below. The host F11 exhibited almost constant activity regardless of the presence of LT8 antibody or cross-linker. In contrast, the activity of CD8-KIRfull transformant CD8 chimeric clone KIR#24 (the positive control clone) was found to be reduced in the presence of LT8, and as was expected, the reduction in the activity was not influenced by the presence of the cross-linker. Meanwhile, both activities of the two CD8-NKIRfull-transfected CD8 chimeric clones were found to be reduced in the presence of LT8, and the reduction in the activity was not influenced by the cross-linker. While the degree of reduction for the CD-KIR transformant #24 positive control was 16.6%, that for the CD-NKIR transformants #16 and #19 was 21.2% and 30.2%, respectively. Thus, the sequence comprising the cytoplasmic ITIM motif of NKIR molecule was suggested to have ITIM activity identical to or greater than that of the known cytoplasmic ITIM of KIR2DL3 molecule.

Industrial Applicability

The present invention provides novel proteins expressed in NK cells, DNAs encoding the proteins, vectors comprising the DNAs, host cells containing the vectors, and methods for producing the proteins. The present invention also provides methods for identifying compounds which bind to the proteins or regulate the activity of the proteins. The proteins of the present invention and DNAs, and compounds that bind to the proteins of the present invention or regulate the activity of the proteins are expected to be applicable in the development of new preventive and therapeutic agents for diseases associated with the proteins of the present invention.

The invention claimed is:

1. A polypeptide conjugated to a label, wherein the polypeptide has a sequence comprising the amino acid sequence of SEQ ID NO:2, or the amino acid sequence encoded by SEQ ID NO: 3, beginning at nucleotide 88.

2. The polypeptide of claim 1, wherein the polypeptide has a sequence comprising the amino acid sequence of SEQ ID NO: 2.

3. The polypeptide of claim 1, wherein the, polypeptide has a sequence consisting of the amino acid sequence of SEQ ID NO: 2.

4. The polypeptide of claim 1, wherein the polypeptide has a sequence comprising the amino acid sequence encoded by SEQ ID NO: 3, beginning at nucleotide 88.

5. The polypeptide of claim 1, wherein the polypeptide has a sequence consisting of the amino acid sequence encoded by SEQ ID NO: 3, beginning at nucleotide 88.

6. The polypeptide of claim 1, wherein the label is selected from the group consisting of: a radioisotope, a fluorophore, biotin, and avidin.

7. A method for producing the polypeptide of claim 1, the method comprising:
   providing a host cell transformed with a DNA encoding the polypeptide;
   culturing the host cell, and
   collecting the polypeptide from the host cell or a culture supernatant thereof.

8. A method for identifying a potential ligand for the polypeptide of claim 1, the method comprising:
   (a) contacting a candidate compound with the polypeptide or a cell expressing the polypeptide; and
   (b) determining whether the candidate compound binds to the polypeptide or cell, wherein binding to the polypeptide or cell is an indication that the candidate compound is a potential ligand for the polypeptide.

9. A method for identifying a potential agonist for the polypeptide of claim 1, wherein the method comprises:
   (a) contacting a candidate compound with a cell expressing the polypeptide; and
   (b) determining whether the candidate compound induces the polypeptide to generate an ITIM signal activity, wherein the activity is an indication that the candidate compound is a potential agonist for the polypeptide.

10. A method for identifying a potential antagonist for the polypeptide of claim 1, wherein the method comprises:
   (a) contacting a candidate compound with a cell expressing the polypeptide; and
   (b) determining whether an ITIM signal activity is reduced as compared with the activity in the absence of the candidate compound, wherein a reduction in activity is an indication that the candidate compound is a potential antagonist for the polypeptide.

11. A fusion protein comprising:
   a first sequence that is the amino acid sequence of SEQ ID NO: 2 or the amino acid sequence encoded by SEQ ID NO: 3, beginning at nucleotide 88; and
   a second sequence that is an amino acid sequence of another protein or peptide.

12. The fusion protein of claim 11, wherein the first sequence is the amino acid sequence of SEQ ID NO: 2.

13. The fusion protein of claim 11, wherein the first sequence is the amino acid sequence encoded by SEQ ID NO: 3, beginning at nucleotide 88.

14. The fusion protein of claim 11, wherein the second sequence is another peptide selected from the group consisting of: a polyhistidine tag, a human c-myc fragment, a FLAG tag, a vesicular stomatitis virus glycoprotein (VSV-GP) fragment, T7 gene 10 protein tag, human herpes simplex virus glycoprotein (HSV) tag, a p18 human immunodeficiency virus (HIV) fragment, SV40 T antigen fragment, a lymphocyte specific protein tyrosine kinase p56 (lck) tag, an α-tubulin fragment, a B-tag, and a protein C fragment.

15. The fusion protein of claim 11, wherein the second sequence is another protein selected from the group consisting of: glutathione-S-transferase, influenza agglutinin, an immunoglobulin constant region, β-galactosidase, maltose-binding protein, and green fluorescence protein.

16. A method for producing the fusion protein of claim 11, the method comprising:
   providing a host cell transformed with a DNA encoding the fusion protein;
   culturing the host cell, and
   collecting the fusion protein from the host cell or a culture supernatant thereof.

17. A method for identifying a potential ligand for the fusion protein of claim 11, the method comprising:
   (a) contacting a candidate compound with the fusion protein or a cell expressing the fusion protein; and
   (b) determining whether the candidate compound binds to the fusion protein or cell, wherein binding to the fusion protein or cell is an indication that the candidate compound is a potential ligand for the fusion protein.

18. A method for identifying a potential agonist for the fusion protein of claim 11, wherein the method comprises:
   (a) contacting a candidate compound with a cell expressing the fusion protein; and
   (b) determining whether the candidate compound induces the fusion protein to generate an ITIM signal activity, wherein the activity is an indication that the candidate compound is a potential agonist for the fusion protein.

19. A method for identifying a potential antagonist for the fusion protein of claim 11, wherein the method comprises:
   (a) contacting a candidate compound with a cell expressing the fusion protein; and
   (b) determining whether an ITIM signal activity is reduced as compared with the activity in the absence of the candidate compound, wherein a reduction in activity is an indication that the candidate compound is a potential antagonist for the fusion protein.

* * * * *

SEQUENCE LISTING

```
<160> NUMBER OF SEQ ID NOS: 53

<210> SEQ ID NO 1
<211> LENGTH: 1473
<212> TYPE: DNA
<213> ORGANISM: Homo sapiens
<220> FEATURE:
<221> NAME/KEY: CDS
<222> LOCATION: (87)..(1376)

<400> SEQUENCE: 1
acacacccac aggacctgca gctgaacgaa gttgaagaca actcaggaga tctgttggaa      60
agagaacgat agaggaaaat atatga atg ttg cca tct tta gtt ccc tgt gtt     113
                             Met Leu Pro Ser Leu Val Pro Cys Val
                              1               5 ggg aaa act gtc tgg ctg tac ctc caa gcc tgg cca aac cct gtg ttt     161
Gly Lys Thr Val Trp Leu Tyr Leu Gln Ala Trp Pro Asn Pro Val Phe
 10              15                  20                  25 gaa gga gat gcc ctg act ctg cga tgt cag gga tgg aag aat aca cca     209
Glu Gly Asp Ala Leu Thr Leu Arg Cys Gln Gly Trp Lys Asn Thr Pro
                 30                  35                  40
```

```
ctg tct cag gtg aag ttc tac aga gat gga aaa ttc ctt cat ttc tct    257
Leu Ser Gln Val Lys Phe Tyr Arg Asp Gly Lys Phe Leu His Phe Ser
            45                  50                  55 aag gaa aac cag act ctg tcc atg gga gca gca aca gtg cag agc cgt    305
Lys Glu Asn Gln Thr Leu Ser Met Gly Ala Ala Thr Val Gln Ser Arg
        60                  65                  70 ggc cag tac agc tgc tct ggg cag gtg atg tat att cca cag aca ttc    353
Gly Gln Tyr Ser Cys Ser Gly Gln Val Met Tyr Ile Pro Gln Thr Phe
    75                  80                  85 aca caa act tca gag act gcc atg gtt caa gtc caa gag ctg ttt cca    401
Thr Gln Thr Ser Glu Thr Ala Met Val Gln Val Gln Glu Leu Phe Pro
90                  95                  100                 105 cct cct gtg ctg agt gcc atc ccc tct cct gag ccc cga gag ggt agc    449
Pro Pro Val Leu Ser Ala Ile Pro Ser Pro Glu Pro Arg Glu Gly Ser
                110                 115                 120 ctg gtg acc ctg aga tgt cag aca aag ctg cac ccc ctg agg tca gcc    497
Leu Val Thr Leu Arg Cys Gln Thr Lys Leu His Pro Leu Arg Ser Ala
            125                 130                 135 ttg agg ctc ctt ttc tcc ttc cac aag gac ggc cac acc ttg cag gac    545
Leu Arg Leu Leu Phe Ser Phe His Lys Asp Gly His Thr Leu Gln Asp
        140                 145                 150 agg ggc cct cac cca gaa ctc tgc atc ccg gga gcc aag gag gga gac    593
Arg Gly Pro His Pro Glu Leu Cys Ile Pro Gly Ala Lys Glu Gly Asp
    155                 160                 165 tct ggg ctt tac tgg tgt gag gtg gcc cct gag ggt ggc cag gtc cag    641
Ser Gly Leu Tyr Trp Cys Glu Val Ala Pro Glu Gly Gly Gln Val Gln
170                 175                 180                 185 aag cag agc ccc cag ctg gag gtc aga gtg cag gct cct gta tcc cgt    689
Lys Gln Ser Pro Gln Leu Glu Val Arg Val Gln Ala Pro Val Ser Arg
                190                 195                 200 cct gtg ctc act ctg cac cac ggg cct gct gac cct gct gtg ggg gac    737
Pro Val Leu Thr Leu His His Gly Pro Ala Asp Pro Ala Val Gly Asp
            205                 210                 215 atg gtg cag ctc ctc tgt gag gca cag agg ggc tcc cct ccg atc ctg    785
Met Val Gln Leu Leu Cys Glu Ala Gln Arg Gly Ser Pro Pro Ile Leu
        220                 225                 230 tat tcc ttc tac ctt gat gag aag att gtg ggg aac cac tca gct ccc    833
Tyr Ser Phe Tyr Leu Asp Glu Lys Ile Val Gly Asn His Ser Ala Pro
    235                 240                 245 tgt ggt gga acc acc tcc ctc ctc ttc cca gtg aag tca gaa cag gat    881
Cys Gly Gly Thr Thr Ser Leu Leu Phe Pro Val Lys Ser Glu Gln Asp
250                 255                 260                 265 gct ggg aac tac tcc tgc gag gct gag aac agt gtc tcc aga gag agg    929
Ala Gly Asn Tyr Ser Cys Glu Ala Glu Asn Ser Val Ser Arg Glu Arg
                270                 275                 280 agt gag ccc aag aag ctg tct ctg aag ggt tct caa gtc ttg ttc act    977
Ser Glu Pro Lys Lys Leu Ser Leu Lys Gly Ser Gln Val Leu Phe Thr
            285                 290                 295 ccc gcc agc aac tgg ctg gtt cct tgg ctt cct gcg agc ctg ctt ggc    1025
Pro Ala Ser Asn Trp Leu Val Pro Trp Leu Pro Ala Ser Leu Leu Gly
        300                 305                 310 ctg atg gtt att gct gct gca ctt ctg gtt tat gtg aga tcc tgg aga    1073
Leu Met Val Ile Ala Ala Ala Leu Leu Val Tyr Val Arg Ser Trp Arg
    315                 320                 325 aaa gct ggg ccc ctt cca tcc cag ata cca ccc aca gct cca ggt gga    1121
Lys Ala Gly Pro Leu Pro Ser Gln Ile Pro Pro Thr Ala Pro Gly Gly
330                 335                 340                 345 gag cag tgc cca cta tat gcc aac gtg cat cac cag aaa ggg aaa gat    1169
Glu Gln Cys Pro Leu Tyr Ala Asn Val His His Gln Lys Gly Lys Asp
```

```
                        350                 355                 360
gaa ggt gtt gtc tac tct gtg gtg cat aga acc tca aag agg agt gaa         1217
Glu Gly Val Val Tyr Ser Val Val His Arg Thr Ser Lys Arg Ser Glu
            365                 370                 375 gcc agg tct gct gag ttc acc gtg ggg aga aag gac agt tct atc atc         1265
Ala Arg Ser Ala Glu Phe Thr Val Gly Arg Lys Asp Ser Ser Ile Ile
            380                 385                 390 tgt gcg gag gtg aga tgc ctg cag ccc agt gag gtt tca tcc acg gag         1313
Cys Ala Glu Val Arg Cys Leu Gln Pro Ser Glu Val Ser Ser Thr Glu
    395                 400                 405 gtg aat atg aga agc agg act ctc caa gaa ccc ctt agc gac tgt gag         1361
Val Asn Met Arg Ser Arg Thr Leu Gln Glu Pro Leu Ser Asp Cys Glu
410                 415                 420                 425 gag gtt ctc tgc tag tgatggtgtt ctcctatcaa cacacgccca ccccagtct          1416
Glu Val Leu Cys ccagtgctcc tcaggaagac agtggggtcc tcaactcttt ctgtgggtcc ttcagtg          1473

<210> SEQ ID NO 2
<211> LENGTH: 429
<212> TYPE: PRT
<213> ORGANISM: Homo sapiens

<400> SEQUENCE: 2

Met Leu Pro Ser Leu Val Pro Cys Val Gly Lys Thr Val Trp Leu Tyr
1               5                   10                  15

Leu Gln Ala Trp Pro Asn Pro Val Phe Glu Gly Asp Ala Leu Thr Leu
                20                  25                  30

Arg Cys Gln Gly Trp Lys Asn Thr Pro Leu Ser Gln Val Lys Phe Tyr
            35                  40                  45

Arg Asp Gly Lys Phe Leu His Phe Ser Lys Glu Asn Gln Thr Leu Ser
        50                  55                  60

Met Gly Ala Ala Thr Val Gln Ser Arg Gly Gln Tyr Ser Cys Ser Gly
65                  70                  75                  80

Gln Val Met Tyr Ile Pro Gln Thr Phe Thr Gln Ser Glu Thr Ala
                85                  90                  95

Met Val Gln Val Gln Glu Leu Phe Pro Pro Val Leu Ser Ala Ile
                100                 105                 110

Pro Ser Pro Glu Pro Arg Glu Gly Ser Leu Val Thr Leu Arg Cys Gln
            115                 120                 125

Thr Lys Leu His Pro Leu Arg Ser Ala Leu Arg Leu Leu Phe Ser Phe
        130                 135                 140

His Lys Asp Gly His Thr Leu Gln Asp Arg Gly Pro His Pro Glu Leu
145                 150                 155                 160

Cys Ile Pro Gly Ala Lys Glu Gly Asp Ser Gly Leu Tyr Trp Cys Glu
                165                 170                 175

Val Ala Pro Glu Gly Gly Gln Val Gln Lys Gln Ser Pro Gln Leu Glu
            180                 185                 190

Val Arg Val Gln Ala Pro Val Ser Arg Pro Val Leu Thr Leu His His
        195                 200                 205

Gly Pro Ala Asp Pro Ala Val Gly Asp Met Val Gln Leu Leu Cys Glu
    210                 215                 220

Ala Gln Arg Gly Ser Pro Pro Ile Leu Tyr Ser Phe Tyr Leu Asp Glu
225                 230                 235                 240

Lys Ile Val Gly Asn His Ser Ala Pro Cys Gly Gly Thr Ser Leu
                245                 250                 255
```

-continued

```
Leu Phe Pro Val Lys Ser Glu Gln Asp Ala Gly Asn Tyr Ser Cys Glu
                260                 265                 270

Ala Glu Asn Ser Val Ser Arg Glu Arg Ser Pro Lys Lys Leu Ser
            275                 280                 285

Leu Lys Gly Ser Gln Val Leu Phe Thr Pro Ala Ser Asn Trp Leu Val
        290                 295                 300

Pro Trp Leu Pro Ala Ser Leu Leu Gly Leu Met Val Ile Ala Ala Ala
305                 310                 315                 320

Leu Leu Val Tyr Val Arg Ser Trp Arg Lys Ala Gly Pro Leu Pro Ser
                325                 330                 335

Gln Ile Pro Pro Thr Ala Pro Gly Gly Glu Gln Cys Pro Leu Tyr Ala
                340                 345                 350

Asn Val His His Gln Lys Gly Lys Asp Glu Gly Val Val Tyr Ser Val
            355                 360                 365

Val His Arg Thr Ser Lys Arg Ser Glu Ala Arg Ser Ala Glu Phe Thr
        370                 375                 380

Val Gly Arg Lys Asp Ser Ser Ile Ile Cys Ala Glu Val Arg Cys Leu
385                 390                 395                 400

Gln Pro Ser Glu Val Ser Ser Thr Glu Val Asn Met Arg Ser Arg Thr
                405                 410                 415

Leu Gln Glu Pro Leu Ser Asp Cys Glu Glu Val Leu Cys
            420                 425

<210> SEQ ID NO 3
<211> LENGTH: 2005
<212> TYPE: DNA
<213> ORGANISM: Homo sapiens
<220> FEATURE:
<221> NAME/KEY: CDS
<222> LOCATION: (88)..(1410)

<400> SEQUENCE: 3
cacacaccca caggacctgc agctgaacga agttgaagac aactcaggag atctgttgga      60
aagagaacga tagaggaaaa tatatga atg ttg cca tct tta ggc ccc atg ctg    114
                              Met Leu Pro Ser Leu Gly Pro Met Leu
                                1               5 ctc tgg acg gct gtg ctg ctc ttt gtt ccc tgt gtt ggg aaa act gtc      162
Leu Trp Thr Ala Val Leu Leu Phe Val Pro Cys Val Gly Lys Thr Val
 10              15                  20                  25 tgg ctg tac ctc caa gcc tgg cca aac cct gtg ttt gaa gga gat gcc      210
Trp Leu Tyr Leu Gln Ala Trp Pro Asn Pro Val Phe Glu Gly Asp Ala
                 30                  35                  40 ctg act ctg cga tgt cag gga tgg aag aat aca cca ctg tct cag gtg      258
Leu Thr Leu Arg Cys Gln Gly Trp Lys Asn Thr Pro Leu Ser Gln Val
             45                  50                  55 aag ttc tac aga gat gga aaa ttc ctt cat ttc tct aag gaa aac cag      306
Lys Phe Tyr Arg Asp Gly Lys Phe Leu His Phe Ser Lys Glu Asn Gln
         60                  65                  70 act ctg tcc atg gga gca gca aca gtg cag agc cgt ggc cag tac agc      354
Thr Leu Ser Met Gly Ala Ala Thr Val Gln Ser Arg Gly Gln Tyr Ser
     75                  80                  85 tgc tct ggg cag gtg atg tat att cca cag aca ttc aca caa act tca      402
Cys Ser Gly Gln Val Met Tyr Ile Pro Gln Thr Phe Thr Gln Thr Ser
 90                  95                 100                 105 gag act gcc atg gtt caa gtc caa gag ctg ttt cca cct cct gtg ctg      450
Glu Thr Ala Met Val Gln Val Gln Glu Leu Phe Pro Pro Pro Val Leu
                110                 115                 120 agt gcc atc ccc tct cct gag ccc cga gag ggt agc ctg gtg acc ctg      498
```

```
                Ser Ala Ile Pro Ser Pro Glu Pro Arg Glu Gly Ser Leu Val Thr Leu
                            125                 130                 135 aga tgt cag aca aag ctg cac ccc ctg agg tca gcc ttg agg ctc ctt          546
Arg Cys Gln Thr Lys Leu His Pro Leu Arg Ser Ala Leu Arg Leu Leu
            140                 145                 150 ttc tcc ttc cac aag gac ggc cac acc ttg cag gac agg ggc cct cac          594
Phe Ser Phe His Lys Asp Gly His Thr Leu Gln Asp Arg Gly Pro His
155                 160                 165 cca gaa ctc tgc atc ccg gga gcc aag gag gga gac tct ggg ctt tac          642
Pro Glu Leu Cys Ile Pro Gly Ala Lys Glu Gly Asp Ser Gly Leu Tyr
170                 175                 180                 185 tgg tgt gag gtg gcc cct gag ggt ggc cag gtc cag aag cag agc ccc          690
Trp Cys Glu Val Ala Pro Glu Gly Gly Gln Val Gln Lys Gln Ser Pro
                190                 195                 200 cag ctg gag gtc aga gtg cag gct cct gta tcc cgt cct gtg ctc act          738
Gln Leu Glu Val Arg Val Gln Ala Pro Val Ser Arg Pro Val Leu Thr
            205                 210                 215 ctg cac cac ggg cct gct gac ccc gct gtg ggg gac atg gtg cag ctc          786
Leu His His Gly Pro Ala Asp Pro Ala Val Gly Asp Met Val Gln Leu
            220                 225                 230 ctc tgt gag gca cag agg ggc tcc cct ccg atc ctg tat tcc ttc tac          834
Leu Cys Glu Ala Gln Arg Gly Ser Pro Pro Ile Leu Tyr Ser Phe Tyr
235                 240                 245 ctt gat gag aag att gtg ggg aac cac tca gct ccc tgt ggt gga acc          882
Leu Asp Glu Lys Ile Val Gly Asn His Ser Ala Pro Cys Gly Gly Thr
250                 255                 260                 265 acc tcc ctc ctc ttc cca gtg aag tca gaa cag gat gct ggg aac tac          930
Thr Ser Leu Leu Phe Pro Val Lys Ser Glu Gln Asp Ala Gly Asn Tyr
                270                 275                 280 tcc tgc gag gct gag aac agt gtc tcc aga gag agg agt gag ccc aag          978
Ser Cys Glu Ala Glu Asn Ser Val Ser Arg Glu Arg Ser Glu Pro Lys
                285                 290                 295 aag ctg tct ctg aag ggt tct caa gtc ttg ttc act ccc gcc agc aac         1026
Lys Leu Ser Leu Lys Gly Ser Gln Val Leu Phe Thr Pro Ala Ser Asn
            300                 305                 310 tgg ctg gtt cct tgg ctt cct gcg agc ctg ctt ggc ctg atg gtt att         1074
Trp Leu Val Pro Trp Leu Pro Ala Ser Leu Leu Gly Leu Met Val Ile
315                 320                 325 gct gct gca ctt ctg gtt tat gtg aga tcc tgg aga aaa gct ggg ccc         1122
Ala Ala Ala Leu Leu Val Tyr Val Arg Ser Trp Arg Lys Ala Gly Pro
330                 335                 340                 345 ctt cca tcc cag ata cca ccc aca gct cca ggt gga gag cag tgc cca         1170
Leu Pro Ser Gln Ile Pro Pro Thr Ala Pro Gly Gly Glu Gln Cys Pro
                350                 355                 360 cta tat gcc aac gtg cat cac cag aaa ggg aaa gat gaa ggt gtt gtc         1218
Leu Tyr Ala Asn Val His His Gln Lys Gly Lys Asp Glu Gly Val Val
                365                 370                 375 tac tct gtg gtg cat aga acc tca aag agg agt gaa gcc agg tct gct         1266
Tyr Ser Val Val His Arg Thr Ser Lys Arg Ser Glu Ala Arg Ser Ala
            380                 385                 390 gag ttc acc gtg ggg aga aag gac agt tct atc atc tgt gcg gag gtg         1314
Glu Phe Thr Val Gly Arg Lys Asp Ser Ser Ile Ile Cys Ala Glu Val
            395                 400                 405 aga tgc ctg cag ccc agt gag gtt tca tcc acg gag gtg aat atg aga         1362
Arg Cys Leu Gln Pro Ser Glu Val Ser Ser Thr Glu Val Asn Met Arg
410                 415                 420                 425 agc agg act ctc caa gaa ccc ctt agc gac tgt gag gag gtt ctc tgc         1410
Ser Arg Thr Leu Gln Glu Pro Leu Ser Asp Cys Glu Glu Val Leu Cys
                430                 435                 440
```

-continued

```
tagtgatggt gttctcctat caacacacgc ccaccccag tctccagtgc tcctcaggaa  1470
gacagtgggg tcctcaactc tttctgtggg tccttcagtg tcccaagccc agcatcacag  1530
agccccctga gcccttgtcc tggtcaggag cacctgaacc ctgggttctt ttcttagcag  1590
aagaccaacc aatggaatgg aagggagat gctcccacca acacacacac ttaggttcaa  1650
tcagtgacac tggacacata agccacagat gtcttctttc catacaagca tgttagttcg  1710
ccccaatata catatatata tgaaatagtc atgtgccgca taacaacatt tcagtcagtg  1770
atagactgca tacacaacag tggtcccata agactgtaat ggagtttaaa aattcctact  1830
gcctagtgat atcatagttg ccttaacatc ataacacaac acatttctca cgcgtttgtg  1890
gtgatgctgg tacaaacaag ctacagcgcc gctagtcata tacaaatata gcacatacaa  1950
ttatgtacag tacactatac ttgataatga taataaacaa ctatgttact ggttt         2005
```

<210> SEQ ID NO 4
<211> LENGTH: 441
<212> TYPE: PRT
<213> ORGANISM: Homo sapiens

<400> SEQUENCE: 4

```
Met Leu Pro Ser Leu Gly Pro Met Leu Leu Trp Thr Ala Val Leu Leu
1               5                   10                  15

Phe Val Pro Cys Val Gly Lys Thr Val Trp Leu Tyr Leu Gln Ala Trp
            20                  25                  30

Pro Asn Pro Val Phe Glu Gly Asp Ala Leu Thr Leu Arg Cys Gln Gly
        35                  40                  45

Trp Lys Asn Thr Pro Leu Ser Gln Val Lys Phe Tyr Arg Asp Gly Lys
    50                  55                  60

Phe Leu His Phe Ser Lys Glu Asn Gln Thr Leu Ser Met Gly Ala Ala
65                  70                  75                  80

Thr Val Gln Ser Arg Gly Gln Tyr Ser Cys Ser Gly Gln Val Met Tyr
                85                  90                  95

Ile Pro Gln Thr Phe Thr Gln Thr Ser Glu Thr Ala Met Val Gln Val
            100                 105                 110

Gln Glu Leu Phe Pro Pro Val Leu Ser Ala Ile Pro Ser Pro Glu
        115                 120                 125

Pro Arg Glu Gly Ser Leu Val Thr Leu Arg Cys Gln Thr Lys Leu His
    130                 135                 140

Pro Leu Arg Ser Ala Leu Arg Leu Leu Phe Ser Phe His Lys Asp Gly
145                 150                 155                 160

His Thr Leu Gln Asp Arg Gly Pro His Pro Glu Leu Cys Ile Pro Gly
                165                 170                 175

Ala Lys Glu Gly Asp Ser Gly Leu Tyr Trp Cys Glu Val Ala Pro Glu
            180                 185                 190

Gly Gly Gln Val Gln Lys Gln Ser Pro Gln Leu Glu Val Arg Val Gln
        195                 200                 205

Ala Pro Val Ser Arg Pro Val Leu Thr Leu His His Gly Pro Ala Asp
    210                 215                 220

Pro Ala Val Gly Asp Met Val Gln Leu Leu Cys Glu Ala Gln Arg Gly
225                 230                 235                 240

Ser Pro Pro Ile Leu Tyr Ser Phe Tyr Leu Asp Glu Lys Ile Val Gly
                245                 250                 255

Asn His Ser Ala Pro Cys Gly Gly Thr Thr Ser Leu Leu Phe Pro Val
            260                 265                 270
```

```
Lys Ser Glu Gln Asp Ala Gly Asn Tyr Ser Cys Glu Ala Glu Asn Ser
            275                 280                 285

Val Ser Arg Glu Arg Ser Glu Pro Lys Lys Leu Ser Leu Lys Gly Ser
        290                 295                 300

Gln Val Leu Phe Thr Pro Ala Ser Asn Trp Leu Val Pro Trp Leu Pro
305                 310                 315                 320

Ala Ser Leu Leu Gly Leu Met Val Ile Ala Ala Leu Leu Val Tyr
                325                 330                 335

Val Arg Ser Trp Arg Lys Ala Gly Pro Leu Pro Ser Gln Ile Pro Pro
            340                 345                 350

Thr Ala Pro Gly Gly Glu Gln Cys Pro Leu Tyr Ala Asn Val His His
        355                 360                 365

Gln Lys Gly Lys Asp Glu Gly Val Val Tyr Ser Val His Arg Thr
    370                 375                 380

Ser Lys Arg Ser Glu Ala Arg Ser Ala Glu Phe Thr Val Gly Arg Lys
385                 390                 395                 400

Asp Ser Ser Ile Ile Cys Ala Glu Val Arg Cys Leu Gln Pro Ser Glu
            405                 410                 415

Val Ser Ser Thr Glu Val Asn Met Arg Ser Arg Thr Leu Gln Glu Pro
        420                 425                 430

Leu Ser Asp Cys Glu Glu Val Leu Cys
        435                 440

<210> SEQ ID NO 5
<211> LENGTH: 1543
<212> TYPE: DNA
<213> ORGANISM: Mus musculus
<220> FEATURE:
<221> NAME/KEY: CDS
<222> LOCATION: (115)..(921)

<400> SEQUENCE: 5
cacctcttaa gtcagaaggg ccaccactca cctccagctc agaactacca gtctctctct    60
ccccagcttc agctctgcct gctgtttggc ctgctctgcc tcaagaaagg cacc atg    117
                                                              Met
                                                              1 ctg ctc tgg atg gtt ctc ctg ctc tgt gat tcc atg gtt gaa gct caa    165
Leu Leu Trp Met Val Leu Leu Leu Cys Asp Ser Met Val Glu Ala Gln
        5                  10                  15 gag ttg ttc cca aat cct gag ctg aca gaa ttc acc aat tca gag acg    213
Glu Leu Phe Pro Asn Pro Glu Leu Thr Glu Phe Thr Asn Ser Glu Thr
    20                  25                  30 atg gat gtc atc ctg aag tgt acc ata aag gtg gac ccc aag aat cca    261
Met Asp Val Ile Leu Lys Cys Thr Ile Lys Val Asp Pro Lys Asn Pro
35                  40                  45 act tta cag ctc ttt tac act ttc tac aag gac aac cat gtc att caa    309
Thr Leu Gln Leu Phe Tyr Thr Phe Tyr Lys Asp Asn His Val Ile Gln
50                  55                  60                  65 gac agg agt ccc cac tca gta ttt tct gca gaa gcc aag gag gaa aac    357
Asp Arg Ser Pro His Ser Val Phe Ser Ala Glu Ala Lys Glu Glu Asn
                70                  75                  80 tct ggg ctc tac cag tgt atg gtg gac act gag gat ggc tta att cag    405
Ser Gly Leu Tyr Gln Cys Met Val Asp Thr Glu Asp Gly Leu Ile Gln
            85                  90                  95 aaa aaa agt ggc tat ctg gat atc cag ttc tgg act cct gta tcc cat    453
Lys Lys Ser Gly Tyr Leu Asp Ile Gln Phe Trp Thr Pro Val Ser His
        100                 105                 110 cct gtg ctc act ctg caa cat gaa gcc act aac ctt gct gta gga gac    501
Pro Val Leu Thr Leu Gln His Glu Ala Thr Asn Leu Ala Val Gly Asp
```

```
                Pro Val Leu Thr Leu Gln His Glu Ala Thr Asn Leu Ala Val Gly Asp
                    115                 120                 125 aag gtg gag ttc ctc tgt gag gcc cac cag ggc tcc ctt cca atc ttt          549
Lys Val Glu Phe Leu Cys Glu Ala His Gln Gly Ser Leu Pro Ile Phe
130                 135                 140                 145 tac tca ttc tac att aat gga gaa atc cta ggg aaa ccc ctg gct ccc          597
Tyr Ser Phe Tyr Ile Asn Gly Glu Ile Leu Gly Lys Pro Leu Ala Pro
                150                 155                 160 tct ggc aga gct gcc tcc ctc cta gcc tca gta aag gca gag tgg agt          645
Ser Gly Arg Ala Ala Ser Leu Leu Ala Ser Val Lys Ala Glu Trp Ser
            165                 170                 175 acc aag aac tat tcc tgt gaa gct aaa aac aac atc tcc aga gaa ata          693
Thr Lys Asn Tyr Ser Cys Glu Ala Lys Asn Asn Ile Ser Arg Glu Ile
        180                 185                 190 agt gag ctc aag aag ttc ccc ttg gtt gtc tca ggt act gcc tgg atc          741
Ser Glu Leu Lys Lys Phe Pro Leu Val Val Ser Gly Thr Ala Trp Ile
    195                 200                 205 aag agc aac atg cta act atc tgg cta cct gca agc ctg ctt gga ggg          789
Lys Ser Asn Met Leu Thr Ile Trp Leu Pro Ala Ser Leu Leu Gly Gly
210                 215                 220                 225 atg gtc att gcg gct gtg gtt cta atg tat ttc ttc aaa ccc tgt aaa          837
Met Val Ile Ala Ala Val Val Leu Met Tyr Phe Phe Lys Pro Cys Lys
                230                 235                 240 aag cat gcc aga cct gag atg ccc acc cta aaa gag cca gac agt ttt          885
Lys His Ala Arg Pro Glu Met Pro Thr Leu Lys Glu Pro Asp Ser Phe
            245                 250                 255 cta tat gta tcg gtt gat aat cga aga tat aaa tga gattcccacc              931
Leu Tyr Val Ser Val Asp Asn Arg Arg Tyr Lys
        260                 265 aatgatttgg attcaaaaac caggacctgc caagatcccc ttggtcttta ggatcatgct       991
ctgtgttagt gcaatgtctt cctccagcat atactcaact ccagctccca gcctccaccc      1051
tccagcactc agcagtggct ccaagttctc cctgcaggtc acccagttcc tagcccagca      1111
gtgaggaagc ccatatgctc tattcctggc cagggctcct gaactgtggg ttctcttctg      1171
agcgggaaac caaacaatgg tgtgggaatg aacaatttcc accttgatac atacatatac      1231
acatgcacac acacaaacaa acacacatac acacacactt ccagatgtaa cattgtacac      1291
agagccacag ttatcttctt taagtacaaa aggaaaaggg ttttcacctc cagatagaca      1351
gataatagat acacagacac acaagacaga tagatgatag ataacatata gattagatag      1411
ataatagata gatggtagat aggtagatgg atgatagata gatagataga ttggatagat      1471
agatagatag atagatagat agatagatag ataataacat gacagataag atgatagaaa      1531
taagatacga ta                                                          1543

<210> SEQ ID NO 6
<211> LENGTH: 268
<212> TYPE: PRT
<213> ORGANISM: Mus musculus

<400> SEQUENCE: 6

Met Leu Leu Trp Met Val Leu Leu Cys Asp Ser Met Val Glu Ala
1               5                   10                  15

Gln Glu Leu Phe Pro Asn Pro Glu Leu Thr Glu Phe Thr Asn Ser Glu
                20                  25                  30

Thr Met Asp Val Ile Leu Lys Cys Thr Ile Lys Val Asp Pro Lys Asn
            35                  40                  45

Pro Thr Leu Gln Leu Phe Tyr Thr Phe Tyr Lys Asp Asn His Val Ile
```

```
            50                  55                  60
Gln Asp Arg Ser Pro His Ser Val Phe Ser Ala Glu Ala Lys Glu Glu
 65                  70                  75                  80

Asn Ser Gly Leu Tyr Gln Cys Met Val Asp Thr Glu Asp Gly Leu Ile
                 85                  90                  95

Gln Lys Lys Ser Gly Tyr Leu Asp Ile Gln Phe Trp Thr Pro Val Ser
            100                 105                 110

His Pro Val Leu Thr Leu Gln His Glu Ala Thr Asn Leu Ala Val Gly
        115                 120                 125

Asp Lys Val Glu Phe Leu Cys Glu Ala His Gln Gly Ser Leu Pro Ile
    130                 135                 140

Phe Tyr Ser Phe Tyr Ile Asn Gly Glu Ile Leu Gly Lys Pro Leu Ala
145                 150                 155                 160

Pro Ser Gly Arg Ala Ala Ser Leu Leu Ala Ser Val Lys Ala Glu Trp
                165                 170                 175

Ser Thr Lys Asn Tyr Ser Cys Glu Ala Lys Asn Asn Ile Ser Arg Glu
            180                 185                 190

Ile Ser Glu Leu Lys Lys Phe Pro Leu Val Val Ser Gly Thr Ala Trp
        195                 200                 205

Ile Lys Ser Asn Met Leu Thr Ile Trp Leu Pro Ala Ser Leu Leu Gly
    210                 215                 220

Gly Met Val Ile Ala Ala Val Val Leu Met Tyr Phe Phe Lys Pro Cys
225                 230                 235                 240

Lys Lys His Ala Arg Pro Glu Met Pro Thr Leu Lys Glu Pro Asp Ser
                245                 250                 255

Phe Leu Tyr Val Ser Val Asp Asn Arg Arg Tyr Lys
            260                 265

<210> SEQ ID NO 7
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 7
ttgaattcac acacccacag gacctgcagc tgaa                              34

<210> SEQ ID NO 8
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 8
ttggatccac tgaaggaccc acagaaagag ttga                              34

<210> SEQ ID NO 9
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 9
accctgagat gtcagacaaa g                                            21

<210> SEQ ID NO 10
```

```
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 10
gccacctcac accagtaaag                                               20

<210> SEQ ID NO 11
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 11
cctccgatcc tgtattcctt c                                             21

<210> SEQ ID NO 12
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 12
tggagctgtg ggtggtatct g                                             21

<210> SEQ ID NO 13
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 13
agaacctcaa agaggagtga a                                             21

<210> SEQ ID NO 14
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 14
attatgctga gtgatatccc                                               20

<210> SEQ ID NO 15
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 15
atttaggtga cactatagaa                                               20

<210> SEQ ID NO 16
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 16
```

```
gggaattcat gttgccatct ttagttcc                                          28

<210> SEQ ID NO 17
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 17
aaggatccac tcctctctct ggagac                                            26

<210> SEQ ID NO 18
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 18
gcctcagaca gtggttcaaa                                                   20

<210> SEQ ID NO 19
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 19
agaaccatca cagtctcgca                                                   20

<210> SEQ ID NO 20
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 20
aagaattcca ccatggctgg acctgccac                                         29

<210> SEQ ID NO 21
<211> LENGTH: 41
<212> TYPE: DNA
<213> ORGANISM: Artificial
<220> FEATURE:
<223> OTHER INFORMATION: an artificially synthesized primer sequence

<400> SEQUENCE: 21
acagggtttg gccaggcttg ggcttcctgc actgtccaga g                           41

<210> SEQ ID NO 22
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 22
gcaggaagcc caagcctggc caaaccctgt                                        30

<210> SEQ ID NO 23
<211> LENGTH: 45
<212> TYPE: DNA
```

```
<213> ORGANISM: Artificial
<220> FEATURE:
<223> OTHER INFORMATION: an artificially synthesized primer sequence

<400> SEQUENCE: 23
ctaatacgac tcactatagg gcaagcagtg gtatcaacgc agagt                45

<210> SEQ ID NO 24
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 24
ctaatacgac tcactatagg gc                                         22

<210> SEQ ID NO 25
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 25
aagcagtggt atcaacgcag agt                                        23

<210> SEQ ID NO 26
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 26
ctcggatcct tgccatcttt agttccctgt gtt                             33

<210> SEQ ID NO 27
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 27
gctgtcgact tagttgctgg cgggagtgaa caagac                          36

<210> SEQ ID NO 28
<211> LENGTH: 63
<212> TYPE: DNA
<213> ORGANISM: Artificial
<220> FEATURE:
<223> OTHER INFORMATION: an artificially synthesized primer sequence

<400> SEQUENCE: 28
gcgaattcca ccatggacta caaagacgat gacgacaagt tgccatcttt agttccctgt   60
gtt                                                              63

<210> SEQ ID NO 29
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 29
```

```
cgtgtcgact cactagcaga gaacctcctc acagtc                                36

<210> SEQ ID NO 30
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 30
aggtcagagt gcaggctcct gtatc                                            25

<210> SEQ ID NO 31
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 31
tagaactgtc ctttctcccc acggt                                            25

<210> SEQ ID NO 32
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 32
gaattcacac acccacagga cctgca                                           26

<210> SEQ ID NO 33
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 33
ggatccactg aaggacccac agaaag                                           26

<210> SEQ ID NO 34
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 34
ctcagtaaag gcagagtgga gtacc                                            25

<210> SEQ ID NO 35
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 35
atacattaga accacagccg caatg                                            25

<210> SEQ ID NO 36
<211> LENGTH: 27
<212> TYPE: DNA
```

-continued

<213> ORGANISM: Artificial
<220> FEATURE:
<223> OTHER INFORMATION: an artificially synthesized primer sequence

<400> SEQUENCE: 36
ccatcctaat acgactcact atagggc                                   27

<210> SEQ ID NO 37
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 37
actcactata gggctcgagc ggc                                       23

<210> SEQ ID NO 38
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 38
ctcaagaagt tccccttggt tgtctc                                    26

<210> SEQ ID NO 39
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 39
gccagatagt tagcatgttg ctcttg                                    26

<210> SEQ ID NO 40
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 40
gaattcatgt cgctcatggt cgtcag                                    26

<210> SEQ ID NO 41
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 41
ggatcctcag ggctcagcat ttggaa                                    26

<210> SEQ ID NO 42
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 42
aggggcccag cttttctcca gcgatgaagg agaaagaaga                     40

<210> SEQ ID NO 43
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 43
tcttctttct ccttcatcgc tggagaaaag ctgggcccct                40

<210> SEQ ID NO 44
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 44
gcaattaacc ctcactaaag ggaac                               25

<210> SEQ ID NO 45
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 45
ttcatacaga aggcgtggag                                     20

<210> SEQ ID NO 46
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 46
cgttcgcggg cgcaactgca                                     20

<210> SEQ ID NO 47
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 47
gaattcatgg ccttaccagt gaccgc                              26

<210> SEQ ID NO 48
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 48
ggatccttag acgtatctcg ccgaaa                              26

<210> SEQ ID NO 49
<211> LENGTH: 30
<212> TYPE: DNA
<213> ORGANISM: Artificial
<220> FEATURE:

```
<223> OTHER INFORMATION: an artificially synthesized primer sequence

<400> SEQUENCE: 49
gaattccacc atggccttac cagtgaccgc                                              30

<210> SEQ ID NO 50
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 50
accagccagt tgctggcggg gtccagcccc ctcgtgtgca                                   40

<210> SEQ ID NO 51
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 51
tgcacacgag ggggctggac cccgccagca actggctggt                                   40

<210> SEQ ID NO 52
<211> LENGTH: 39
<212> TYPE: DNA
<213> ORGANISM: Artificial
<220> FEATURE:
<223> OTHER INFORMATION: an artificially synthesized primer sequence

<400> SEQUENCE: 52
atcagaacat gcaggtgtct tccagccccc tcgtgtgca                                    39

<210> SEQ ID NO 53
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 53
tgcacacgag ggggctggac agacacctgc atgttctgat                                   40
```